United States Patent
Bredehorst et al.

(10) Patent No.: US 10,238,735 B2
(45) Date of Patent: Mar. 26, 2019

(54) CONTROLLED ACTIVATION OF COMPLEMENT COMPONENTS FOR USE AS ENDOGENOUS ADJUVANT

(71) Applicants: PLS-Design GmbH, Hamburg (DE); Klinikum rechts der Isar der Technischen Universitat Munchen, Munich (DE); Helmholtz Zentrum Munchen Forschungszentrum fur Gesundheit und Umwelt GmbH, Neuherberg (DE)

(72) Inventors: Reinhard Bredehorst, Hamburg (DE); Thomas Grunwald, Hamburg (DE); Markus Ollert, Gauting (DE); Carsten Schmidt-Weber, Munich (DE); Edzard Spillner, Hamburg (DE)

(73) Assignees: PLS-DESIGN GMBH, Hamburg (DE); KLINIKUM RECHTS DER ISAR DER TECHNISCHEN UNIVERSITAT MUNCHEN, Munich (DE); HELMHOLTZ ZENTRUM MUNCHEN FORSCHUNGSZENTRUM FUR GESUNDHEIT UND UMWELT GMBH, Neuherberg (DE)

( * ) Notice: Subject to any disclaimer, the term of this patent is extended or adjusted under 35 U.S.C. 154(b) by 573 days.

(21) Appl. No.: 13/917,733

(22) Filed: Jun. 14, 2013

(65) Prior Publication Data
US 2013/0337045 A1    Dec. 19, 2013

(30) Foreign Application Priority Data
Jun. 14, 2012  (EP) .................................... 12075058

(51) Int. Cl.
| | | |
|---|---|---|
| A61K 39/395 | (2006.01) | |
| A61K 39/39 | (2006.01) | |
| A61K 9/00 | (2006.01) | |
| A61K 39/29 | (2006.01) | |
| A61K 39/00 | (2006.01) | |

(52) U.S. Cl.
CPC ............ *A61K 39/39* (2013.01); *A61K 9/0024* (2013.01); *A61K 39/292* (2013.01); *A61K 2039/55516* (2013.01)

(58) Field of Classification Search
None
See application file for complete search history.

(56) References Cited

U.S. PATENT DOCUMENTS

| 5,951,976 A * | 9/1999 | Segal .......................... 424/93.21 |
| 6,913,767 B1 * | 7/2005 | Cleland et al. ............... 424/468 |
| 7,553,931 B2 | 6/2009 | Kolln et al. |
| 8,119,769 B2 | 2/2012 | Kolln et al. |
| 2010/0179092 A1 | 7/2010 | Fritzinger |
| 2012/0045511 A1 * | 2/2012 | Tao ...................... A61K 9/0024 424/484 |

FOREIGN PATENT DOCUMENTS

| WO | 1999/018142 | 4/1999 |
| WO | 02/102309 | 6/2002 |
| WO | 2005/080210 | 2/2005 |

OTHER PUBLICATIONS

GlaxoSmithKline and Tolerx announce phase III DEFEND-1 study of otelixizumab in type 1 diabetes did not meet its primary endpoint. Issued: Friday Mar. 11, 2011, London UK and Cambridge, Mass, US, 3 pages.
Van Kooten, C., et al. (2008) Mol. Immunol. 45: 4064-4072.
Verschoor, A., et al. (2003) J. Immunol. 171: 5363-5371.
Vieyra, M., et al. (2011) Am. J. Pathol. 179: 766-744.
Viglietta, V., et al. (2004) J. Exp. Med. 199: 971-979.
Vogel, C. W., Müller-Eberhard, H. J. (1982) J. Biol. Chem. 257:8292-8299.
Vogel, C. W.; et al. (1985). Haematol. Blood Transfus. 29: 514-517.
Vogel, C.W., Fritzinger, D.C. (2007) Curr. Pharm. Des. 13: 2916-2926.
Vogel, C.W., Fritzinger, D.C. (2010) Toxicon 56: 1198-1222.
Walker, M.R., et al. (2003) J. Clin. Invest. 112: 1437-1443.
Willemse, J.L., et al. (2008) Clin. Chim. Acta 389: 181-182.
Wu, Y., et al. (2012) Biomaterials 33: 2351-3260.
Yamazaki, S., et al. (2003) J. Exp. Med. 198: 235-247.
Yiamouyiannis, C.A., et al. (1999) Am. J. Pathol. 154: 1911-1921.
Zhang, J., et al. (2006) Biomacromolecules 7: 2492-2500.
Zhou, W., et al. (2006) Blood 107: 2461-2469.
Zhou, W., et al. (2007) Mol. Immunol. 44: 57-63.
Zhou, W. (2012) Immunobiology 217: 225-234.
Ahearn et al. (1996) Immunity 4: 251-262.
Akira and Takeda (2004) Nat. Rev. Immunol. 4: 499-511.
Alhalaweh et al. (2009) Eur. J. Pharm. Sci. 38: 206-214.
Alper et al. (1969) Science 163: 286-288.
Bohnsack and Cooper (1988) J. Immunol. 141: 2569-2576.
Böttger et al. (1985). J. Immunol. 135: 4100-4107.
Böttger et al. (1986) J. Immunol. 137: 1280-1285.
Burke et al. (2004) Clin. Diag. Lab. Immunol. 11: 588-598.
Bye et al. (1984) Gastroenterology 86: 789-801.
Chang et al. (2001) Vaccine 19: 2884-2889.
Chou et al. (2010) J. Immunol. 185: 5468-5475.
Chow et al. (1998) J. Immunol. 160: 1320-1329.
Clapp et al. (2011) J. Pharm. Sci. 100: 388-401.
Croix et al. (1996) J. Exp. Med. 183: 1857-1864.
DeBruijn and Fey (1985) Proc. Natl. Acad. Sci. USA 708-712.
Dempsey et al. (1996) Science 271:348-350.
Dolmer and Sottrup-Jensen (1993) FEBS Lett. 315: 85-90.
Fischer et al. (1996) J. Immunol. 157: 549-556.

(Continued)

*Primary Examiner* — Yunsoo Kim
(74) *Attorney, Agent, or Firm* — Stuart H. Mayer; Mayer & Williams PC

(57) ABSTRACT

The invention relates to a pharmaceutical composition made of one or more preparation and comprising a therapeutically effective dose of at least one recombinant human C3-derivative and at least one antigen für vaccination.

15 Claims, 7 Drawing Sheets

Specification includes a Sequence Listing.

(56) References Cited

OTHER PUBLICATIONS

Ganem and Prince (2004) N. Engl. J. Med. 350: 1118-1129.
Goncalves et al., 2004) Virology 326: 20-28.
Green et al. (2001) Vaccine 20: 242-248.
Greginat et al. (2001) J. Exp. Med. 194: 1711-1719.
Haas et al. (2002) Immunity 17: 713-723.
HogenEsch (2002) Vaccine20: S34-S39.
Koch et al. (2005) Virology 340: 277-284.
Koleva et al. (2002) Gastroenterology 122: 697-708.
Kolla et al. (2007) PloS ONE 2 : e1044.
Kopf et al. (2002) Nat. Med. 8: 373-378.
Lachmann et al. (1982) J. Exp. Med. 156: 205-216.
Lang et al. (1987) Cell 51: 675-686.
Law and Dodds (1997) Protein Sci. 6: 263-274.
Leroux-Roels (2010) Vaccine 285: C25-C36.
Martinelli et al. (1978) J. Immunol. 121: 2043-2047.
Medicus et al. (1976) J. Exp. Med. 144: 1076-1093.
Milich and Chisari (1982) J. Immunol. 129: 320-325.
Milich and Leroux-Roels (2002) Autoimmun. Res. 2: 248-257.
Molina et al. (1996) Proc. Natl. Acad. Sci. USA 93: 3357-3361.
Newman et al. (1984) Complement 1: 213-227.
Nicholls et al. (2010) Ann. N.Y. Acad. Sci. 1213: 46-61.
Nielsen et al. (2002) J. Leuk. Biol. 72: 249-261.
O'Neil et al. (1988) J. Immunol. 140: 1939-1945.
Pepys (1974) J. Exp. Med. 140: 126-145.
Petrowsky et al. (2004) Immunol. Cell Biol. 82: 488-492.
Pihlgren et al. (2004) Vaccine 23: 329-335.
Ross et al. (1982) J. Immunol. 129: 2051-2060.
Suradhat et al. (2001) Vet. Immunol. Immunopathol. 83: 79-92.
Tack et al. (1980) Proc Natl Acad Sci USA 77: 5764-5768.
Test et al. (2001) Infect. Immun. 69:3031-3040.
Villiers et al. (1999) J. Immunol. 162: 3647-3652.
Villiers et al. (2003) Int. Immunol. 15: 91-95.
Zaharoff et al. (2007) Vaccine 25: 2085-2094.
Zhang et al. (2007) Blood 110: 228-236.
Abe, M., et al. (2001) J. Immunol. 167: 4651-4660.
Akbar, A.N., et al. (2003) Immunology 109: 319-325.
Andersson, A., et al. (1997) Eur. J. Immunol. 27: 1762-1768.
Andra, J., et al. (2002) Mol. Immunol. 39: 357-365.
Avni, O., et al. (2002) Nat. Immunol. 3 : 643-651.
Ballow, M., Cochrane, C. G. (1969) J. Immunol. 103: 944-952.
Bancherau, J., et al. (2000) Annu. Rev. Immunol. 18: 767-811.
Bao, L., et al. (2009) J. Clin. Invest. 119: 1264-1274.
Bautsch, W., et al. (2000) J. Immunol. 165: 5401-5405.
Bluestone, J.A., et al. (2010) Nature 464: 1293.
Calabresi, P.A., et al. (2003) J. Neuroimmunol. 139: 58-65.
Cardone, J., et al. (2010) Nat. Immunol. 11 :862-872.
Carrol, M.C. (2004) Nat. Immunol. 5: 981-986.
Choi, S., et al. (2003) Pharmaceut. Res. 20: 2008-2010.
Cochrane, C. G., et al. (1970) J. Immunol. 105: 55-69.
Coppieters, K.T., et al. (2012) J. Exp. Med. 209: 51-60.
Diamyd (2011) Diamyd US phase III trial: http://clinicaltrials.gov/ct2/show/NCT00751842, 3 pages.
Diamyd (2011) Diamyd European phase III trial: http://clinicaltrials.gov/ct2/show/NCT00723411, 3 pages.
Diamyd (2011) Diabetes prevention—immune tolerance (DIAPREV-IT) http://clinicaltrials.gov/ct2/show/NCT01122446?term=diamyd&rank=6, 4 pages.
Drouin, S.M., et al. (2001) J. Immunol. 167: 4141-4145.
Drouin, S.M., et al. (2006) Am. J. Respir. Crit. Care Med. 173: 852-857.
Dunkelberger, J.R., Song, W.-C. (2010) Cell Res. 20: 34-50.
Duschl, A., et al. (1992) Eur. Cytokine Netw. 3: 97-102.
Ehirchiou, D., et al. (2007) J. Exp. Med. 204: 1510-1524.
Ezekowitz, R.A., et al. (1984) J. Exp. Med.150: 244-260.
Fang, C., et al. (2009) Blood 114: 1005-1015.
Farrar, C.A., et al. (2006). FASEB J. 20: 217-226.
Fontenot, J.D., et al. (2003) Nat. Immunol. 4: 330-336.
Fritzinger, D.C., et al. (2008a). Mol. Immunol. 45: 4112.

Fritzinger, D.C., et al. (2008b) Adv. Exp. Med. Biol. 632: 293-307.
Fritzinger, D.C., et al. (2009) Dev. Comp. Immunol. 33: 105-116.
Gerard, PN.P., Gerard, C. (2002) Curr. Opin. Immunol. 14: 705-708.
Ghannam, A., et al. (2008) J. Immunol. 181: 5158-5166.
Gilbert, J.C., et al. (1987) J. Control. Release 5: 113-118.
Gong, C.Y., et al. (2009a) Int. J. Pharm. 365: 89-99.
Gong, C.Y., et al. (2009b) BMC Biotechnol. 9: 8.
Grote, A., et al. (2005) NAR 33: W526-531.
Grunewald, S.M., et al. (1997) J. Biol. Chem. 272: 1480-1483.
Gueler, F., et al. (2008) J. Am. Soc. Nephrol. 19: 2302-2312.
Hagenaars, N., et al. (2010) J. Control. Release 144: 17-24.
Hashimoto, M., et al. (2010) J. Exp. Med. 207: 1135-1143.
Hawlisch, H., et al. (2004) Mol. Immunol. 41: 123-131.
Heeger, P.S., Kemper, C. (2012) Immunobiology 217: 216-224.
Hering, B.J., et al. (2004) Am. J. Transplant. 4: 390-401.
Herold, K.C., et al. (2002) N. Engl. J. Med. 346: 1692-1698.
Homann, D., von Herrath, M. (2004) Clin. Immunol. 112: 202-209.
Humbles, A.A., et al. (2000) Nature 406: 998-1001.
Hyun, H., et al. (2007) Biomacromolecules 8: 1093-1100.
Janssen, B.J.C., et al. (2009) EMBO J. 28: 2469-2478.
Jeong, B., et al. (1997) Nature 388: 860-862.
Juedes, A.E., von Herrath, M.G. (2004) Diabetes Metab. Res. Rev. 20 : 446-451.
Kang, Y.M., et al. (2010) Biomaterials 31: 2453-2460.
Karp, C.I., et al. (2000) Nat. Immunol. 1: 221-226.
Karsten, C.M., Kohl, J. (2010) Nat. Immunol. 11: 775-777.
Kawamoto, S., et al. (2004) J. Clin. Invest. 114: 399-407.
Kemper, C., Atkinson, J.P. (2007) Nat. Rev. Immunol. 7: 9-18.
Keymeulen, B. (2005) N. Engl. J. Med. 352: 2598-2608.
Knip, M., et al. (2005) Diabetes 54: S125-S136.
Köhl, J., et al. (2006) J. Clin. Invest. 116: 783-796.
Kölln, J., et al. (2004) J. Immunol. 173: 5540-5545.
Kölln, J., et al. (2005) Immunol. Lett. 98: 49-56.
Kretschmer, K., et al. (2005) Nat. Immunol. 6: 1219-1227.
Kukreja, A., et al. (2002) J. Clin. Invest. 109: 131-140.
Kwan, W.-h., et al. (2012) Immunol. Res. DOI 10.1007/s12026-012-8327-1.
Li, K., et al. (2008) Blood 112: 5084-5094.
Li, Q., et al. (2010) J. Am. Soc. Nephrol. 21: 1344-1353.
Lin, M., et al. (2010) Diabetes 59: 2247-2252.
Liu, J., et al. (2008) J. Immunol. 180: 5882-5889.
Ludvigsson, J., et al. (2008) N. Engl. J. Med. 359: 676-781.
MacroGenics press release (Oct. 20, 2011) Pivotal clinical trial of teplizumab did not meet primary efficacy endpoints. http://www.macrogenics.com/press_releases-284.html.
Mathews, K.P. (1980) Ann. Intern. Med. 93: 443-445.
Morgan, B.P., Gasque, P. (1997) Clin. Exp. Immunol. 107: 1-7.
Mulligan, M.S., et al. (1996) J. Clin. Invest.98: 503-512.
Munegowda, M.A., et al. (2011) J. Clin. Immunol. 31: 811-826.
Pai, S.S., et al. (2009). AAPS J. 11: 88-98.
Pavlov, V., et al. (2008) J. Immunol. 181: 4580-4589.
Peng, Q., et al. (2006) J. Immunol. 176: 3330-3341.
Peng, Q., et al. (2008) Blood 111: 2452-2461.
Peng, K.-T., et al. (2010) Biomaterials 31: 5227-5236.
Petrella, E.C., et al. (1987) J. Immunol. Meth. 104: 159-172.
Pratt, J.R., et al. (2002) Nat. Med. 8: 582-587.
Puigbo P., et al. (2007) NAR 35: W126-131.
Qiao, M. et al. (2005) Int. J. Pharm. 294: 103-112.
Raedler, H., et al. (2009) Am. J. Transplant. 9: 1784-1795.
Raedler, H., et al. (2011) Am. J. Transplant. doi:10.1111/j.1600-6143.2011.03561.x.
Razeghifard, M.R. (2004) Prot. Expr. Purif. 37: 180-186.
Reis e Sousa (2006) Nat. Rev. Immunol. 6: 476-483.
Reis e Sousa, et al. (2007) Immunobiology 212: 151-157.
Sakaguchi, S., et al. (1985) J. Exp. Med. 161: 72-87.
Sandor, N., et al. (2009) Mol. Immunol. 47: 438-448.
Shortman, K., Liu, Y.J. (2002) Nat. Rev. Immunol. 2: 151-161.
Sinha, V.R., et al. (2004). Int. J. Pharm. 278: 1-23.
Skyler, J.S., et al. (2005) Diabetes Care 28: 1068-1076.
Stäger, S., et al. (2003) Nat. Med. 9: 1287-1292.
Strainic, M.G., et al. (2008) Immunity 28: 425-435.
Suresh, M., et al. (2003) J. Immunol. 170: 788-794.
Szabo, S.J., et al. (1995) Immunity 2: 665-675.

(56) References Cited

OTHER PUBLICATIONS

Taniguchi, S., et al. (1996) Transplantation 62: 678-681.
Till, G.O., et al. (1982) J. Clin. Invest. 69: 1126-1135.
Till, G.O., et al. (1987) Am. J. Pathol. 129: 44-53.
F. Danhier et al., "PLGA-based nanoparticles: An overview of biomedical applications", Journal of Controlled Release 161 (2012) 505-522.
Silva et al., "Immunomodulation against microbial pathogens through dendritic cells" (2013) in: Microbial pathogens and strategies for combating them: science, technology and education (A. Mendez-Vilas, ed.), vol. 3: p. 1686-1705.

* cited by examiner

CONTROLLED ACTIVATION OF COMPLEMENT COMPONENTS FOR USE AS ENDOGENOUS ADJUVANT

INTRODUCTION

Recombinant or synthetic antigens used in modern day vaccines pose the problem that they are generally far less immunogenic than conventional attenuated whole organism vaccines. As a result, there is a major need for improved and more powerful adjuvants for use with these vaccines. With few exceptions, aluminum hydroxide or phosphate salts (alum) remain the sole adjuvants approved for human use in the majority of countries worldwide. Alum-based adjuvants are able to induce a good response of Th2 antibody isotypes, but the inability to induce Th1 antibody isotypes or cellular immune responses, and the poor adjuvant effect on polysaccharide antigens are limiting their applicability to many vaccines.

In the recent past, a huge variety of natural and synthetic compounds with adjuvant activity has been identified and many of them are clearly more potent than alum. However, these adjuvants have failed to be successful in humans largely because of toxicity, stability, bioavailability and/or cost. Toxicity is perhaps the single most important impediment in introducing most such adjuvants to human use. Alum-based vaccines are generally well tolerated, although granulomas are common when the subcutaneous or intradermal route is used rather than intramuscular injection. Furthermore, increased IgE production, allergenicity and neurotoxicity are additional limitations of alum-based adjuvants. However, serious side effects of alum-based adjuvants are relatively rare. Therefore, the challenge in adjuvant research is to gain potency while minimizing toxicity, at least to a comparable level like alum.

The complement system provides excellent opportunities for achieving this objective. The ability of activated complement components to stimulate the immune response has been documented in various studies. However, the controlled use of this potent system as an endogenous adjuvant for efficient, but non-toxic induction of immune responses remains a major challenge.

The activation of the complement system can be achieved by three different pathways, the classical antibody-dependent activation pathway, the alternative activation pathway and the lectin activation pathway. The alternative activation pathway as well as the lectin-pathway were shown not to be dependent on antibodies. All pathways share a similar cascade-like organization, wherein the protease acts on pro-enzymes (zymogenes) of a subsequent protease. This cascade results in an amplification of the initiation signals. The central step of the complement cascade resides in the formation of a C3-convertase, which cleaves C3 to C3b and C3a. Subsequently, the resulting C3b can act as a part of a C5-convertase, which cleaves C5 in C5b and C5a. In the terminal way, initiated by the generation of C5b, the gradual accumulation of C6, C7, C8 and several molecules C9 result in the formation of the membrane attack complex which is capable of forming a pore in the membrane of the target cells thereby effecting lysis of the cells.

The complement protein C3 is the central component of all activation pathways. It is predominantly expressed in the liver as a 1663 amino acid precursor protein (Alper et al., 1969). After the 22 amino acid signal sequence has been cleaved off, the precursor protein is proteolytically cleaved into two chains by removal of four arginine residues. The resulting α-chain has a molecular weight of 115 kDa and the β-chain has a molecular weight of 73 kDa (DeBruijn and Fey, 1985). The chains are linked by a disulfide bridge and by non-covalent interactions (Dolmer and Sottrup-Jensen, 1993).

C3 is cleaved between the amino acids $Arg^{726}$ and $Ser^{727}$ by the C3-convertases. The 9 kDa C3a, which results from the cleavage, is an anaphylatoxin and causes an increase in chemotaxis as well as an increase in the vascular permeability of the blood capillaries. By cleavage of the 179 kDa-C3b between the amino acid $Cys^{988}$ and $Glu^{991}$ a highly reactive thioester is released, by the use of which C3b binds on the cell surfaces via transacetylation (Tack et al., 1980). Furthermore, several binding sites for different complement proteins are exposed by the cleavage, which explain the various interactions of the C3b-molecule. Several regulatory and/or complementary proteins interact with C3b, which comprises binding sites for CR1 or Factor H, which act as co-factors for the cleavage by the protease Factor I. Factor I cleaves C3b between $Arg^{1281}$ and $Ser^{1282}$ and $Arg^{1298}$ and $Ser^{1299}$, whereby the fragments C3f and C3bi emerge, the latter of which is inactive and unable to bind Factor B and C5 (Lachmann et al., 1982). C3bi, however, is capable to remain on the surface of pathogens, where it is recognized by CR3, which occurs on macrophages and killer cells. Subsequently, CR3 mediates the destruction of pathogens (Newman et al., 1984). In case CR1 acts as a co-factor for the protease, Factor I can additionally cleave between amino acids $Arg^{932}$ and $Glu^{933}$, thereby forming C3dg and C3c (Ross et al., 1982). C3dg is also capable to remain on the surface and is recognized by CR2 (CD21), which is expressed on B-lymphocytes and dendritic cells (Law and Dodds, 1997). The binding of C3dg to the complement receptor CR2 leads to the activation of the B cells (Bohnsach and Cooper, 1988).

Role of Complement Component C3 for Immune Responses.

Complement component C3 has been shown to be an important element in controlling IgG response and the induction of germinal center in lymph nodes. Animals depleted of C3 by administration of cobra venom factor (CVF; Pepys, 1974; Martinelli et al., 1978; Böttger et al., 1986), or genetically deficient in C3 (Böttger et al., 1985; O'Neil et al., 1988; Fischer et al., 1996), or in complement receptor CD21/35 (Ahearn et al., 1996; Molina et al., 1996; Croix et al., 1996) exhibit significantly impaired antigen-specific IgG and germinal center responses. Mechanisms contributing to the impaired immune response include a defect in a) B cell signalling via BCR-CD19-CD21 complex, b) antigen localization in lymphoid organs and/or (c) interaction between follicular dendritic cells and B cells (for a review, see Nielsen and Leslie, 2002).

Several studies have demonstrated that complement component C3 is also involved in priming antiviral T cell immunity. For example, a significant impairment in priming of $CD4^+$ helper cells and virus-specific cytotoxic T lymphocytes was observed upon infection of C3-deficient mice with influenza virus, which resulted in delayed clearance of the infection and increased viral titers (Kopf et al., 2002). In another study the induction and expansion of $CD8^+$ T cells during infection with lymphocytic choriomeningitis virus (LCMV) was shown to be dependent on C3 (Suresh et al., 2003).

Role of Complement Fragments C3a and C5a for Innate and Adaptive Immune Responses.

A recent study has demonstrated that the anaphylatoxins C3a and C5a and their receptors C3aR and C5aR regulate Toll-like receptor (TLR)-mediated inflammatory responses of the innate immune system which play an essential role in orchestrating adaptive immune responses (Zhang et al., 2007).

Upon treatment with the TLR4-ligand lipopolysaccharide (LPS), the TLR2/6-ligand zymosan, and the TLR9-ligand CpG-oligonucleotide, mice deficient in the membrane complement inhibitor decay-accelerating factor (DAF), reacted in this study in a complement-dependent manner with strikingly elevated plasma levels of interleukin-6 (IL-6), tumor necrosis factor α (TNF-α), IL-1β and/or decreased plasma levels of IL-12 as compared to wild-type mice (Zhang et al., 2007). Since IL-6 and TNF-α are most effective in stimulating proliferation of human naïve $CD4^+$ T-cells (Greginat et al., 2001), the cytokine response appears to produce a local or systemic cytokine milieu favorable for T-cell priming and/or survival of effector and memory cells (Akira et al., 2004; Carroll, 2004).

It is important to note that all TLR-ligands used in this study are capable of activating the complement system. LPS is a well-known activator of both the alternative and lectin pathways of complement. The insoluble carbohydrate zymosan from the yeast cell wall a well-known activator of the alternative complement pathway, and CpG-oligonucleotides have also been shown to activate complement (Zhang et al., 2007). Based on the complement activating ability of the TLR-ligands, more detailed studies revealed that the regulatory effect of complement on TLR-induced inflammatory cytokines in vivo is mediated by the anaphylatoxins C3a and C5a and their receptors C3aR and C5aR (Zhang et al., 2007). C3aR played a more important role than C5aR in regulating TLR9 signaling, whereas TLR4 signaling was predominantly mediated by C5aR.

Most important, the regulatory effect of complement on TLR-mediated cytokine production correlates apparently with the degree of complement activation, which explains the different plasma levels of inflammatory cytokines in $DAF^{-/-}$ mice and wild-type mice upon treatment with complement-activating TLR-ligands. DAF (CD55) is a glycosylphosphatidylinositol-linked membrane regulator of complement that is present on most mammalian cell types. DAF inhibits C3 and C5 convertases of both the classical and alternative pathways of complement and its deletion in the mouse renders the animal more susceptible to a higher degree of complement activation. Therefore, it is not surprising that co-treatment of wild-type mice with TLR ligands and cobra venom factor (CVF), a potent complement activator, yielded similar results as observed in $DAF^{-/-}$ mice (Zhang et al., 2007). CVF co-treatment of wild-type mice greatly increased LPS-induced plasma IL-6 and decreased LPS-induced plasma IL-12 concentrations. The same observation was made after co-treatment of wild-type mice with CVF and zymosan. Altogether these observations point to the fact that CVF-induced complement activation promotes TLR-ligand-induced production of inflammatory cytokines and, thereby, modulates the adaptive immune response.

CVF-Mediated Activation of the Complement System.

As evident from the study of Zhang et al. (2007), common PAMPs (pathogen-associated molecular patterns) such as LPS or zymosan act both as TLR-ligands and activators of complement, but their activating activity is restricted by several complement regulatory proteins such as DAF. Therefore, efficient TLR-induced production of inflammatory cytokines by LPS or zymosan required either a deficiency in DAF or non-regulated activation of complement by cobra venom factor (CVF) (Zhang et al., 2007).

Based on this observation, CVF-mediated activation of the complement systems represents conceptually a promising possibility in adjuvant research for gaining potency while minimizing toxicity. CVF, a 149 kDa-glycoprotein, is a potent complement activator of the venom of the cobra (for a review, see Vogel and Fritzinger, 2010). CVF shares an identity of 51% and a similarity of 70% on the protein level with human C3. Moreover, both proteins have a chain structure of the same kind. This high similarity is also reflected by the fact that CVF—as C3b—can bind to Factor B and forms a convertase by the Factor D-initiated cleavage of B in Bb and Ba. In contrast to C3Bb, the CVF-dependent convertase CVFBb, however, is a C3- and C5-convertase. By the resistance of CVFBb towards Factor H and Factor I, a convertase is formed with a much higher half-life of 7 h under physiological conditions. In comparison, C3bBb has a half-life of 1.5 min. In addition to the increased stability, the CVF-dependent convertase CVFBb cleaves C3 and C5 also in fluid phase, whereas C3-dependent convertase C3bBb is only active when bound to the cell surface. Due to these characteristics CVF effects a permanent activation of the complement system, leading to the depletion of complement components.

The lack of toxicity of complement activation by injection of CVF in laboratory animals has been documented by various studies (for a review, see Vogel and Fritzinger, 2010). All known effects of CVF are mediated by binding to factor B and the resulting activation of complement. No off-target activity has been observed. Transgenic mice constitutively expressing CVF (Andrä et al., 2002) display no apparent abnormal phenotype, exhibit a normal life span, reproduce normally, and do not show any tendency to develop infections (for a review, see Vogel and Fritzinger, 2010). The plasma C3 concentration of the transgenic mice varied between below 10% to almost 40% of normal mice. The only acute side effect observed after massive intravascular activation of complement by CVF is a C5a-mediated transitory inflammation of the lung due to sequestration of activated neutrophils (Till et al., 1982; Till et al., 1987; Mulligan et al., 1996). However, the occurrence and intensity of this inflammatory lung injury can be easily controlled by the amount and the rate of C5a generation.

Despite these favorable characteristics therapeutic applications of CVF pose serious problems due to its strong immunogenic character. CVF contains complex, N-bound oligosaccharide chains with terminal galactosyl residues, which have an enormous immunogenic potential (Taniguchi et al., 1996). Even deglycosylated CVF is likely to be too immunogenic, especially for repeated applications, given the phylogenetic distance between humans and cobras. Therefore, CVF is not suitable for use as an adjuvant in humans.

Use of C3 Fragments as Molecular Adjuvant.

As an alternative to CVF-induced complement activation the C3d-fragment of complement component C3 has been evaluated in mice as a natural molecular adjuvant. Since a genetically engineered antigen containing three copies of C3b has been demonstrated to significantly augment antigen-specific antibody titers (Dempsey et al., 1996), C3d has been used for a variety of vaccine applications including measles hemagglutinin (Green et al., 2001), bovine rotavirus VP7 and bovine herpesvirus type 1 glycoprotein D (Suradhat et al., 2001), pneumococcal serotype 14 capsular polysaccharide (Test et al., 2001), Streptococcus pneumoniae (Haas et al., 2002), HIV-1 gp120 (Koch et al., 2005) and anthrax protective antigen (Kolla et al., 2007).

C3d facilitates antigen retention by binding to complement receptors CD21 (CR2)/35 expressed on both B cells and follicular dendritic cells (FDCs). FDCs do not efficiently endocytose antigen and, thereby, may protect bound antigen from proteolysis which creates a potential depot effect. In addition to focusing antigen to the B cell surface, C3d promotes B cell activation by co-aggregating the B cell receptor and CD21, resulting in enhanced signalling via CD21-associated CD19. In addition, C3d fixation facilitates the uptake and presentation of antigen to recruit T cell help. It is known that CD19 and CD21 are crucial for germinal center formation and resultant memory B cell generation.

It should be noted, however, that the C3d-conjugation approach takes only partial advantage of the complement system as an endogenous adjuvant. C3d-conjugation has been shown to promote the recruitment of antigen-specific B cells into the primary response and the maintenance of the memory B cell compartment, but this approach excludes the supporting effect of other C3-fragments including the regulatory effect of C3a and C5a on TLR-mediated production of inflammatory cytokines and the enhancing effect of C3b on antibody responses. For example, amplification of adult antibody responses and improved affinity maturation were observed after immunization with antigen complexed to C3b via a physiological ester link (Villiers et al., 1999; Villiers et al., 2003). Furthermore, another study has demonstrated that in adult wild-type mice the use of C3b-conjugated antigen significantly increased secondary antibody response and in infant mice primary antibody responses, especially during the first 3 weeks of life (Pihlgren et al., 2004).

In summary, the various approaches and their limitations clearly show that there is a need in the field for an alternative approach that takes full advantage of various complement components and fragments thereof for an optimized vaccination strategy.

SUMMARY OF THE INVENTION

Activated complement components have been demonstrated to effectively stimulate the immune response, but the majority of recombinant or synthetic antigens used in modern day vaccines do not activate the complement cascade. This problem is solved by the present invention in that methods for a controlled activation of the complement system at the site of antigen presentation are provided. Thereby, activated complement components capable of augmenting immune responses are generated at the site of antigen presentation and serve as an endogenous adjuvant for efficient and non-toxic induction of immune responses.

In one embodiment, the present invention discloses recombinant human C3-derivatives (rhC3-derivatives) for controlled activation of the complement system which a) are able to form a physico-chemically stable convertase displaying a relatively long half-life of its decay-dissociation similar to that of the CVF,Bb convertase, b) are resistant to the action of Factor H or the combined action of Factors H and I, c) exert only little to negligible C5-cleaving activity thereby minimizing or eliminating potential C5a-mediated toxicity, and d) exhibit only low to negligible immunogenicity.

In another embodiment, the present invention discloses methods for a controlled activation of the complement system. In one method, a rhC3-derivative is co-injected with one or more antigens (or antigenic extracts) adsorbed onto aluminium salts or other depot-mediating materials. In another method, the vaccination process includes repeated injections of a rhC3-derivative at the site of antigen presentation. First, a recombinant human C3 derivative is co-injected with one or more antigens (or antigenic extracts) adsorbed onto aluminium salts or other depot-mediating materials. Thereafter, the recombinant human C3 derivative is injected again once or more at the site of antigen presentation. In a more preferred method, activated complement components are continuously generated by a sustained release of recombinant human C3 derivatives from a depot at the site of antigen presentation. Most preferred for a sustained release of recombinant human C3 derivatives are injectable in situ-forming gel systems which are biodegradable. For prolonged antigen presentation at the site of the gelled polymer composit, one or more antigens (or antigenic extracts) are adsorbed onto aluminium salts or other depot-mediating materials and injected in close proximity of the gelled polymer composit. Alternatively, one or more antigens (or antigenic extracts), adsorbed onto a depot-mediating material or non-adsorbed, are co-incorporated in the gel system containing the rhC3-derivative.

In another embodiment, the present invention discloses vaccine compositions which are useful for the method of the present invention. In one specific embodiment, the vaccine composition comprises a biodegradable thermogelling polymer solution containing a recombinant human C3 derivative. For prolonged antigen presentation at the site of the gelled polymer composit, one or more antigens (or antigenic extracts) are adsorbed onto aluminium salts or other depot-mediating materials and injected in close proximity of the gelled polymer composit. In another specific embodiment, the vaccine composition comprises a biodegradable thermogelling polymer solution containing a recombinant human C3 derivative and one or more antigens (or antigenic extracts), adsorbed onto a depot-mediating materials or non-adsorbed.

In another embodiment, the present invention discloses therapeutic vaccination methods using the vaccine compositions of the present invention. Preferred examples of routes of administration include but are not limited to intradermal, subcutaneous and intramuscular administrations. Mucosal immunization represents another preferred embodiment of the present invention. In a specific embodiment of the present invention, a thermo-sensitive polymer solution formulated on the basis of cationic chitosan derivatives, which contains rhC3-derivatives and one or more antigens (or antigenic extracts) is administered intranasally.

In another embodiment, the present invention discloses methods for incorporating vaccine compositions into pharmaceutical compositions suitable for administration.

In still another embodiment, the present invention discloses methods for hepatitis B vaccination using PLGA-PEG-PLGA hydrogel-delivered HbsAg and rhC3-derivatives.

Specific preferred embodiments of the present invention will become evident from the following more detailed description and the claims.

DETAILED DESCRIPTION OF THE INVENTION

Figure 1:
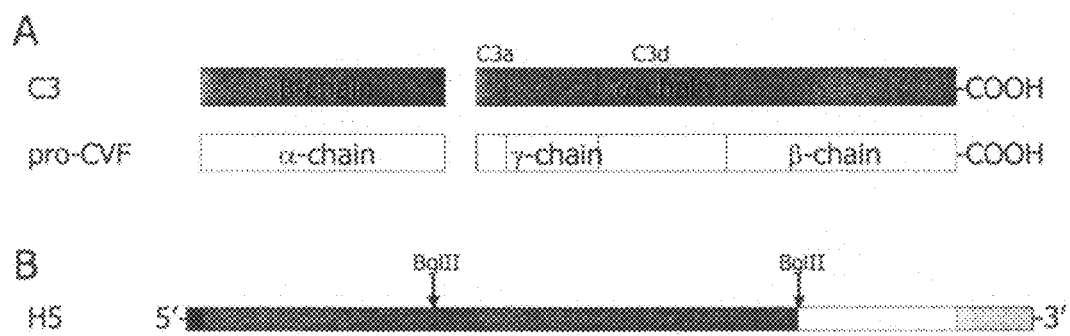
FIG. 1 is a schematic representation of the rhC3-derivative H5 encoding a hybrid protein of approx. 91% identity with human C3. A: Chain structures of C3 and pro-CVF. B: Structure of the cDNA of H5. The dark part of the nucleic acid sequence from the 5' end up to the BglII in Example 1.4. The Figure shows the mean values±standard deviation of at least three independent experiments.

Recombinant or synthetic antigens used in modern day vaccines are generally weak immunogenic and require a powerful adjuvant to induce strong humoral and cellular immune responses. The ability of activated complement components to stimulate the immune response has been documented in various studies, but the majority of antigens used in modern day vaccines such as soluble proteins do not activate the complement cascade. This problem is solved by the present invention in that methods for a controlled activation of the complement system at the site of antigen presentation are provided. Thereby, activated complement components capable of augmenting immune responses are generated at the site of antigen presentation. The methods of the present invention allow the controlled use of this potent system as an endogenous adjuvant for efficient and non-toxic induction of immune response.

I. Complement Activation with Recombinant Human C3-Derivatives (rhC3-Derivatives)

Recombinant human C3-derivatives useful for the present invention provide several important properties. Most important, such derivatives must be able to form a physico-chemically stable convertase displaying a relatively long half-life of its decay-dissociation similar to that of the CVF,Bb convertase. Second, such derivatives must be resistant to the action of Factor H or the combined action of Factors H and I. Furthermore, such derivatives should exhibit only little to negligible immunogenicity to allow for repeated injections or sustained release from biodegradable polymers. Last but not least, such derivatives should exert only low to negligible C5-cleaving activity to minimize or eliminate potential C5a-mediated toxicity.

Useful rhC3-derivatives were generated by replacing small stretches of human C3 at the very C-terminus of the C3 α-chain with homologous stretches of sequence from the CVF β-chain which contains the crucial stability site responsible for forming a stable convertase.

Several rhC3-derivatives providing the desired properties have been generated and characterized. For example, rhC3-derivative H5 expressed in CHO and HEK293 cells provides a 90% sequence identity with human complement component C3 and exhibits approx. 85% of the complement-consuming activity of purified native CVF (Kölln et al., 2004; U.S. Pat. No. 7,553,931 B2). The recombinant protein activates Factor B by producing Bb and Ba in the presence of Factor D and $Mg^{2+}$ in an identical manner as C3(H2O) and CVF. Further analyses revealed a half-life of the rhC3-derivative H5-dependent convertase of approx. 5-6 hours, which is close to the reported 7 hour half-life of the CVF-dependent convertase (Vogel and Müller-Eberhard, 1982). The potential immunogenicity of this derivative in humans can be assumed to be very low.

The rhC3-derivative H6 expressed in CHO and HEK293 cells provides a 96% sequence identity with human complement component C3 and still exhibits approximately 70% of the complement activating activity of CVF. The derivative does not exert significant C5-convertase activity (Minn et al., 2004; Minn et al., 2005; U.S. Pat. No. 7,553,931 B2). As a result of the high sequence identity with human complement component C3, the potential immunogenicity of this derivative in humans can be assumed to be extremely low or even negligible.

Expression of rhC3-derivative HC3-1496 in *Drosophila* S2 cells yielded a molecule with comparable properties. HC3-1496, a construct in which the C-terminal 168 amino acid residues of the C3α-chain have been replaced with the corresponding 168 amino acid residues from the β-chain of CVF, forms a convertase which is more stable than CVF,Bb and provides a higher C3-cleaving activity than that of CVF. Furthermore, HC3-1496 exerts no or only residual C5-cleaving activity. Due to its 94% sequence identity with human complement component C3, the potential immunogenicity of this derivative in humans also can be assumed to be very low or even negligible (Vogel and Fritzinger, 2007; Fritzinger et al., 2009, for a review, see Vogel and Fritzinger, 2010; US patent 2010/0179092 A1).

II. Safety Aspects of Complement Activation with rhC3-Derivatives

No adverse side effects upon injection of CVF in laboratory animals have been observed in numerous studies (for a review, see Vogel and Fritzinger, 2010). Most of these studies involved complement depletion for a few days up to one month. Furthermore, transgenic mice constitutively expressing CVF (Andra et al., 2002) display no apparent abnormal phenotype, exhibit a normal life span, reproduce normally. During approximately one decade of continued maintenance under normal animal housing conditions, no tendency to develop infections has been observed (for a review, see Vogel and Fritzinger, 2010). These data suggest that at least short-term complement depletion may be safe.

As mentioned earlier, the only acute side effect observed after intravascular activation of complement by CVF is a C5a-mediated transitory inflammation of the lung as a result of sequestration of activated neutrophils (Till et al., 1982; Till et al., 1987; Mulligan et al., 1996). In contrast to CVF, rhC3-derivatives used for the present invention do not exhibit significant C5-cleaving activity. Accordingly, small to negligible amounts of C5a are generated upon action of complement with such rhC3-derivatives.

In a recent study, the rhC3-derivative HC3-1496 (designed as humanized CVF) in which the C-terminal 168 amino acid residues of the C3α-chain have been replaced with the corresponding 168 amino acid residues from the β-chain of CVF, has been injected into the arteria pulmonalis of cynomolgus monkeys to assess any potential acute lung damage or any other acute side effects (Fritzinger et al., 2008a). Upon injection of rhC3-derivative HC3-1496 at 250 μg/kg and even 1000 μg/kg multiple physiological lung parameters were not affected by the rapid complement depletion. Only at the very high dose of 1000 μg/kg a transient increase in the heart rate and systolic blood pressure was observed. Remarkable is the rapid removal of generated C3a from the circulation by carboxypeptidase N and the absence of any measurable C5a generation. Based on these data, complement activation by rhC3-derivatives used for the present invention is well tolerated and appears to be safe.

Only in individuals with a deficiency of carboxypeptidase N complement activation with rhC3-derivatives would be contra-indicated, but such a deficiency is extremely rare. Only two siblings with 21% of normal carboxypeptidase N activity and a single patient with 3% of normal carboxypeptidase N activity have been reported (Mathews et al., 1980; Willemse et al., 2008).

A potential limitation for repeated applications of rhC3-derivatives could be the immunogenicity of the CVF-portion of the derivatives. However, based on the high sequence identity of human complement component C3 with those rhC3-derivatives which are useful for the present invention (rhC3-derivative H5: 90%; rhC3-derivative H6: 96.3%; rhC3-derivative HC3-1496: 94%), the potential immunogenicity of these rhC3-derivatives in humans is expected to be very low or even negligible. Amino acid differences are limited to the very C-terminus of the α-chain. However, the CVF-specific residues are not contiguous but interspersed throughout the exchanged sequence. Furthermore, CVF and human C3 are structurally highly homologous. The exchanged region contains the C-terminal C345C domain which has the same three-dimensional structure in both CVF and human C3. In addition, the N-glycosides with immunogenic terminal galactosyl residues in CVF are absent in rhC3-derivatives expressed in insect or mammalian cells.

III. Controlled Complement Activation with rhC3-Derivatives

The therapeutic aim of the present invention is a controlled generation of activated complement components sufficient for significant augmentation of the immune response.

In one embodiment, a suitable rhC3-derivative is co-injected with one or more antigens (or antigenic extracts) adsorbed onto aluminium salts or onto another depot-mediating material. The quantity of the recombinant human C3 derivative in the composition is balanced in a way that upon injection a controlled activation of the complement system is induced providing a sufficient quantity of activated complement components and fragments thereof according to the therapeutic aims of the method of the present invention.

In another embodiment, the vaccination process includes repeated injections of a suitable rhC3-derivative at the site of antigen presentation. First, a recombinant human C3 derivative is co-injected with one or more antigens (or antigenic extracts) adsorbed onto aluminium salts or onto another depot-mediating material. The quantity of the recombinant human C3 derivative in the composition is balanced in a way that upon injection a controlled activation of the complement system is induced providing a sufficient quantity of activated complement components and fragments thereof according to the therapeutic aims of the method of the present invention. In one or more subsequent steps, the recombinant human C3 derivative is injected again at the site of antigen presentation. The quantity of the recombinant human C3 derivative in subsequent injections is balanced in a way that upon each injection sufficient activated complement components are generated.

In a more preferred embodiment, activated complement components are continuously generated at the site of antigen presentation. Since T cell differentiation and thus the development of immunologic memory requires the engagement of the T cell receptor (TCR) over 12-48 h and long lasting memory may even require repetitive exposure, both antigen and activated complement components preferably are present at least for the same period of time. The present invention discloses methods for a sustained generation of activated complement components at the site of antigen presentation without the need of repeated injections of recombinant human C3 derivatives along with a prolonged presentation of antigens.

To achieve sustained generation of activated complement components at the site of antigen presentation, the present invention discloses methods for a sustained release of recombinant human C3 derivatives from a depot at the site of antigen presentation. In a specific embodiment, the present invention discloses matrices for a sustained release of suitable rhC3-derivatives. Preferred matrices include but are not limited to biodegradable polymers which are suitable as depot for substantial quantities of recombinant human C3 derivatives, which allow the controlled release of recombinant human C3 derivatives over a prolonged period of time, and which are chemically and physically compatible with the recombinant human C3 derivatives and antigen(s) used for the vaccination process.

IV. Matrices for Sustained Delivery of rhC3-Derivatives

In a preferred embodiment, matrices are used for local delivery of suitable rhC3-derivatives that a) can serve as depot for substantial quantities of a suitable rhC3-derivative, b) allow the release of sufficient quantities of the embedded rhC3-derivative over a prolonged period of time (optimally for a few days), c) are biodegradable, and d) are chemically and physically compatible with the rhC3-derivative and antigen (s) used for the vaccination process according to the method of the present invention.

In one embodiment of the invention, biodegradable polymers are used for controlled delivery of suitable rhC3-derivatives. Preferred biodegradable polymers approved by FDA and used in a clinical trial, include but are not limited to poly(D,L-lactic acid), poly(lactic-co-glycolic acid) (PLGA), and copolymers of L-lactide and D,L-lactide. An important characteristic of such polymers is their ability to be applied locally. All FDA approved polymers have been studied extensively for their biocompatibility, toxicology, and degradation kinetics. Furthermore, these polymers have been shown to release embedded therapeutics for several hours up to 40 weeks in vitro and several weeks in vivo.

In a more preferred embodiment, injectable in situ-forming gel systems which are biodegradable, are used for controlled delivery of suitable rhC3-derivatives. Preferred in situ-forming gel systems (hydrogels) undergo a sol-gel-sol transition, which is a free flowing sol at room temperature and a non-flowing gel at body temperature. Compared to other biodegradable polymers, the injectable thermogelling polymers are possessing several advantages including easy preparation, high encapsulation efficiency of bioactive molecules including therapeutic proteins, and free of harmful organic solvents in the formulation process (Qiao et al. 2005).

In one specific embodiment, biodegradable thermogelling block polymers are used which are based on monomethoxy poly(ethylene glycol) (MPEG) including but not limited to a) diblock copolymers consisting of MPEG and poly(ε-caprolactone) (PCL) (Hyun et al., 2007), b) MPEG-b-(PCL-ran-PLLA) diblock copolymers (Kang et al., 2010), and c) diblock copolymers consisting of MPEG and PLGA (Peng et al., 2010). MPEG copolymers containing PCL provide the advantage that they do not create an acidic environment upon biodegradation in contrast to MPEG copolymers containing PLLA and PLGA (Hyun et al., 2007).

In another specific embodiment, biodegradable thermogelling triblock polymers are used including but not limited to a) PLGA-PEG-PLGA (Qiao et al., 2005), b) PEG-PLGA-PEG (Zhang et al., 2006), and c) PEG-PCL-PEG (PECE) (Gong et al., 2009a). Various biodegradable thermogelling triblock polymers made up of PLGA and PEG are disclosed in patent application WO 99/18142. At lower temperatures, hydrogen bonding between hydrophilic PEG segments of the copolymer chains and water molecules dominate in aqueous solutions, resulting in the dissolution of these copolymers in water. As the temperature increases, the hydrogen bonding becomes weaker, while hydrophobic forces of the hydrophobic segments such as PLGA segments are getting stronger, leading to sol-gel transition. PEG, PLGA and PCL are well-known FDA-approved biodegradable and biocompatible materials which have been widely used in the biomedical field.

In another specific embodiment, biodegradable thermogelling diblock and triblock copolymers are used which consist of polyethylene oxide (PEO) and a biodegradable polyester such as poly-L-lactic acid (PLLA) (Jeong et al., 1997). These block copolymers, however, are a free flowing sol at a higher temperature and form a gel at a lower temperature. For example, a 23% aqueous solution of PEO-PLLA-PEO ($M_r$ 5,000-2,040-5,000) is a sol at 45° C. and becomes a gel at 37° C. By changing the biodegradable block length, the sol-gel transition temperature can be manipulated, e.g., increasing the PLLA block length increases the aggregation tendency of a block copolymer in water, resulting in a steepening of the gel-sol transition curve slopes and the onset of gelation at lower concentrations. The sol-gel transition temperature is a function of concentration as well as composition of a block polymer.

In another specific embodiment, Poloxamers (trade name Pluronics) are used. Poloxamers are nonionic triblock copolymers composed of a central hydrophobic chain of polypropylene oxide) (PPO) flanked by two hydrophilic chains of poly (ethylene oxide) (PEO) (Gilbert et al., 1987). Poloxamers exhibit also sol-gel transition behavior in aqueous solutions and have been used for sustained delivery of several therapeutic agents. However, Poloxamers are not biodegradable and can be accumulated in the body which may lead to toxic side effects. Thus, the application of Poloxamers in biomedical fields has been greatly restricted. In a recent study, Pluronic F127 (100-unit PEO chain surrounding one 65-unit PPO) has been used to form composite thermosensitive hydrogels with PECE (Gong et al., 2009b). Based on the results of this study Pluronic F127/PECE composite hydrogels are biocompatible with low cell cytotoxicity and, therefore, may also be suitable for the method of the present invention.

The various biodegradable thermogelling polymers provide different stability characteristics. For example, Poloxamer triblock polymers provide excellent thermosensitivity, but due to weak hydrophobicity of the PPO block such copolymers form fast eroding gels which have been reported to persist in vivo a few hours at most. Exposure of Poloxamer gels to phosphate-buffered saline under in vitro conditions demonstrated gel erosion within 2 days (Hyun et al., 2007). Similar results were observed when the polymer solutions were subcutaneously injected into rats. Poloxamer gels could not be observed after 2 days (Hyun et al., 2007). Different results were obtained with MPEG-PCL gels. Under in vitro conditions MPEG-PCL gels maintained their structural integrity for more than 28 days and after subcutaneous injection into rats MPEG-PCL gels maintained their structural integrity longer than 30 days. The stability of MPEG-PCL gels, however, may also create problems since the rate of degradation of PCL in vivo is rather slow (2-3 years) compared to that of PLA, PGA or PLGA (for a review, see Sinha et al., 2004). Thus, after serving the function in delivering a suitable rhC3-derivative, MPEG-PCL copolymers may remain in the body under physiological conditions for an uncertain period. Therefore, most preferred biodegradable thermogelling polymers for the method of the present invention are those which maintain their structural integrity for a few days but do not remain in the body for more than a week.

In a preferred embodiment of the present invention, biodegradable thermogelling polymers are used which allow to modify their degradation kinetics. For example, PLLA segments can be incorporated into the PCL segment of MPEG-PCL copolymers, since PLLA provides better accessibility of water to the ester bonds of PLLA which enhances the hydrolytic degradation of the copolymer (Kang et al., 2010). The resulting MPEG-b-(PCL-ran-PLLA) diblock copolymers offer a therapeutic window that is adjustable from a few weeks to a few months by varying the amount of PLLA in the PCL segment (Kang et al., 2010). In another example, the rate of PLGA-PEG-PLGA hydrogel erosion can be modified by altering the molar ratio of DL-lactide/glycolide in the PLGA segment. The DL-lactide moiety is more hydrophobic than the glycolide moiety. Therefore, by increasing the molar ratio of DL-lactide/glycolide in the PLGA segment of PLGA-PEG-PLGA triblock copolymers, more stable hydrogels are formed due to stronger hydrophobic interactions among the copolymer molecules (Qiao et al. 2005).

Several of the biodegradable thermogelling polymers have been analyzed for their ability to mediate sustained release of proteins. Although different proteins such as rhC3-derivatives are likely to affect the release behavior of each copolymer in individual ways, characterization of the release of model proteins such as bovine serum albumin (BSA) provides important information. Using composite hydrogels containing different percentages of PECE and Pluronic F127, the in vitro release behavior of BSA proved to be dependent on the hydrogel composition, initial BSA loading amount, and hydrogel concentration (Gong et al., 2009b). Sustained release of BSA above 15 days was achieved with a composite hydrogel containing 60% PECE and 40% Pluronic F127, loaded with 4 mg BSA in the presence of 30 wt % hydrogel. Using MPEG-PCL copolymers, sustained in vitro release of BSA proved to be above 20 days, and under in vivo conditions (after subcutaneous injection into rats) sustained release lasted for more than 30 days (Hyun et al., 2007).

While for most clinical applications a sustained release of therapeutic drugs from biodegradable thermogelling polymers over a period of several weeks is desirable, the method of the present invention does not require such an extended sustained release of rhC3-derivatives since the development of immunologic memory requires the engagement of the T cell receptor (TCR) for a period of only 1 to 2 days. Therefore, preferred are biodegradable thermogelling polymers which deliver rhC3-derivatives for a limited period only which does not exceed a week.

PLGA-PEG-PLGA triblock copolymers represent one example of hydrogels providing advantageous degradation and release kinetics for the method of the present invention. As demonstrated in a recent study, the release of insulin from PLGA-PEG-PLGA triblock copolymers lasted for approximately 4 days with an initial burst effect during the first day (Choi et al, 2003). The initial burst effect may be advantageous for effective activation of complement in the initial phase of antigen presentation. However, the release kinetics may be modified by reducing the solubility of rhC3-derivatives via complexation with zink as shown for zink-insulin complexes (Choi et al, 2003).

Although Poloxamer gels are not biodegradable, Poloxamer 407 (trade name Pluronic F127) gels represent also an example of thermogelling polymers providing advantageous degradation and release kinetics for the method of the present invention. Although under in vitro conditions the release of BSA from Poloxamer 407 gels proved to be almost complete within 1 day, the sustained release of BSA under in vivo conditions (after subcutaneous injection into rats) lasted for 3 days (Hyun et al., 2007).

In still another embodiment, thermal-sensitive hydrogels formulated on the basis of trimethylated chitosan derivatives (Wu et al., 2012) are used for the sustained delivery of suitable rhC3-derivatives and one or more antigens. In addition to its application as a vaccine delivery system, the cationic polysaccharide has shown promising results as an adjuvant. For example, application of a chitosan solution for subcutaneous vaccination has been demonstrated to enhance both humoral and cell-mediated immune responses (Zaharoff et al., 2007). However, the unfavorable pH-dependent solubility and charge density of chitosan is a limiting factor. In contrast, trimethylated chitosan is well soluble in aqueous solution at neutral pH and provides excellent biocompatibility and mucoadhesive nature. Trimethylated chitosan derivatives are best characterized by the degree of quarternization, the degree of O-methylation and the degree of acetylation (Hagenaars et al., 2010).

Trimethylated chitosan derivatives are especially suited for nasal delivery of vaccines and are frequently formulated into particles or spray powder (Alhalaweh et al., 2009). Very recently, however, the trimethylated chitosan derivative N[(2-hydroxy-3-trimethylammonium) propyl] chitosan chloride has also been formulated together with α,β-glycerophosphate into a thermal-sensitive hydrogel (Wu et al., 2012). This hydrogel was shown a) to significantly prolong the antigen residence time in the nasal cavity, b) to enhance the transepithelial transport via the paracellular routes, and c) to induce in mice a high mucosal immunity (sIgA) and systemic immune response (IgG1 and IgG2a).

V. Safety Aspects of Drug Delivery by PEG/PLGA-Based Hydrogels

Preferred biodegradable polymers include but are not limited to poly(ethylene glycol) (PEG), poly(D,L-lactic acid), copolymers of L-lactic acid and D,L-lactic acid, poly(glycolic acid), and poly(lactic-co-glycolic acid) (PLGA). The use of these polymers as sustained-release protein delivery systems has been studied extensively (for a review, see Pai et al., 2009) and they represent the most compelling biodegradable polymers for depot systems due their inclusion in the FDA's General Recognized as Safe (GRAS) list for use in medical devices and drug formulations.

VI. Matrices for Sustained Antigen Presentation

The time of antigen exposure is extremely important since T cell differentiation and thus the development of immunologic memory requires the engagement of the T cell receptor (TCR) over 12-48 h and long lasting memory may even require repetitive exposure. Therefore, the present invention provides matrices suitable for a depot effect of adsorbed or embedded antigens that extends the lifetime of antigens and thus sustain antigen-stimulation of T cells.

In one preferred specific embodiment, aluminum-containing materials, typically aluminum phosphate or aluminum hydroxide gels (generally referred to as alum) are used to achieve prolonged antigen presentation since both aluminum phosphate and aluminum hydroxide are approved adjuvants in Europe and the USA. Upon incubation of proteinaceous antigens with aluminum-containing adjuvants, the antigens are partially or completely adsorbed onto the adjuvant via electrostatic interactions and exchange between phosphate and hydroxyl groups. Several studies have demonstrated that adsorption onto aluminum-containing adjuvants prevents rapid enzymatic degradation of the antigens, although the adsorption process may also induce structural changes potentially resulting in a decreased thermal stability (for a review, see Clapp et al., 2011).

Alum-adsorbed antigens are retained at specific sites in the body and only slowly released. This so-called depot effect is believed to be essential for a prolonged immune response. It should be mentioned, however, that several reports have shown rapid desorption of some proteinaceous antigens in vivo (HogenEsch, 2002), suggesting that the alum-mediated effect may be due to the release of concentrated antigen rather than a result of a strong depot effect. Other recent studies have even questioned the importance of antigen adsorption to aluminum-containing adjuvants for the immunological response (for a review, see Clapp et al., 2011). For example, the immune response elicited in rabbits against hen egg white lysozyme was irrespective of the fraction of antigen adsorbed onto the aluminum-containing adjuvant (Chang et al., 2001). For maximizing the immune response, however, some degree of adsorption or at least the proximity of the antigen and the adjuvant appears to be important. Apparently, alum keeps antigens in a particulate (rather than soluble) form, thereby enhancing phagocytosis of antigens by antigen presenting cells (APCs). Dendritic cells (DC) are capable of taking up both soluble antigens and antigens adsorbed onto alum.

Another effect of alum is the induction of a Th2 response including IL-4 and IL-5 production as well as IgG1 and IgE production by B cells (for a review, see Nicolls et al., 2010). Furthermore, alum can induce also maturation of monocytes/macrophages into DC-like cells. This process is dependent on the activation of NLRP3 (NOD-like receptor family, pyrin domain containing 3), part of the inflammasome which causes production of pro-inflammatory cytokines such as IL-1β and IL-18. It can be assumed that at least some of these adjuvancy activities of alum support the induction of immune responses initiated by activated complement components and fragments thereof.

In another preferred specific embodiment, antigens are embedded together with rhC3-derivatives in biodegradable polymers including biodegradable thermogelling polymers described in section V. Biodegradable polymers have the potential to provide both prolonged antigen presentation and a sustained release of rhC3-derivatives for a continuous generation of activated complement components. A recent study has demonstrated that soluble adjuvants such as rhC3-derivatives embedded together with antigens in biodegradable hydrogels may be potent compositions for eliciting immune responses. Using diblock copolymers consisting of MPEG-PLGA for hydrogel-codelivery of hepatitis B surface antigen (HBsAg) and GM-SCF, it was possible to elicit high HBsAg-specific antibodies and T-helper cell responses even in a mouse strain that does not respond to current HBsAg vaccine because of its H-2 haplotype (Chou et al., 2010).

In another embodiment, other depot-mediating materials (for reviews, see Petrowsky and Aguilar, 2004; Leroux-Roels, 2010; Nicholls et al., 2010) are employed for prolonged antigen presentation. Examples include, but are not limited to oil in water or water in oil emulsions (such as FIA, Montanide, Adjuvant 65 and Lipovant), liposomes, and polymeric microsphere adjuvants.

VII. Vaccine Compositions Comprising rhC3-Derivatives, One or More Antigens, and One or More Matrices Mediating Prolonged Delivery of rhC3-Derivative and Antigens In one embodiment, a suitable rhC3-derivative is co-injected with one or more antigens (or antigenic extracts) adsorbed onto aluminium salts or onto another depot-mediating material (see section V).

In another embodiment, the vaccination process includes repeated injections of a suitable rhC3-derivative at the site of antigen presentation.

In a more preferred embodiment, activated complement components are continuously generated at the site of antigen presentation along with a sustained presentation of antigens. Incorporation of a suitable rhC3-derivative into a fast degrading polymer provides sustained complement activation during antigen presentation.

In a preferred specific embodiment of the present invention, polymer-embedded rhC3-derivatives and one or more antigens (or antigenic extracts) partially or completely adsorbed onto alum or onto another depot-mediating material (see section V) are injected at the same location, but as separate preparations. After gellation of the polymer composit at the injection site, one or more antigens (or antigenic extracts) adsorbed onto alum or onto another depot-mediating material are injected in close proximity of the gelled polymer composit. The polymer composit comprises a biodegradable thermogelling polymer and a suitable rhC3-derivative, and is prepared by mixing all components at a temperature at which the biodegradable thermogelling polymer is a free flowing sol (e.g., at room temperature). The quantity of each component in the composition is balanced in a way that a) upon injection the biodegradable thermogelling polymer forms a non-flowing gel in which the other components are embedded, and b) upon gellation of the polymer composit at body temperature the amount of released rhC3-derivatives is sufficient for the therapeutic aims of the method of the present invention.

In another preferred specific embodiment of the present invention, the vaccine composition comprises a biodegradable thermogelling polymer containing one or more antigens (or antigenic extracts) partially or completely adsorbed onto alum or onto another depot-mediating material (see section V) and a suitable rhC3-derivative. The composition is prepared by mixing all components at a temperature at which the biodegradable thermogelling polymer is a free flowing sol (e.g., at room temperature). The quantity of each component in the composition is balanced in a way that a) upon injection the biodegradable thermogelling polymer forms a non-flowing gel in which the other components are embedded, and b) upon gellation of the polymer composit at body temperature the amount of released components is sufficient for the therapeutic aims of the method of the present invention.

In still another preferred specific embodiment of the present invention, the vaccine composition comprises a biodegradable thermogelling polymer containing one or more non-adsorbed antigens (or antigenic extracts) and a suitable rhC3-derivative. The composition is prepared by mixing all components at a temperature at which the biodegradable thermogelling polymer is a free flowing sol (e.g., at room temperature). The quantity of each component in the composition is balanced in a way that a) upon injection the biodegradable thermogelling polymer forms a non-flowing gel in which the other components are embedded, and b) upon gellation of the polymer composit at body temperature the amount of released components is sufficient for the therapeutic aims of the method of the present invention. Biodegradable polymers have the potential to provide both prolonged antigen presentation and the sustained release of a suitable rhC3-derivatives sufficient for the requirements of the method of the present invention. A recent study has demonstrated that soluble adjuvants such as rhC3-derivatives embedded together with antigens in biodegradable hydrogels are potent compositions for eliciting immune responses. Using diblock copolymers consisting of MPEG-PLGA for hydrogel-codelivery of hepatitis B surface antigen (HBsAg) and GM-SCF, it was possible to elicit high HBsAg-specific antibodies and T-helper cell responses even in a mouse strain that does not respond to current HBsAg vaccine because of its H-2 haplotype (Chou et al., 2010).

VIII. Hepatitis B Vaccination Using PLGA-PEG-PLGA Hydrogel-Delivered HbsAg and rhC3-Derivatives More than one third of the world's population has been infected with hepatitis B virus (HBV) and more than 150 million are chronic carriers, of whom 15-40% are at risk to develop HBV-associated liver diseases including cirrhosis and hepatocellular carcinoma (Ganem and Price, 2004). The main strategy for control of the infection and viral transmission is vaccination with the hepatitis B surface antigen (HbsAg). However, a small portion of normal vaccine recipients (approximately 5-10%) and a significant proportion of patients on maintenance hemodialysis with depressed immune responses (approximately 40-50%) do not respond adequately to current HbsAg vaccines.

Genetic studies have indicated a close association between different HLA-DR alleles and specific low responsiveness in different ethnic populations (Milich and Leroux-Roels, 2003). HLA-DR molecules are important for stimulating the activation and proliferation of CD4+ Th cells. This association is supported by the observation that peripheral blood mononuclear cells from HBV vaccine non-responders failed to proliferate in vitro upon exposure to HbsAg, whereas those from responders exhibited a strong proliferative response (e.g., Goncalves et al., 2004). Apparently, non-responsiveness to HbsAg vaccination is a result of an impaired Th cell response. Therefore, strategies capable of inducing a strong T cell proliferative response are needed.

The present invention provides methods for the induction of a strong T cell proliferative response to HbsAg vaccination using controlled activation of the human complement system as endogenous adjuvant. In a recent study, hydrogel-delivered GM-CSF has been shown to overcome non-responsiveness to hepatitis B vaccine through the recruitment and activation of dendritic cells (Chou et al., 2010), but the application of GM-CSF poses potential side effects such as the induction of histologically abnormal livers and spleens accompanied by an increased number of inflammatory cells (Lang et al., 1987; Burke et al., 2004). Application of rhC3-derivatives capable of activating the human complement component C3 provide a significant advantage for this approach since activated C3 fragments are known to induce strong immune responses but do not provoke potentially serious adverse side effects.

In a preferred specific embodiment, the present invention provides methods for hepatitis B vaccination using PLGA-PEG-PLGA hydrogel-delivered HbsAg and rhC3-derivatives. The composition is prepared by mixing all components at a temperature at which the biodegradable thermogelling polymer is a free flowing sol (e.g., at room temperature). The quantity of each component in the composition is balanced in a way that a) upon injection the biodegradable thermogelling polymer forms a non-flowing gel in which the other components are embedded, and b) upon gellation of the polymer composit at body temperature the amount of released components is sufficient for the therapeutic aims of the method of the present invention.

IX. Therapeutic Methods: Therapeutic Doses of rhC3-Derivatives

The determination of a therapeutically effective dose of a suitable rhC3-derivative necessary for generating a sufficient quantity of activated complement components and fragments thereof, depends on the characteristics of the administered rhC3-derivative and the kind of treatment. For example, repeated injections of rhC3-derivatives at the site of antigen presentation are likely to require a lower dose of rHC3-derivative per injection as compared to single injection regimens. Furthermore, sustained complement activation by hydrogel-mediated release of rhC3-derivatives may require incorporation of high doses of a suitable rhC3-derivative into the hydrogel due to potential conformational changes of rhC3-derivatives upon polymer incorporation resulting in a partial loss of activity. It is known that protein conformation is very sensitive to local environments and interfacial adsorption of polymer-embedded proteins has been found to limit the performance of sustained protein release from biodegradable depots as a result of impaired biological activity and reduced release from the polymer (for a review, see Pai et al., 2009).

However, the determination of a therapeutically effective dose is well within the capability of those skilled in the art. The therapeutically effective dose can be estimated initially in animal models, usually mice, rats, rabbits, dogs, pigs, or non-human primates. The animal model also can be used to determine the appropriate concentration range and route of administration. Such information can then be used to determine useful doses and routes for administration in humans.

Several animal studies performed in the recent past with rhC3-derivative HC3-1496 have provided useful data which allow to correlate the quantity of injected rhC3-derivative and the route and the number of injections with the degree of complement activation resulting in the depletion of complement components (for a review, see Vogel and Fritzinger, 2010). Furthermore, these studies provide also information about the time required for re-synthesis of depleted complement components.

Injection of HC3-1496 into the pulmonary artery of cynomolgus monkeys over a period of 1-5 min at 250 µg/kg or 1000 µg/kg resulted in complete depletion of complement within 5 min (approximately 20% residual haemolytical activity) and remained depleted for at least 1 h, followed by a gradual increase to approximately 50% activity over the next 6 h (Fritzinger et al., 2008a, Vogel and Fritzinger, 2010). No reduction of serum complement was observed with 62.5 µg/kg of HC3-1496.

Intraperitoneal injection of HC3-1496 into adult Sprague-Dawley rats at 280 µg/kg or 760 µg/kg resulted in complete depletion of complement (approximately 5% residual activity) and remained depleted for at least 4 h, followed by a gradual increase to approximately 50% over the next 20 h (Fritzinger et al., 2008b, Vogel and Fritzinger, 2010).

Intraperitoneal injection of biotinylated HC3-1496 into mice at 500 µg/kg resulted in complete depletion of complement (less than 5% residual activity) and remained depleted for at least 4 h, followed by a gradual increase to approximately 80% over the next 6 h (Vogel and Fritzinger, 2010).

In a murine model of collagen-induced arthritis, complement depletion was maintained for two or three weeks by an initial intraperitoneal injection of HC3-1496 at 500 µg/kg, followed by a maintenance dose of 250 µg/kg on 5 days/week (Fritzinger et al., 2008b, Vogel and Fritzinger, 2010).

In a murine model of age-related macular degeneration intraperitoneal injection of HC3-1496 at a very low dose of 25 µg/kg for 28 days resulted in an average reduction of about 30% complement haemolytic activity on day 28, with significant animal to animal variation (Fritzinger et al., 2008b, Vogel and Fritzinger, 2010).

X. Therapeutic Methods: Routes of Administration

Preferred examples of routes of administration include but are not limited to intradermal, subcutaneous, and intramuscular administrations. Dosage regimens may be adjusted to provide the optimum therapeutic response.

In one preferred specific embodiment of the present invention, a biodegradable thermogelling polymer solution containing rhC3-derivatives and one or more antigens (or antigenic extracts) non-adsorbed or partially or completely adsorbed onto alum or onto another depot-mediating material (see section V) is injected subcutaneously. The quantity of the polymer-embedded components depends on the release kinetics of the biodegradable thermogelling polymer and is adjusted to a level that guarantees the continuous release of therapeutically effective doses over a period of 3 to 5 days. The quantity of embedded components will vary according to factors such as the weight and the age of the individual, and the ability of the composition to induce an effective immune response in the individual.

Since the mucosa is a door of entry for many pathogens, mucosal immunization represents another preferred embodiment of the present invention. Different results can be obtained for the same antigen and adjuvant when administered by a parenteral or mucosal route. For example, it is very difficult to generate mucosal antibodies through parenteral vaccination, while it is possible to obtain mucosal as well as parenteral immunity by inoculating antigen by the mucosal route (Bye et al., 1984). For pathogens colonizing mucosal surfaces or those having a mucosal route of entry, protection correlates well with a strong local mucosal response.

For mucosal immunization, however, the physicochemical characteristics of the antigen, the adjuvant, and the delivery vehicle have to be adjusted to stimulate their uptake through the various mucosal routes. For example, alum salts are ineffective when administered by the oral or nasal route. In contrast, cationic chitosan derivatives are of special interest in nasal delivery because of their excellent biocompatibility and mucoadhesive nature (Hagenaars et al., 2010). For example, a thermal-sensitive hydrogel which was formulated as intranasal vaccine with N[(2-hydroxy-3-trimethylammonium)propyl] chitosan chloride (HTCC) and $\alpha,\beta$-glycerophosphate, was shown to significantly prolong the antigen residence time in the nasal cavity and to enhance the transepithelial transport via the paracellular routes (Wu et al., 2012). This mucosal delivery system induced in mice a high mucosal immunity (sIgA) and systemic immune response (IgG1 and IgG2a).

In another preferred specific embodiment of the present invention, a thermo-sensitive polymer solution formulated on the basis of cationic chitosan derivatives, which contains rhC3-derivatives and one or more antigens (or antigenic extracts) is administered intranasally. The quantity of the polymer-embedded components depends on the release kinetics of the thermogelling polymer and is adjusted to a level that guarantees the continuous release of the embedded components at therapeutically effective doses over a prolonged period of time. The quantity of embedded components will vary according to factors such as age of the individual and the ability of the composition to induce an effective immune response in the individual.

XI. Pharmaceutical Formulations

In one embodiment, the vaccine compositions are incorporated into pharmaceutical compositions suitable for administration. Such compositions typically comprise the vaccine composition and a pharmaceutically acceptable carrier. As used herein, a 'pharmaceutically acceptable carrier' is intended to include any and all solvents, dispersion media, coatings, antibacterial and antifungal agents, isotonic systems, and the like, compatible with the components of the vaccine composition and pharmaceutical administration. The use of such media and agents for pharmaceutically active substances is well known in the art. Supplementary active compounds can also be incorporated into the composition.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents, antioxidants such as ascorbic acid or sodium bisulfite, chelating agents such as ethylenediaminetetraacetic acid, buffers such as acetates, citrates or phosphates and agents for the adjustment of toxicity such as sodium chloride or dextrose. The pH can be adjusted with acids or bases, such as hydrochloric acid or sodium hydroxide. In many cases, it will be preferable to include isotonic agents, for example, sugars, polyalcohols such as mannitol, sorbitol, sodium chloride in the composition. The composition should be fluid to the extent that easy syringability exists. The proper fluidity can be maintained, for example, by the use of a coating such as lecithin, by the maintenance of the required particle size in the case dispersion and by use of surfactants. The composition must be stable under the conditions of manufacture and storage and must be preserved against the contaminating action of microorganisms such as bacteria and fungi. Prevention of the action of microorganisms can be achieved by various antibacterial and antifungal agents such as parabens, chlorobutanol, phenol, ascorbic acid, thimoseral, and the like. In all cases, the composition must be sterile. Sterile injectable solutions can be prepared by filtered sterilization. The preparation can be enclosed in ampoules, disposable syringes or multiple dose vials made of glass or plastic. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. For practical purposes it should be kept in mind that aluminum-adsorbed vaccines are frost sensitive and therefore not lyophilizable.

XII. Fields of Application

The vaccine compositions of the present invention comprising rhC3-derivatives and one or more antigens (including antigenic extracts), can be used to induce immune responses against any antigen in any mammalian organism.

In one preferred embodiment, the vaccine compositions of the present invention comprising rhC3-derivatives and one or more antigens (including antigenic extracts), are used to induce immune responses in mammals, preferably in humans, against infectious agents including, but not limited to bacterial, viral and fungal agents.

In another preferred embodiment, the vaccine compositions of the present invention comprising rhC3-derivatives and one or more antigens (including antigenic extracts), are used to induce immune responses in mammals, preferably in humans, against antigens expressed by mammalian neoplastic cells.

In another preferred embodiment, the vaccine compositions of the present invention comprising rhC3-derivatives and one or more antigens (including antigenic extracts), are used to induce immune response in mammals, preferably in humans, against mammalian antigens associated with inflammatory diseases including, but not limited to autoimmune diseases, allergic diseases and inflammatory dermatological diseases.

XIII. Definitions

"Inflammatory diseases" include but are not limited to Acne Vulgaris, Asthma, Celiac Disease, Chronic Prostatitis, Glomerulonephritis, Hypersensitivities, Inflammatory Bowel Diseases, Pelvic Inflammatory Disease, Reperfusion Injury, Rheumatoid Arthritis, Sarcoidosis, Transplant Rejection, Vasculitis, Interstitial cystitis, in particular autoimmune diseases, including but no limited to Alopecia areata, Autoimmuneenteropathie, Autoimmunehepatitis, APECED, Bullous Pemphigoid, Chronic Gastritis, Churg-Strauss-Syndrome, CIDP, Colitis ulcerosa, Dermatomyositis, Diabetes mellitus Type 1, Dermatitis herpetiformis, Epidermolysis bullosa acquisita, Glomerulonephritis, Goodpasture-Syndrome, Guillain-Barré-Syndrome, Hashimoto-Thyreoiditis, Lichen sclerosus, Linear IgA-Dermatosis, Lupus erythematodes, Microscopic Polyangiitis, Morbus Adamantiades-Behçet, Morbus Basedow, Morbus Bechterew, Iris Morbus Crohn, Multiple Sklerosis, Myasthenia gravis, Narkolepsie, PANDAS, Pemphigus foliaceus, Pemphigus seborrhoicus, Pemphigus vulgaris, Polychondritis, Polymyalgia rheumatica, Polymyositis, Psoriasis, Rheumatic Fever, Rheumatic Arthritis, SAPHO-Syndrom, Sarkoidose (Morbus Boeck), Sjögren-Syndrome, Sklerodermie, Stiff-Man-Syndrome, Sympathic Ophthalmie, Systemic Lupus erythematodes, Purpura Schönlein-Henoch, Vitiligo, Wegener's Granulomatose, Zöliakie, Sepsis.

"Allergic diseases" include but are not limited to diseases triggered by exposure to proteins as identified in the Allergome project (www.allergome.org), IgE reactive allergens, contact allergens, inhalative allergens, injection allergens (insects), including diseases like Allergic Rhinitis, Asthma Bronciale, Conjunctivitis, Atopic Dermatitis, Urticaria, Anaphylactic Shock, vomiting and/or diarrhea upon exposure to an allergen.

Diseases related with "mammalian neoplastic cells" include but are not limited to Bladder Cancer, Lung Cancer, Breast Cancer, Melanoma, Colon and Rectal Cancer, Non-Hodgkin Lymphoma, Endometrial Cancer, Pancreatic Cancer, Kidney (Renal Cell) Cancer, Prostate Cancer, Leukemia, and Thyroid Cancer.

Diseases related with "infectious agents" include but are not limited to *Acinetobacter* infections, Actinomycosis, African sleeping sickness (African trypanosomiasis), AIDS (Acquired immunodeficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis (BV), *Bacteroides* infection, Balantidiasis, *Baylisascaris* infection, BK virus infection, Black *piedra, Blastocystis hominis* infection, Blastomycosis, Bolivian hemorrhagic fever, *Borrelia* infection, Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Chagas Disease (American trypanosomiasis), Chancroid, Chickenpox, *Chlamydia, Chlamydophila pneumoniae* infection, Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolopsiasis, Fasciolosis, Filariasis, Gas gangrene, Giardiasis, Glanders, Gonorrhea, Granuloma inguinale (Donovanosis), Group A streptococcal infection, Group B streptococcal infection, *Haemophilus influenzae* infection, Hand, foot and mouth disease (HFMD), Pulmonary Syndrome (HPS), *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human *ewingii* ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious (Mononucleosis), Influenza (flu), Isosporiasis, Keratitis, *Kingella kingae* infection, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Melioidosis (Whitmore's disease), Meningitis, Meningococcal disease, Metagonimiasis, Microsporidiosis, Molluscum contagiosum (MC), Mumps, Murine typhus (Endemic typhus), *Mycoplasma* pneumonia, Mycetoma, Myiasis, Neonatal conjunctivitis (Ophthalmia neonatorum), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever (RVF), Rocky mountain spotted fever (RMSF), Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea *versicolor* (*Pityriasis versicolor*), Toxocariasis (Ocular Larva Migrans (OLM)), Toxocariasis (Visceral Larva Migrans (VLM)), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White *piedra* (Tinea blanca), *Yersinia pseudotuberculosis* infection, Yersiniosis, Yellow fever. Many other diseases are associated with infectious agents, among others (and some of those mentioned above in other context) for example Alzheimer's Disease, Amyotrophic Lateral Sclerosis, Anorexia Nervosa, Anxiety Disorder, Asthma, Atherosclerosis, Attention Deficit Hyperactivity Disorder, Autism, Bipolar Disorder, Chronic fatigue Syndrome, Chronic Obstructive pulmonary Disease, Crohn's Disease, Coronary Heart Disease, Dementia, Depression, Diabetes Mellitus Type I and II, Dilates Cardiomyopathy, Epilepsy, Lupus, Metabolic Syndrome, Multiple Sclerosis, Myocardial Infarctation, Obesity, Obsessive-Compulsive Disorder, Panic Disorder, Parkinson's Disease, Sarcoidosis, Schizophrenia, Stroke, Thromboangiitis Obliterans, Tourette Syndrome, Vasculitis.

Specific antigenes of compounds, cells or organisms related with said diseases are published in the scientific literature and are easily identified by a person skilled in the art.

Figure 2:
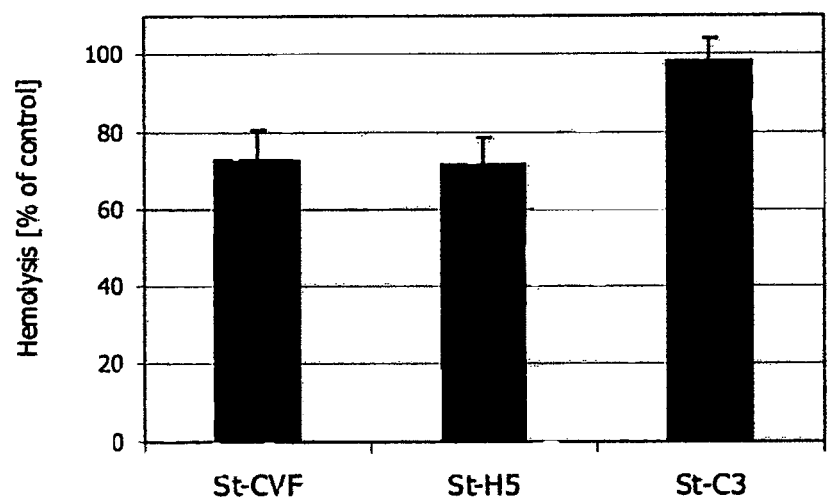

The phrase "recombinant C3-derivative" includes a polypeptide or protein having a length of 1276 to 1663 amino acids, which is a derivative of human complement component C3 (human C3), the amino acid sequence of which is shown in SEQ ID NO:2 of U.S. Pat. No. 8,119,769, wherein the carboxy terminal part of at least 68 amino acid residues of human C3 is replaced by a partial sequence of Cobra Venom Factor (CVF), the amino acid sequence of which is shown in SEQ ID NO:4 of U.S. Pat. No. 8,119,769, which partial sequence comprises at least the 68 carboxy terminal amino acid residues of CVF or a fragment thereof lacking 1 to 25 carboxy terminal amino acids, wherein said protein has at least 70% identity to human C3. Thus, the invention utilizes a protein comprising a derivative of human complement component C3 (human C3), the human C3 having an amino acid sequence set forth as SEQ ID NO: 2 of U.S. Pat. No. 8,119,769, wherein the carboxy terminal part of at least 68 amino acids of said human C3 is replaced by a partial sequence of Cobra Venom Factor (CVF), the CVF having an amino acid sequence set forth as SEQ ID NO: 4 of U.S. Pat. No. 8,119,769, wherein the partial sequence of CVF comprises at least at least 68 carboxy terminal amino acids of CVF or a fragment thereof, said fragment lacking 1 to 25 carboxy terminal amino acids, and wherein said protein has at least 70 percent identity to said human C3. An alignment of the C3 and CVF sequences is shown in FIG. 1 of U.S. Pat. No. 8,119,769. In addition, without departing from the spirit of the invention, it may be desired for specific purposes, however, to attach additional non-C3 and non-CVF amino acids to the carboxy terminus of the hybrid proteins. Decomplementing activity of C3/CVF hybrid proteins is observed with polypeptides where the C3 alpha-chain is replaced by the corresponding carboxy terminal amino acids of the CVF chain (including the gamma- and the beta-chain of CVF). This construct has a length of 1276 amino acids as processed protein (SEQ ID NO:1 of the instant application). However, due to the immunogenicity of such polypeptides, a higher degree of humanization is preferred. Thus, according to a preferred embodiment, the polypeptides comprise an amino terminal C3 fragment containing the amino acids forming the beta-chain (amino acids 23 to 667 of SEQ ID NO:2 of U.S. Pat. No. 8,119,769) as well as additional amino acids of the C3 chain following at the carboxy terminal end of the beta-chain, i.e. from amino acid 668 towards the carboxy terminus of the peptide. At least 68 amino acids of the C3 sequence are replaced by amino acids of the corresponding CVF sequence. Reference is made in this respect to FIG. 1 of U.S. Pat. No. 8,119,769, showing the alignment of the C3 and CVF sequences. The requirement that the amino acid sequence of the polypeptides of the invention have at least 70% identity to the amino acid sequence of human C3 is intended to ensure that immunogenicity of the hybrid proteins is kept at a tolerable level. The 70% value thus also determines the minimum sequence stretch of the C3 sequence which is required for being combined with the amino acids of the CVF sequence which replace the corresponding carboxy terminal C3 amino acids. It is preferred to provide polypeptides where the identity with the human C3 sequence is at least 80%, or more preferably at least 90% and most preferably at least 95%. According to a preferred embodiment of the invention, the protein or polypeptide, which is a derivative of human complement component C3 (human C3), has an amino acid sequence, which is selected from the group consisting of: a) the sequence shown in SEQ ID NO:6 (which is shown in SEQ ID NO:6 of U.S. Pat. No. 8,119,769); b) the sequence shown in SEQ ID NO:8 (which is shown in SEQ ID NO:8 of U.S. Pat. No. 8,119,769); c) the sequence shown in SEQ ID NO:10 (which is shown in SEQ ID NO:10 of U.S. Pat. No. 8,119,769); and d) the sequence shown in SEQ ID NO:12 which is shown in SEQ ID NO:12 of U.S. Pat. No. 8,119,769. The most preferred constructs represented by SEQ ID NO:6 and SEQ ID NO:8 of U.S. Pat. No. 8,119,769 and the identity of the amino acid sequences with human C3 amino acid sequence is approx. 90.7% (91%) for SEQ ID NO:6, and 96.3% (96%) for SEQ ID NO:8, respectively. Reference is made in this regard to FIG. 2 of U.S. Pat. No. 8,119,769. After appropriate processing upon recombinant expression, constructs H6 and H5 (represented by SEQ ID NO:6 of U.S. Pat. No. 8,119,769 and SEQ ID NO:8 of U.S. Pat. No. 8,119,769) have both a length of 1637 amino acids (processed H6 construct: SEQ ID NO:2 of the instant specification; processed H5 construct: SEQ ID NO:3 of the instant specification). SEQ ID NOs: 2, 4, 6, 8, 10 and 12 of U.S. Pat. No. 8,119,769 are hereby incorporated by reference.

SEQ ID NO: 1

Length: 1276

Type: PRT

Organism: Artificial sequence

Feature:

Other Information: Processed hybrid protein comprising the C3 beta-chain and the gamma- and beta-chain of CVF

SPMYSIITPNILRLESEETMVLEAHDAQGDVPVTVTVHDFPGKKLVLSSEKTVLTPAT

NHMGNVTFTIPANREFKSEKGRNKFVTVQATFGTQVVEKVVLVSLQSGYLFIQTDKT

IYTPGSTVLYRIFTVNHKLLPVGRTVMVNIENPEGIPVKQDSLSSQNQLGVLPLSWDIP

ELVNMGQWKIRAYYENSPQQVFSTEFEVKEYVLPSFEVIVEPTEKFYYIYNEKGLEVT

ITARFLYGKKVEGTAFVIFGIQDGEQRISLPESLKRIPIEDGSGEVVLSRKVLLDGVQNP

RAEDLVGKSLYVSATVILHSGSDMVQAERSGIPIVTSPYQIHFTKTPKYFKPGMPFDL

MVFVTNPDGSPAYRVPVAVQGEDTVQSLTQGDGVAKLSINTHPSQKPLSITVRTKKQ

ELSEAEQATRTMQALPYSTVGNSNNYLHLSVLRTELRPGETLNVNFLLRMDRAHEA

KIRYYTYLIMNKGRLLKAGRQVREPGQDLVVLPLSITTDFIPSFRLVAYYTLIGASGQR

EVVADSVWVDVKDSCVGSLVVKSGQSEDRQPVPGQQMTLKIEGDHGARVVLVAVD

-continued

```
KGVFVLNKKNKLTQSKIWDVVEKADIGCTPGSGKDYAGVFSDAGLTFTSSSGQQTA

QRAELQCPQPAADDNEDGFIADSDIISRSDFPKSWLWLTKDLTEEPNSQGISSKTMSFY

LRDSITTWVVLAVSFTPTKGICVAEPYEIRVMKVFFIDLQMPYSVVKNEQVEIRAILHN

YVNEDIYVRVELLYNPAFCSASTKGQRYRQQFPIKALSSRAVPFVIVPLEQGLHDVEI

KASVQEALWSDGVRKKLKVVPEGVQKSIVTIVKLDPRAKGVGGTQLEVIKARKLDD

RVPDTEIETKIIIQGDPVAQIIENSIDGSKLNEIQMPTHKDLNLDITIELPDREVPIRYRIN

YENALLARTVETKLNQDITVTASGDGKATMTILTFYNAQLQEKANVCNKFHLNVSV

ENIHLNAMGAKGALMLKICTRYLGEVDSTMTIIDISMLTGFLPDAEDLTRLSKGVDRY

ISRYEVDNNMAQKVAVIIYLNKVSHSEDECLHFKILKHFEVGFIQPGSVKVYSYYNLD

EKCTKFYHPDKGTGLLNKICIGNVCRCAGETCSSLNHQERIDVPLQIEKACETNVDYV

YKTKLLRIEEQDGNDIYVMDVLEVIKQGTDENPRAKTHQYISQRKCQEALNLKVNDD

YLIWGSRSDLLPTKDKISYIITKNTWIERWPHEDECQEEEFQKLCDDFAQFSYTLTEFG

CPT
```

SEQ ID NO: 2

| | |
|---|---|
| Length: | 1637 |
| Type: | PRT |
| Organism: | Artificial sequence |
| Feature: | |
| Other Information: | Processed H6 construct |

```
SPMYSIITPNILRLESEETMVLEAHDAQGDVPVTVTVHDFPGKKLVLSSEKTVLTPAT

NHMGNVTFTIPANREFKSEKGRNKFVTVQATFGTQVVEKVVLVSLQSGYLFIQTDKT

IYTPGSTVLYRIFTVNHKLLPVGRTVMVNIENPEGIPVKQDSLSSQNQLGVLPLSWDIP

ELVNMGQWKIRAYYENSPQQVFSTEFEVKEYVLPSFEVIVEPTEKFYYIYNEKGLEVT

ITARFLYGKKVEGTAFVIFGIQDGEQRISLPESLKRIPIEDGSGEVVLSRKVLLDGVQNL

RAEDLVGKSLYVSATVILHSGSDMVQAERSGIPIVTSPYQIHFTKTPKYFKPGMPFDL

MVFVTNPDGSPAYRVPVAVQGEDTVQSLTQGDGVAKLSINTHPSQKPLSITVRTKKQ

ELSEAEQATRTMQALPYSTVGNSNNYLHLSVLRTELRPGETLNVNFLLRMDRAHEA

KIRYYTYLIMNKGRLLKAGRQVREPGQDLVVLPLSITTDFIPSFRLVAYYTLIGASGQR

EVVADSVWVDVKDSCVGSLVVKSGQSEDRQPVPGQQMTLKIEGDHGARVVLVAVD

KGVFVLNKKNKLTQSKIWDVVEKADIGCTPGSGKDYAGVFSDAGLTFTSSSGQQTA

QRAELQCPQPAASVQLTEKRMDKVGKYPKELRKCCEDGMRENPMRFSCQRRTRFIS

LGEACKKVFLDCCNYITELRRQHARASHLGLARSNLDEDIIAEENIVSRSEFPESWLW

NVEDLKEPPKNGISTKLMNIFLKDSITTWEILAVSMSDKKGICVADPFEVTVMQDFFID

LRLPYSVVRNEQVEIRAVLYNYRQNQELKVRVELLHNPAFCSLATTKRRHQQTVTIP

PKSSLSVPYVIVPLKTGLQEVEVKAAVYHHFISDGVRKSLKVVPEGIRMNKTVAVRT

LDPERLGREGVQKEDIPPADLSDQVPDTESETRILLQGTPVAQMTEDAVDAERLKHLI

VTPSGCGEQNMIGMTPTVIAVHYLDETEQWEKFGLEKRQGALELIKKGYTQQLAFRQ

PSSAFAAFVKRAPSTWLTAYVVKVFSLAVNLIAIDSQVLCGAVKWLILEKQKPDGVF

QEDAPVIHQEMIGGLRNNNEKDMALTAFVLISLQEAKDICEEQVNSLPGSITKAGDFL

EANYMNLQRSYTVAIAGYALAQMGRLKGPLLNKFLTTAKDKNRWEDPGKQLYNVE

ATSYALLALLQLKDFDFVPPVVRWLNEQRYYGGGYGSTQATFMVFQALAQYQKDA
```

-continued

PDHQELNLDVSLQLPSRSSKITHRIHWESASLLRSEETKENEGFTVTAEGKGQGTLSV

VTMYHAKAKDQLTCNKFDLKVTIKPAPETEKRPQDAKNTMILEICTRYRGDQDATM

SILDISMMTGFAPDTDDLKQLANGVDRYISKYELDKAFSDRNTLIIYLDKVSHSEDDC

LAFKVHQYFNVELIQPGAVKVYAYYNLEESCTRFYHPEKEDGKLNKLCRDELCRCA

EENCFIQKSDDKVTLEERLDKACEPGVDYVYKTKLLRIEEQDGNDIYVMDVLEVIKQ

GTDENPRAKTHQYISQRKCQEALNLKVNDDYLIWGSRSDLLPTKDKISYIITKNTWIE

RWPHEDECQEEEFQKLCDDFAQFSYTLTEFGCPT

SEQ ID NO: 3

Length: 1637

Type: PRT

Organism: Artificial sequence

Feature:

Other Information: Processed H5 construct

SPMYSIITPNILRLESEETMVLEAHDAQGDVPVTVTVHDFPGKKLVLSSEKTVLTPAT

NHMGNVTFTIPANREFKSEKGRNKFVTVQATFGTQVVEKVVLVSLQSGYLFIQTDKT

IYTPGSTVLYRIFTVNHKLLPVGRTVMVNIENPEGIPVKQDSLSSQNQLGVLPLSWDIP

ELVNMGQWKIRAYYENSPQQVFSTEFEVKEYVLPSFEVIVEPTEKFYYIYNEKGLEVT

ITARFLYGKKVEGTAFVIFGIQDGEQRISLPESLKRIPIEDGSGEVVLSRKVLLDGVQNL

RAEDLVGKSLYVSATVILHSGSDMVQAERSGIPIVTSPYQIHFTKTPKYFKPGMPFDL

MVFVTNPDGSPAYRVPVAVQGEDTVQSLTQGDGVAKLSINTHPSQKPLSITVRTKKQ

ELSEAEQATRTMQALPYSTVGNSNNYLHLSVLRTELRPGETLNVNFLLRMDRAHEA

KIRYYTYLIMNKGRLLKAGRQVREPGQDLVVLPLSITTDFIPSFRLVAYYTLIGASGQR

EVVADSVWVDVKDSCVGSLVVKSGQSEDRQPVPGQQMTLKIEGDHGARVVLVAVD

KGVFVLNKKNKLTQSKIWDVVEKADIGCTPGSGKDYAGVFSDAGLTFTSSSGQQTA

QRAELQCPQPAASVQLTEKRMDKVGKYPKELRKCCEDGMRENPMRFSCQRRTRFIS

LGEACKKVFLDCCNYITELRRQHARASHLGLARSNLDEDIIAEENIVSRSEFPESWLW

NVEDLKEPPKNGISTKLMNIFLKDSITTWEILAVSMSDKKGICVADPFEVTVMQDFFID

LRLPYSVVRNEQVEIRAVLYNYRQNQELKVRVELLHNPAFCSLATTKRRHQQTVTIP

PKSSLSVPYVIVPLKTGLQEVEVKAAVYHHFISDGVRKSLKVVPEGIRMNKTVAVRT

LDPERLGREGVQKEDIPPADLSDQVPDTESETRILLQGTPVAQMTEDAVDAERLKHLI

VTPSGCGEQNMIGMTPTVIAVHYLDETEQWEKFGLEKRQGALELIKKGYTQQLAFRQ

PSSAFAAFVKRAPSTWLTAYVVKVFSLAVNLIAIDSQVLCGAVKWLILEKQKPDGVF

QEDAPVIHQEMIGGLRNNNEKDMALTAFVLISLQEAKDICEEQVNSLPGSITKAGDFL

EANYMNLQRSYTVAIAGYALAQMGRLKGPLLNKFLTTAKDKNRWEDPGKQLYNVE

ATSYALLALLQLKDFDFVPPVVRWLNEQRYYGGGYGSTQATFMVFQALAQYQKDA

PDHQELNLDVSLQLPSRSSKITHRIHWESASLLRSEETKENEGFTVTAEGKGQGTLSV

VTMYHAKAKDQLTCNKFDLKVTIKPAPETEKRPQDAKNTMILEICTRYLGEVDSTMT

IIDISMLTGFLPDAEDLTRLSKGVDRYISRYEVDNNMAQKVAVIIYLNKVSHSEDECL

HFKILKHFEVGFIQPGSVKVYSYYNLDEKCTKFYHPDKGTGLLNKICIGNVCRCAGET

CSSLNHQERIDVPLQIEKACETNVDYVYKTKLLRIEEQDGNDIYVMDVLEVIKQGTDE

-continued
NPRAKTHQYISQRKCQEALNLKVNDDYLIWGSRSDLLPTKDKISYIITKNTWIERWPH

EDECQEEEFQKLCDDFAQFSYTLTEFGCPT

The phrase "sequence identity" refers to the BLAST® program provided for sequence searching in a published version online on Jun. 11, 2012.

A "stable" convertase has an extended half-life of its decay-dissociation that is by at least 10%, better at least 100%, more stable than the human C-3 convertase, measured as evident from the Examples provided hereinafter.

"Little or negligible C5-cleaving activity" is preferably an activity of less than 50%, better of less than 20%, than that of the human C-3 convertase, measured as evident from the Examples provided hereinafter.

XIV: Preferred Treatment Methods

In a method of the invention for the induction of immune responses in mammals, preferably in humans, a composition according to the invention is administered in a therapeutically effective dose, wherein a recombinant human C3 derivative of the invention is co-injected or co-implanted with one or more antigens adsorbed onto a matrix of the invention, preferably onto aluminium salts, followed by one or more additional injections or implantations of a recombinant human C3– derivative of the invention at the site of antigen presentation to effect sustained activation of complement during the period of antigen presentation.

In a further method of the invention for the induction of immune responses in mammals, preferably in humans, a composition according to the invention is administered in a therapeutically effective dose, wherein a recombinant human C3-derivative of the invention is coated or absorbed or embedded in a matrix according to claim of the invention, preferably embedded in a biodegradable thermogelling hydrogel of the invention, and wherein the composit of matrix and recombinant human C3-derivative is injected or implanted at or in proximity of the infection or implantation site of one or more antigens adsorbed onto a matrix of the invention, preferably onto aluminium salts.

In a further method for the induction of immune responses in mammals, preferably in humans, a composition of the invention is administered in a therapeutically effective dose, wherein one or more antigens and a recombinant human C3-derivative of the invention are coated or absorbed or embedded in a matrix of the invention, preferably embedded in a biodegradable thermogelling hydrogel of the invention, and wherein the composit of matrix, recombinant human C3-derivative and one or more antigens is injected or implanted.

In a further method of the invention for the induction of immune responses in mammals, preferably in humans, a composition of the invention is administered in a therapeutically effective dose, wherein one or more antigens adsorbed onto a matrix of the invention, preferably onto aluminium salts, and a recombinant human C3-derivative of the invention are coated or adsorbed or embedded in a matrix of the invention, preferably embedded in a biodegradable thermogelling hydrogel of the invention, and wherein the composit of matrix, recombinant human C3-derivative and one or more adsorbed antigens is injected or implanted.

In a further method of the invention for the induction of immune responses in mammals, preferably in humans, a composition of the invention is repeatedly administered in a therapeutically effective dose, wherein one of the methods provided hereinabove is repeated once or more than once within an appropriate period of time to booster the immune response.

LITERATURE

Ahearn et al. (1996) Immunity 4: 251-262.
Akira and Takeda (2004) Nat. Rev. Immunol. 4: 499-511.
Alhalaweh et al. (2009) Eur. J. Pharm. Sci. 38: 206-214.
Alper et al. (1969) Science 163: 286-288.
Andra et al. (2002) Mol. Immunol. 39: 357-365.
Ballow and Cochrane (1969) J. Immunol. 103: 944-952.
Bohnsack and Cooper (1988) J. Immunol. 141: 2569-2576.
Böttger et al. (1985). J. Immunol. 135: 4100-4107.
Böttger et al. (1986) J. Immunol. 137: 1280-1285.
Burke et al. (2004) Clin. Diag. Lab. Immunol. 11: 588-598.
Bye et al. (1984) Gastroenterology 86: 789-801.
Carroll (2004). Nat. Immunol. 5: 981-986.
Chang et al. (2001) Vaccine 19: 2884-2889.
Choi et al. (2003) Pharmaceut. Res. 20: 2008-2010.
Chou et al. (2010) J. Immunol. 185: 5468-5475.
Chow et al. (1998) J. Immunol. 160: 1320-1329.
Clapp et al. (2011) J. Pharm. Sci. 100: 388-401.
Cochrane et al. (1970) J. Immunol. 105: 55-69.
Croix et al. (1996) J. Exp. Med. 183: 1857-1864.
DeBruijn and Fey (1985) Proc. Natl. Acad. Sci. USA 708-712.
Dempsey et al. (1996) Science 271:348-350.
Dolmer and Sottrup-Jensen (1993) FEBS Lett. 315: 85-90.
Fischer et al. (1996) J. Immunol. 157: 549-556.
Fritzinger et al. (2008a) Mol. Immunol. 45: 4112.
Fritzinger et al. (2008b) Adv. Exp. Med. Biol. 632: 293-307.
Fritzinger et al. (2009) Dev. Comp. Immunol. 33: 105-116.
Ganem and Prince (2004) N. Engl. J. Med. 350: 1118-1129.
Gilbert et al. (1987) J. Control. Release 5: 113-118.
Goncalves et al., 2004) Virology 326: 20-28.
Gong et al. (2009a) Int. J. Pharm. 365: 89-99.
Gong et al. (2009b) BMC Biotechnol. 9: 8.
Green et al. (2001) Vaccine 20: 242-248.
Greginat et al. (2001) J. Exp. Med. 194: 1711-1719.
Haas et al. (2002) Immunity 17: 713-723.
Hagenaars et al. (2010) J. Control. Release 144: 17-24.
HogenEsch (2002) Vaccine20: S34-S39.
Hyun et al. (2007) Biomacromolecules 8: 1093-1100.
Janssen et al. (2009) EMBO J. 28: 2469-2478.
Jeong et al. (1997) Nature 388: 860-862.
Kang et al. (2010) Biomaterials 31: 2453-2460.
Koch et al. (2005) Virology 340: 277-284.
Kölln et al. (2004) J. Immunol. 173: 5540-5545.
Kölln et al. (2005) Immunol. Lett. 98: 49-56.
Koleva et al. (2002) Gastroenterology 122: 697-708.
Kolla et al. (2007) PloS ONE 2: e1044.
Kopf et al. (2002) Nat. Med. 8: 373-378.
Lachmann et al. (1982) J. Exp. Med. 156: 205-216.
Lang et al. (1987) Cell 51: 675-686.
Law and Dodds (1997) Protein Sci. 6: 263-274.
Leroux-Roels (2010) Vaccine 285: C25-C36.
Martinelli et al. (1978) J. Immunol. 121: 2043-2047.
Mathews et al. (1980) Ann. Intern. Med. 93: 443-445.
Medicus et al. (1976) J. Exp. Med. 144: 1076-1093.
Milich and Chisari (1982) J. Immunol. 129: 320-325.

Milich and Leroux-Roels (2002) Autoimmun. Res. 2: 248-257.
Molina et al. (1996) Proc. Natl. Acad. Sci. USA 93: 3357-3361.
Mulligan et al. (1996) J. Clin. Invest. 98: 503-512.
Newman et al. (1984) Complement 1: 213-227.
Nicholls et al. (2010) Ann. N.Y. Acad. Sci. 1213: 46-61.
Nielsen et al. (2002) J. Leuk. Biol. 72: 249-261.
O'Neil et al. (1988) J. Immunol. 140: 1939-1945.
Pai et al. (2009) AAPS J. 11: 88-98.
Peng et al. (2010) Biomaterials 31: 5227-5236.
Pepys (1974) J. Exp. Med. 140: 126-145.
Petrella et al. (1987) J. Immunol. Meth. 104: 159-172.
Petrowsky et al. (2004) Immunol. Cell Biol. 82: 488-492.
Pihlgren et al. (2004) Vaccine 23: 329-335.
Qiao et al. (2005) Int. J. Pharm. 294: 103-112.
Ross et al. (1982) J. Immunol. 129: 2051-2060.
Sinha et al. (2004) Int. J. Pharm. 278: 1-23.
Suradhat et al. (2001) Vet. Immunol. Immunopathol. 83: 79-92.
Suresh et al. (2003) J. Immunol. 170: 788-794.
Tack et al. (1980) Proc Natl Acad Sci USA 77: 5764-5768.
Taniguchi et al. (1996) Transplantation 62: 678-681.
Test et al. (2001) Infect. Immun. 69:3031-3040.
Till et al. (1982) J. Clin. Invest. 69: 1126-1135.
Till et al. (1987) Am. J. Pathol. 129: 44-53.
Villiers et al. (1999) J. Immunol. 162: 3647-3652.
Villiers et al. (2003) Int. Immunol. 15: 91-95.
Vogel and Müller-Eberhard (1982). J. Biol. Chem. 257: 8292-8299.
Vogel et al. (1985) Haematol. Blood Transfus. 29: 514-517.
Vogel and Fritzinger (2007) Curr. Pharm. Des. 13: 2916-2926.
Vogel and Fritzinger (2010) Toxicon 56: 1198-1222.
Willemse et al. (2008) Clin. Chim. Acta 389: 181-182.
Wu et al. (2012) Biomaterials 33: 2351-3260.
Zaharoff et al. (2007) Vaccine 25: 2085-2094.
Zhang et al. (2006) Biomacromolecules 7: 2492-2500.
Zhang et al. (2007) Blood 110: 228-236.

EXAMPLES

The following examples are intended to illustrate but not limit the present invention.

Example 1. Analysis of Complement Activation 1.1. Preparation of Sensitized Sheep Erythrocytes Sheep whole blood (1 ml, Behringwerke, Marburg) is resuspended in 13 ml cold GVBS$^{++}$ and centrifuged for 10 min at 1,000×g (4° C.). The supernatant is removed and the erythrocytes are again resuspended in 14 ml GVBS$^{++}$. This procedure is repeated until a clear supernatant is obtained. Subsequently, the erythrocytes are resuspended in approx. 5 ml GVBS$^{++}$. Erythrocytes are adjusted by dilution with GVBS$^{++}$ to give an absorption of 1.9 at 412 nm for 30 μl erythrocyte suspension in 1 ml H$_2$O corresponding to a density of 5×10$^8$ cells/ml. After the addition of 2 μl antiserum against sheep erythrocytes (anti sheep red blood cell stroma, Sigma, Taufkirchen) per ml of the adjusted erythrocytes, sensitizing is performed for 1 h in a water bath at 37° C., while inverting the reaction tube regularly after 10 min. The sensitized erythrocytes are washed three times with 2 ml GVBS$^{++}$ and centrifuged for 3 min at 1,000×g (4° C.). The erythrocytes can be stored up to three days. Prior to each use, OD$_{412}$ is adjusted to 1.9.

1.2. Isolation of Guinea Pig Erythrocytes

Approximately one ml blood, obtained from isofluoran-narcotized guinea pigs by punction of the eyes, is taken and immediately transferred into a tube containing 1 ml ice-cold ACD solution. The ACD solution serves as anti-coagulant. The erythrocytes are separated by centrifugation (1,000×g, 4 min, 4° C.), resuspended in 14 ml GVBS$^{++}$ and again centrifuged (1,000×g, 4 min., 4° C.). This procedure is repeated 3 to 4 times until the supernatant remains clear. Finally, the erythrocytes are resuspended in approximately 5 ml GVBS$^{++}$. The erythrocytes are diluted with GVBS$^{++}$ until 30 μl of the erythrocyte suspension in 1 ml H$_2$O gives an absorption of 1.9 (5×10$^8$ cells/ml) at 412 nm.

1.3. Complement Consumption Assay

The complement consumption assay is based on the complement consuming effect of rhC3-derivatives or CVF. If a rhC3-derivative- or CVF-containing sample is incubated with human serum, the complement proteins are consumed depending on the activity of the rhC3-derivative or CVF (Ballow and Cochrane, 1969; Cochrane et. al., 1970). The remaining complement activity of the serum can be detected using sensitized sheep erythrocytes.

First, quantification of human serum is performed by serum titration to achieve hemolysis of sheep erythrocytes by 70-90%. For this purpose, different serum concentrations (serum value) in 2 ml reaction tubes (double measurements) are filled up to 40 μl with GVBS$^{++}$. Additionally, controls are prepared, which contain 40 μl GVBS$^{++}$ (buffer control) only, or 40 μl H$_2$O (complete lysis) only. All reaction mixtures are incubated for 30 min at 37° C. under agitation (Thermomixer 5437, Eppendorf, Hamburg, Germany). Then, 100 μl cold GVBS$^{++}$ or 100 μl H$_2$O (complete lysis) and 30 μl sensitized sheep erythrocytes are added and the reaction mixtures are incubated for 30 min as described above. Subsequently, the samples are kept on ice and 850 μl cold VBS$^{++}$ or 850 μl H$_2$O (complete lysis) are added. The supernatants are transferred into cuvettes, and optical density is measured at 412 nm. Hemolysis is calculated according to the following formula:

$$\% \text{ hemolysis} = \frac{OD_{412} \text{ serum value} - OD_{412} \text{ buffer control}}{OD_{412} \text{ complete lysis} - OD_{412} \text{ buffer control}} \times 100\%$$

For complement consumption assay, the quantity of serum determined in prior tests and the samples (max. 20 μl) are supplemented with GVBS$^{++}$ to give 40 μl. Additionally, reaction mixtures of the following controls are prepared: determined quantity of serum, supplemented with GVBS$^{++}$ to give 40 μl (serum control, 4 to 5 samples); 40 μl GVBS$^{++}$ (buffer control) and 40 μl H$_2$O (complete lysis). All reaction mixtures are incubated for 3 hours at 37° C. under agitation. After the addition of 100 μl cold GVBS$^{++}$ or 100 μl H$_2$O (complete lysis) and 30 μl adjusted sensitized sheep erythrocytes, the reaction mixtures are incubated for 30-40 min as described above. After 15 min, the serum control as well as the complete lysis control are measured according to the following principle. The samples are kept on ice, 850 μl cold VBS$^{++}$ or 850 μl H$_2$O for complete lysis are added and centrifuged (4° C., 2,000×g, 2 min.). Supernatants are transferred into cuvettes and the optical density is measured at 412 nm. Lysis is calculated according to the following formula:

$$\% \text{ hemolysis} = \frac{OD_{412} \text{ serum control} - OD_{412} \text{ buffer control}}{OD_{412} \text{ complete lysis} - OD_{412} \text{ buffer control}} \times 100\%$$

In case the value for the serum control is clearly below 80% of the complete lysis value, a second serum control is taken after 10 further minutes of incubation and measured as described above. Once a value of 70-80% hemolysis is obtained, all reaction mixes are measured and evaluated according to the same principle. In order to facilitate comparison of different series of measurements, values are referred to the corresponding serum control.

1.4. Solid Phase Complement Consumption Assay

For characterization of complement consuming activity of the recombinant strep-tagII-rhC3-derivatives, a solid phase assay is performed as described in U.S. Pat. No. 7,553,931B2. The assay comprises immobilizing of the rhC3-derivatives as Strep-tagII fusion proteins to Strep-Tactin which is bound to the surface of ELISA plates. The subsequent addition of buffer and serum facilitates the conduction of the complement-consumption-assays in the ELISA plate. For immobilization, a Strep-tagII is selected which is a peptide consisting of 8 amino acids (WSHPQFEK).

In a first step, 3 µg strep-tactin (diluted in 40 µl incubation solution) is immobilized overnight at 4° C. on the surface of the wells of an ELISA plate (Greiner, Frickenhausen, Germany). Then, the wells are washed 3 times with 200 µl washing buffer and subsequently blocked with 200 µl 3% bovine serum albumin in phosphate-buffered saline for 5 hours at room temperature. After washing the wells again (3 times), different volumes of the supernatants or of the samples are provided in the wells. Protein concentration in the supernatants is determined densitometrically. After overnight incubation at 4° C. under agitation, the wells are washed 3 times with washing buffer. Subsequently, $GVBS^{++}$ and the amounts of serum determined in serum titration are added, giving a volume of 60 µl. The ELISA plate is sealed with paraffin and fixed to the bottom of an incubation shaker. Subsequently, incubation is performed for 3 hours at 37° C., 150 rpm. Supernatants are transferred into 2 ml reaction tubes, and following addition of 100 µl $GVBS^{++}$ and 30 µl sensitized erythrocytes the complement consumption assay is conducted as described.

1.5. Bystander Lysis Assay

This test for detecting hemolytic activity is based on fluid C5-activation and can be determined by lysis of non-sensitized guinea pig erythrocytes (Vogel, 1985). In this method, the extent of complement activation is determined by photometric measurement of released hemoglobin. Different amounts of the protein to be analyzed are diluted in 20 µl $GVBS^{++}$ mixed with 20 µl guinea pig serum (Sigma, Taufkirchen, Germany) and 20 µl guinea pig erythrocytes ($5 \times 10^8$ cells/ml) in a 2 ml reaction tube and incubated for 3 hours at 37° C. under agitation (Thermomixer 5436, Eppendorf, Hamburg, Germany). The reaction is stopped by adding 1 ml ice-cold $VBS^{++}$-buffer. The erythrocytes are centrifuged (2,000×g, 4° C., 2 min) and released hemoglobin in the supernatant is determined by measurement of extinction at 412 nm. Reaction mixtures with 20 µl erythrocytes and 40 µl $H_2O$ (complete lysis) or 20 µl guinea pig serum, 20 µl erythrocytes and 20 µl $GVBS^{++}$ (serum control), respectively, serve as controls.

1.6. Assay for Factor B Cleavage Activity

To detect cleavage of Factor B into Ba and Bb, rhC3-derivatives are incubated at a concentration of 1 µM in the presence of a three-fold molar excess of Factor B, 0.5 µM Factor D and $MgCl_2$ at 37° C. for up to 24 hours. Controls include CVF and EDTA (Vogel and Müller-Eberhard, 1982). The reaction mixtures are analyzed by 7.5% (w/v) SDS polyacrylamide gel electrophoresis (SDS PAGE) under non-reducing conditions to monitor the disappearance of Factor B and the appearance of the cleavage products Ba and Bb. Subsequent western blots may be performed to confirm the results obtained by SDS PAGE.

1.7. Assay for C3 Cleavage Activity

This assay determines the activity of C3/C5 convertases formed by rhC3-derivatives or CVF (as control) to activate human C3 by cleaving off the C3a peptide. To analyze C3 cleaving activity, a C3 convertase is pre-formed using a rhC3-derivative and human Factor B and Factor D as described in section 1.6. The convertase formation is stopped by the addition of EDTA (final concentration 5 mM) and purified human C3 is added. The reaction mixture is incubated at 37° C. for one hour or any other appropriate period of time. Aliquots are taken and immediately transferred into an ice water bath to stop further C3 activation. C3 cleavage is monitored by 7.5% (w/v) SDS polyacrylamide gel electrophoresis (SDS PAGE) under non-reducing conditions analyzing the disappearance of the C3 α-chain and appearance of the C3 α'-chain. Subsequent western blots may be performed to confirm the results obtained by SDS PAGE.

1.8. Assay for C5 Cleavage Activity

This assay performed as described by Petrella et al. (1987) determines the activity of C3/C5 convertases formed by rhC3-derivatives or CVF (as control) to activate human C5 by cleaving off the C5a peptide. The C5 convertase is pre-formed using a rhC3-derivative (3 µg) and human Factor B and Factor D as described in section 1.6. After convertase formation, the reaction is stopped by the addition of EDTA to a final concentration of 5 mM. Then 5 µl of this reaction mixture is added to 25 µl containing 7 µg purified human C5 in phosphate-buffered saline. After incubation at 37° C. for 24 hours, the reaction is stopped by the addition of 7 µl Laemmli gel loading buffer followed by boiling for 5 min. C5 cleavage is monitored by 7.5% (w/v) SDS polyacrylamide gel electrophoresis (SDS PAGE) under non-reducing conditions analyzing the disappearance of the C5 α-chain and appearance of the C5 α'-chain. Subsequent western blots may be performed to confirm the results obtained by SDS PAGE.

1.9. Determination of the Stability of C3 Convertases 500 ng of each native CVF (nCVF), hC3, or rhC3-derivative are mixed with 950 ng of factor B and 8 ng of factor D in a volume of 60 µVBS (2.5 mM Na-5,5-diethyl-barbituric acid, 143 mM NaCl, pH 7.4). After addition of $MgCl_2$ to a final concentration of 10 mM, the samples are incubated for 2 h at 37° C. to allow for convertase formation. Subsequently, all samples are supplemented with EDTA to a final concentration of 10 mM to inhibit further formation of convertases. Thereafter, the samples are incubated at 37° C. and after different periods of incubation 20 µl aliquots are added to 150 µM Boc-Leu-Gly-Arg-7-amido-4-methylcoumarin acetate (Sigma, Taufkirchen, Germany) in 180 µl VBS. The time-course of fluorophore release is determined in black FIA-Plates (96 K, Greiner Bio-One, Frickenhausen, Germany) using an excitation filter of 370 nm and an emission filter of 465 nm in a microplate reader (Genios, Tecan, Creilsheim, Germany). Values after 60 min of fluorophore release are defined as 100%. The slope of the graph is used to determine the enzymatic activity of the sample.

Example 2. Tissue Culture and Recombinant Expression 2.1. Cell Culture

COS-7 cells, HEK293 and CHO cells are cultured in an incubator (Heraeus Instruments Begasungsbrutschrank 6060) in a water saturated atmosphere (5% $CO_2$) at 37° C. Growth is performed in DMEM medium (Gibco/BRL, Eggenstein, Germany) which is supplemented with 10% fetal calf serum (Biochrom, Berlin, Germany). As soon as cells grow confluently in the tissue culture flasks (75 cm³, Cellstar, Greiner Labortechnik, Frickenhausen, Germany), they are passaged into a new culture flask (approximately every 3 days). The cell supernatant is removed and the cells are washed with phosphate-buffered saline. After the addition of 4 µl trpysin/EDTA (Gibco BRL, Eggenstein, Germany), cells are incubated for 5 min in an incubator. Detachment of the cells from the bottom is supported by gentile shaking and is controlled under the microscope. When the cells are almost completely detached, the procedure is stopped by adding 8 ml serum-containing medium. The suspension is transferred into a 15 ml-reaction tube, and the cells are sedimented by centrifugation (5 min, 1,000×g, RT). The supernatant is removed, the pellet is resuspended in 10 ml serum-containing medium and 1 to 3 ml of the cell suspension are transferred into a new tissue culture flask and supplemented with serum containing medium to give a final volume of 13 ml.

Drosophila S2 cells are cultured in serum-free media (Hi-Five plus glutamine, Invitrogen) in the absence of blasticidin as described (Fritzinger et al., 2009).

2.2. Transfection 2.2.1. Transfection of Mammalian Cells.

For expression in mammalian systems, expression vector pcDNA3 (Invitrogen, Leek, the Netherlands) comprising the corresponding genes is introduced into the cells by the GenePorter reagent (PeqLab, Erlangen).

DNA (1 to 4 µg) and 10 to 15 µl GenePorter transfection reagent are diluted in 500 µl serum-free medium and pooled. The reaction mix is incubated for 45 min at room temperature. The cells which have been passaged in a 6-well plate (300-500 µl of cell suspension with 2 ml serum-containing medium per well; TC-plate, 6-well, Greiner Labortechnik, Frickenhausen, Germany), are washed with phosphate buffered saline, and then the DNA GenePorter mixture is carefully added drop-wise to the cells. After 3 hours in the incubator, the medium is replaced by 2 ml serum-containing medium, and the cells are kept for 2 to 3 days in the incubator for cell growth. When using Nutridoma HU (100×; Roche Diagnostics, Mannheim, Germany), the cells are added to Nutridoma HU after transfection in serum-free medium and kept growing in the incubator for 2 to 3 days.

A reaction mixture without DNA is prepared as negative control. If applicable, a reaction mixture with 1 µg pEGFP-N1 is prepared as positive control. Plasmid pEGFP-N1 encodes the green fluorescence protein (GFP) and can be used for determining transfection efficiency since the GFP expressing cells can be detected using a fluorescence microscope. The supernatant of the pEGFP-N1 transfected cells is removed after 24 hours, cells are washed with 2 ml PBS, and 500 µl trypsin/EDTA is added. Detachment of cells is performed for 5 min in the incubator. Then, 2 ml phosphate-buffered saline is added and the cell suspension is transferred into a 50 ml reaction tube for centrifugation (5 min., 1,000×g, RT). The supernatant is removed and the cell pellet is resuspended in 2 ml phosphate-buffered saline. 10 µl thereof are provided in a Neubauer-counting chamber, and the number of fluorescening cells and the total number of all cells are counted in the outer four squares.

Calculation of the Cell Number/Ml:

$$\text{Cells/ml} = \frac{\text{Number of cells of all squares}}{4} \times 10^4$$

Calculation of Transfection Efficiency:

$$\text{Efficiency (\%)} = \frac{\text{number of fluorescent cells}}{\text{number of cells of all squares}} \times 100\%$$

2.2.2. Transfection of Insect Cells.

Transfection of Drosophila S2 cells is performed as described (Fritzinger et al., 2009). Briefly, Drosophila S2 cells are transfected with a mixture of the expression plasmid and pCoBlast (ratio of 19:1 w/w) using the calcium phosphate method.

2.3. Expression Under Selection Pressure

In order to increase yields, stably expressing mammalian lines are kept in culture containing an antibiotic. Depending on their resistance, 10 µl/ml culture medium is added to an antibiotic stock solution (G418), or 5 µl/ml culture medium is added to zeocine.

2.4. Expression in Serum or Protein-Free Medium

For culturing in serum-free or protein-free medium, cells are step-wise adapted with SCF30- or Mampf3-medium (Promocell, Heidelberg, Germany) with 1 mM L-glutamine. The percentual portion of the serum-free or protein-free medium is increased by 25% in every second passage.

2.5. Monoclonalization

In order to obtain a homogeneous cell population, monoclonalization is conducted, wherein the different cells are monoclonalized, expanded and subsequently examined with respect to their expression level by Western blotting and immuno printing.

For this purpose, all cells are incubated for 3 to 4 passages after transfection under selection pressure in order to guarantee that a large portion of cells contains the resistance and therefore expresses the target protein. This procedure allows to adjust the cell number per ml, which is counted thereafter using a Neubauer-counting-chamber, with the number of cells expressing the target protein. Subsequently, cell density is set to 1 cell per 100 µl medium with 10% FCS, and 100 µl of this dilution are introduced into each of the 48-96 wells of the 96 well plates (Greiner Labortechnik, Frickenhausen, Germany). After approximately one week, the medium is removed, and 100 µl medium with 10% fetal calf serum is added. After approximately 2 weeks, the wells are examined under the microscope for one colony per well. Some are selected, and the cells are detached with 25 µl trypsin for 5 min at 37° C. and completely transferred into the well of a 24-well-plate (Greiner Labortechnik, Frickenhausen, Germany), which is completely filled with 500 µl medium containing 10% fetal calf serum. After one week, this procedure is repeated with 100 µl trypsin, and all cells are placed into a well of a 6-wellplate. After another 3 to 4 days, 100 µl supernatant per well are taken and examined by Western blotting and subsequent immunoprinting. The cell population, which finally shows the strongest band, is further expressed under selection pressure and cryoconserved, if applicable.

2.6. Densitometric Determination of Protein Concentrations

For densitometric determination of protein concentrations, 4-5 dilutions of known concentration of native CVF or human C3 (depending on the sample) are applied in addition to different volumina of the protein-containing sample to be determined. The protein concentration in the calibration series is adjusted to the expected concentration range of protein in the sample. The gel is subjected to wet-blotting or semidry-blotting procedures and the proteins are subsequently stained using immunoprinting. Then, the membrane is scanned and the concentration of the sample is determined using the program Imagemaster 1D Elite Version 2.01 (Amersham Pharmacia Biotech, Freiburg, Germany).

2.7. Determination of Recombinant Proteins by ELISA

For the determination of recombinant proteins by ELISA, approximately 1 µg protein diluted in 100 µl incubation solution, is immobilized on the well of an ELISA plate overnight at 4° C. Subsequently, the wells of the plate are washed three times with washing buffer (200 µl). Then, the wells are blocked with 200 µl 5% milk powder in phosphate-buffered saline for 5 hours at room temperature. After washing three times, 200 µl of the supernatant of transient expression or purified diluted proteins in phosphate-buffered saline, respectively, are introduced into the wells and incubated overnight under agitation at 4° C. After this, the samples are washed three times with washing buffer and incubated with 100 µl of a 1:1000 dilution of the respective antibody in 2.5% milk powder in phosphate buffered saline at room temperature. Subsequently, the samples are washed three times and incubated for one hour with 100 µl of a 1:1000 dilution of an respective peroxidase-conjugate in a 2.5% milk powder in PBS at room temperature. Finally, the samples are washed three times, and then 100 µl detection buffer (for POD) are added. After staining the wells, extinction at 404 nm is measured with a micro titer plate-photometer (ELISA-Reader, SLT-Instruments, Grödingen, Austria, Easy Reader EAR 400AT).

Example 3. Expression and Purification of CVF and Human C3

For the expression of CVF plasmids pUC18CVF and pcDNA3CVF (both contain the cDNA of CVF; Genebank Accession No. U09969) were employed and for the expression of human C3 plasmids pUC18hC3 and pcDNA3hC3 according to U.S. Pat. No. 7,553,931 B2. The expression of recombinant CVF and human C3 was performed as described in Example 2.

For analyses via solid-phase-assays a Strep-tagII sequence was fused to the N-terminus of both molecules. Using the CVF-cDNA two amplification products were generated in two PCR reactions and the amplification products were hybridized by PCR as described in U.S. Pat. No. 7,553,931 B2. Furthermore, an enterokinase-cleavage site was inserted into the cDNA of CVF and human C3 between the signal sequence and the N-terminus of the Strep-tagII to allow for cleavage of the affinity tag.

For separation of low molecular components of the culture supernatants or column fractions, the supernatants or fractions were transferred into a dialysis tube (SpectraPor CE 100, MWCO 100 kDa, Roth, Karlsruhe, Germany) and dialysed overnight against phosphate-buffered saline. The dialysed samples were concentrated with Centricon-units (MWCO 100 kDa, Millipore, Eschborn, Germany). For this purpose, centrifugation was performed at 1,000×g (4° C.) until the desired final volume was reached.

For purification the supernatant (2.5 ml) from transient expression was loaded onto a PD-10-column according to the manufacturer's instructions (Amersham Pharmacia Biotech, Freiburg, Germany). PBS was used as a running buffer. The fractions were examined for recombinant protein by Western blotting and subsequent immunoprinting. Alternatively, 2 ml supernatant of the transient expression were loaded onto a 1 ml EconoPac-column (Biorad, Munich, Germany) using a Tris-buffer (50 mM, pH 7.5). The same buffer containing 500 mM NaCl was used for elution. The fractions were also examined for protein content and dialysed against PBS.

For control purposes, natural CVF was also purified from lyophilized Indian cobra (Naja kaouthia) venom as described (Janssen et al., 2009).

Example 4. Cloning of rhC3-Derivative H5

The rhC3-derivative H5 shown in FIG. 1 was constructed as described in U.S. Pat. No. 7,553,931 B2. The derivative contains the human β-chain and additionally the humanized Factor B- and Factor H-binding sites as well as the cleavage sites for Protease Factor I. In addition to the α-chain, the γ-chain as well as the C3a and the C3d regions were humanized.

For cloning of rhC3-derivative H5, a fragment consisting of pUC18 and the 3'terminus of CVF was obtained from pUC18CVF utilizing Ecl136I and BglII restriction. Subsequently, said fragment was ligated with a fragment obtained from pcDNA3hC3 by EcoRI restriction, followed by mung bean nuclease digestion and BglII restriction. The latter fragment had a size of 1870 bp contained the 5' terminus of C3 cDNA. The vector ligated in this way (referred to as H2Δ2307 bp) contained 1800 bp of the C3 5' terminus and 1000 bp of the CVF 3' terminus.

In order to completely construct rhC3-derivative H5, vector H2Δ2307 bp was digested with BglII. The middle region of the C3-cDNA was isolated from plasmid pUC18hC3 via its BglII restriction sites and inserted into the vector. The resulting rhC3-derivative H5 was then inserted into an analogously digested pcDNA3-vector via the EagI-restriction sites. Subsequently, a Strep-tag was inserted between the signal sequence and the N-terminus as described in U.S. Pat. No. 7,553,931 B2.

Example 5. Expression and Purification of rhC3-Derivative H5

Expression of rhC3-derivative H5 in CHO cells was confirmed by ELISA via Strep-Tactin, immunoblot analysis, and densitometry. All methods provided yields of 1-2 mg/l.

For quantification by immunoblot polyclonal serum against human C3 was employed. Since rhC3-derivative H5 has 90% identity compared to human C3, it was assumed that the polyclonal serum detects both proteins with a variance that is lower than the one of densitometric quantification.

Determination of the concentration was confirmed by a sandwich ELISA utilizing an immobilized monoclonal C3d-antibody or the immobilized antibody fragment C3-1. After incubation of the immobilized antibodies with the recombinant proteins, the detection was performed using a polyclonal C3-antiserum. In addition to the samples, various concentrations of human C3 were employed. The evaluation of the ELISA analysis confirmed the concentrations obtained from the densitometric quantification.

For purification, supernatant (500 ml) obtained from stably transfected cells was adjusted to pH 7.5, passed trough a 0.45 µm cellulose acetate membrane and loaded onto a Poros HQ/M anion exchange column equilibrated with 50 mM Tris, pH 7.5 using ÄKTA purifier (Amersham Bioscience, Freiburg, Germany). The recombinant protein was eluted using a linear (0-500 mM) NaCl gradient. Fractions (2 ml) were analyzed using 7.5% SDS-PAGE and western blotting, pooled and dialyzed against phosphate buffered saline (PBS). The pooled sample was diluted (1:9) in 50 mM sodium phosphate, 0.55 M sodium sulfate buffer, pH 7.0, filtered (0.2 µm) and applied to a thiophilic resin (1.5 ml, BD Bioscience, Heidelberg, Germany) equilibrated with 50 mM sodium phosphate, 0.5 M sodium sulfate buffer, pH 7.0. After extensive washing of non-adsorbed proteins with the equilibration buffer (>30 column volumes), elution was performed using 50 mM sodium phosphate buffer, pH 7.0. Fractions (1.5 ml) were analyzed by 7.5% SDS-PAGE and western blotting. Fractions containing H5 were pooled, dialyzed against 100 mM Tris, 150 mM NaCl, pH 8.0 (buffer W), loaded onto Strep-Tactin sepharose (2 ml, IBA, Göttingen, Germany) equilibrated with buffer W, washed with 10 ml buffer W, and eluted with buffer W containing 2.5 mM desthiobiotin. Protein concentration and purity of the fractions were analyzed by 7.5% SDS-PAGE. Pooled fractions were dialyzed against PBS and employed for further characterization.

Example 6. Characterization of rhC3-Derivative H5

Following successful transient expression, rhC3-derivative H5 was used in a solid phase-assay, where CVF and human C3 served as controls (FIG. 2). Hybrid H5 clearly showed complement-consuming activity which is comparable to CVF. Despite of its degree of 90% humanization, hybrid H5 completely retains complement-consuming activity.

Figure 3:
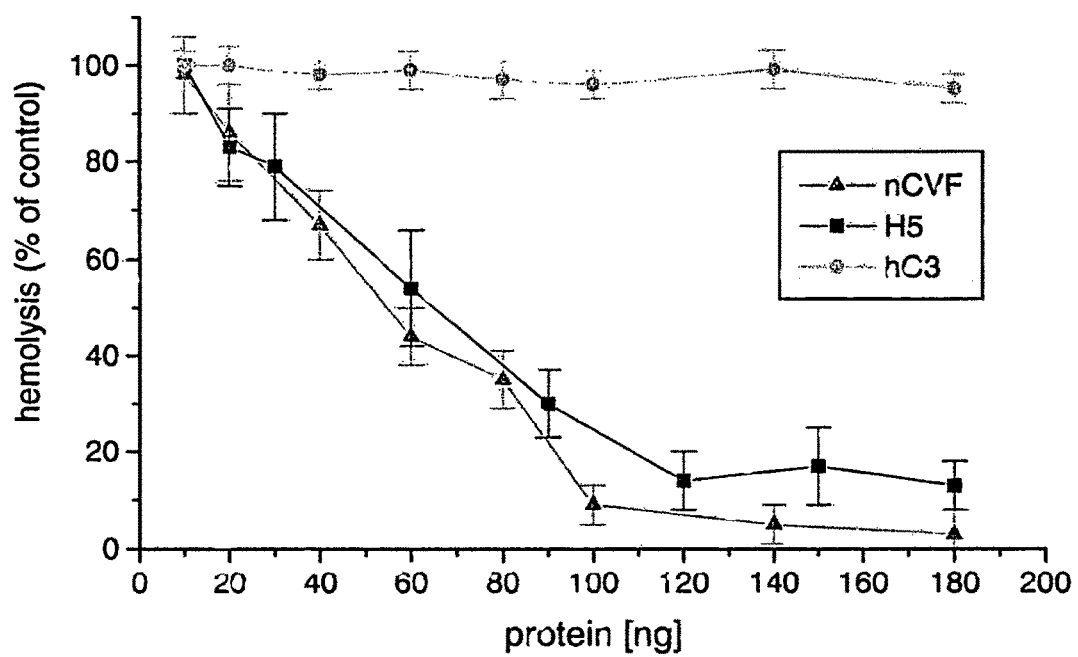
FIG. 3 shows the complement-consuming activity of CVF, St-H5 (Strep-tag-fusion construct of rhC3-derivative H5), and human C3. The assay was performed as described in Example 1.3. The figure shows the mean values±standard deviation of at least three independent experiments.

To analyze the functional activity of rhC3-derivative H5 more in detail, we established a stably transfected CHO cell line and purified the protein using thiophilic and strep-tactin resins. A detailed analysis of the complement-consuming activity of H5 over a broad concentration range confirmed the CVF-like activity observed in analyses of transiently expressed rhC3-derivative H5. As evident from FIG. 3, rhC3-derivative H5 exhibits approx. 85% of the complement-consuming activity of purified native CVF.

Figure 4:
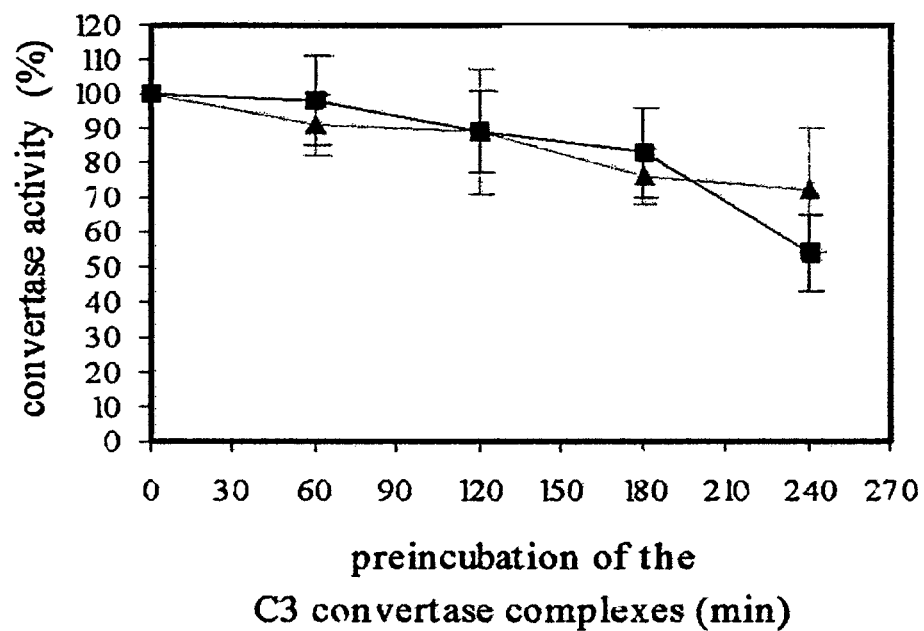
FIG. 4 shows the stability of CVF,Bb and rhC3-derivative H5,Bb C3 convertase complexes (CVF,Bb: gray triangles; rhC3-derivative H5,Bb: black squares). Analysis of the stability was performed as described in Example 1.9. Shown are mean values±s.d. obtained from at least three independent experiments.

Furthermore, we analyzed the formation and stability of the convertase generated by the rhC3-derivative H5 (for details, see Example 4. The recombinant protein activates factor B by producing Bb and Ba in the presence of factor D and $Mg^{2+}$ in an identical manner as $C3(H_2O)$ and CVF. The time-dependent reduction in the release of 7-amido-4-methylcoumarin from a fluorogenic substrate analogue by the action of the convertase revealed a half-life of the rhC3-derivative H5-dependent convertase of approx. 5-6 hours (FIG. 4), which is close to the reported 7 hour half-life of the CVF-dependent convertase (Vogel and Müller-Eberhard, 1982). In contrast, the C3b,Bb convertase complex exhibited no activity, thereby confirming the extremely short half-life in the range of 1 to 2 minutes (Medicus et al., 1976). These results confirm the fact that, in addition to the CVF-α-chain, also the CVF-γ-chain as well as the C3a- and C3d-homologous regions can be substituted by human C3 without loss of complement-consuming activity.

Example 7. Cloning of rhC3-Derivative H6

Figure 5:
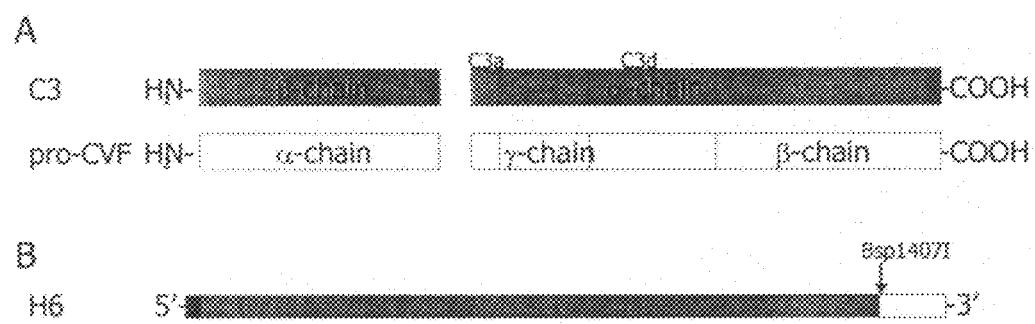
FIG. 5 shows a schematic representation of the rhC3-derivative H6. A: Chain structures of human C3 and pro-CVF. B: Structure of rhC3-derivative H6 cDNA.

The rhC3-derivative H6 shown in FIG. 5 provides 96.3% identity to human C3. For the construction of this derivative, the Bsp1407I-restriction site was used and the region upstream of the Bsp1407I-restriction site was humanized as described in U.S. Pat. No. 7,553,931 B2. For cloning of rhC3-derivative H6, a 350 bp-fragment from pUC18CVF* containing the 3'-terminus of CVF was amplified by PCR. The amplification product and the vector pcDNASt-hC3 were digested with Bsp1407I and XbaI and ligated.

The rhC3-derivative H6 was purified according to established techniques using affinity-chromatographical methods on the basis of the His-tag-system. For this purpose, the insertion of the His-tag was performed in analogy to the insertion of a Strep-tag between the signal sequence and the N-terminus. Briefly, two amplification products were generated as described in U.S. Pat. No. 7,553,931B2. The amplification products were hybridized by PCR followed by insertion via the restriction sites NotI and Bpu1102I into a vector digested in an analogous manner. Subsequently, a Strep-tag was inserted between the signal sequence and the N-terminus as described in U.S. Pat. No. 7,553,931 B2.

Example 8. Expression and Purification of rhC3-Derivative H6

The successful transient expression of rhC3-derivative His-H6 in CHO cells was verified in a sandwich-ELISA via Strep-Tactin and by immunoblot analysis employing polyclonal serum against human C3. Densitometric quantification of these immunoblot analyses showed yields of 1-2 mg/l.

For purification of rhC3-derivative H6, stably expressing CHO-cells were monoclonalized and expanded. Subsequently, imidazole was added to the supernatant of the CHO cells in a final concentration of 20 mM and the mixture was incubated with Ni-NTA-matrix. The elution fractions were then analyzed by immunoblot. The fractions were pooled, dialyzed and quantified in a Sandwich-ELISA. Protein concentrations of 3-4 µg/ml were determined. Densitometric determinations of immunoblot analyses confirmed the quantification by ELISA. Analysis by SDS-PAGE and silver staining revealed a strong protein background in the purified fractions and insufficient binding of rhC3-derivative H6 to the Ni-NTA-matrix.

Example 9. Characterization of rhC3-Derivative H6

Figure 6:
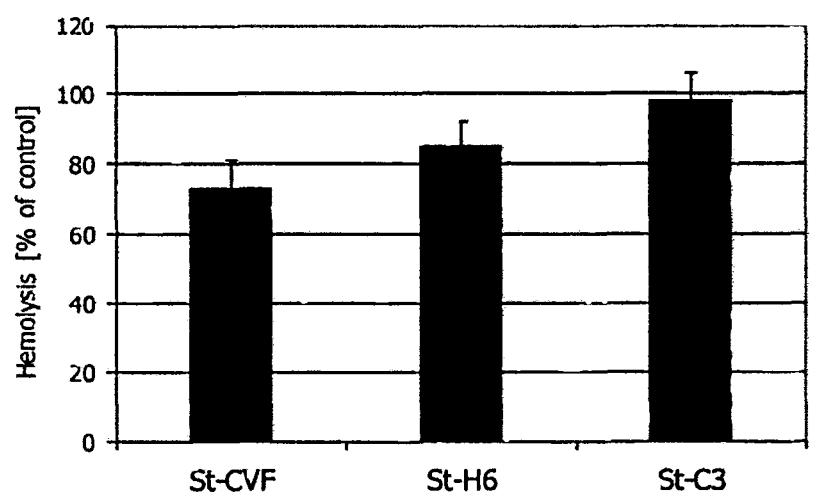
FIG. 6 shows a solid phase-assay with St-H6 (Strep-tag-fusion construct of rhC3-derivative H6), St-CVF (Strep-tag-fusion construct of CVF), and St-C3 (Strep-tag-fusion construct of human C3). The assay was performed as described in Example 1.4. The Figure shows the mean values±standard deviation of at least three independent experiments.

FIG. 6 shows the complement-consuming activity of a supernatant containing Strep-tagII-rhC3-derivative H6 in a solid phase-assay. As evident from the analysis, the complement-consuming activity of rhC3-derivative H6 is retained but slightly lower than that of CVF.

Figure 7:
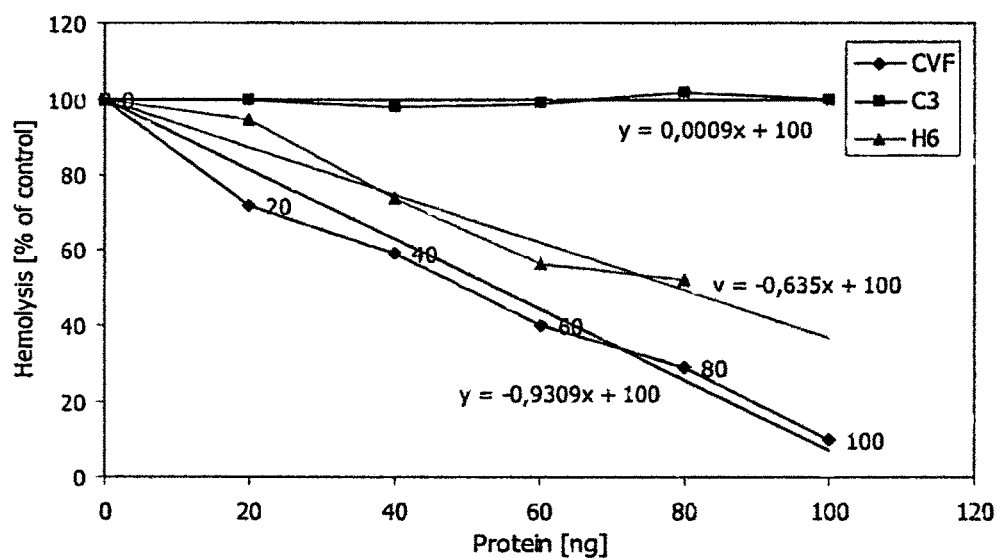
FIG. 7 shows a complement-consumption-assay with CVF, His-tag-fusion construct of rhC3-derivative H6 and human C3. The assay was performed as described in Example 1.3. The figure shows the mean values±standard deviation of at least three independent experiments. The complement-consuming activity was evaluated by linear regression analysis.

For further characterization of rhC3-derivative H6, the C3-convertase activity was also determined in a complement consumption assay in solution (FIG. 7). The data of this analysis show that rhC3-derivative H6 has approximately 68% of the complement-consuming activity of CVF.

Subsequent analyses in a Bystander Lysis-assay (see Example 1.5.) revealed that rhC3-derivative H6 does not exert significant fluid phase C5-convertase activity as compared to CVF.

Example 10. Cloning of rhC3-Derivative HC3-1496

The rhC3-derivative HC3-1496 provides 94% identity to human C3. Cloning of this derivative is performed according to the method described in patents PCT/US2005/05119 and US2010/0179092. Briefly, two PCR reactions are performed using pBS-HuC3-2 in the first reaction as template and following oligonucleotides as primers: TCTGTGTG-GCAGACCCCTTCGAGG (forward) (SEQ.ID. NO. 4) and GAGAAGGCCTGTTCCTTTA-TCCGGATGGTAGAAC-CGGGTAC (revers) (SEQ.ID. NO. 5). In the seceond reaction pCVF-FL3Δ is used as template and following oligonucleotides as primers: CCGGTTCTACCATCCGGATAAAGGAACAGGCCTTC (forward) (SEQ.ID. NO. 6) and CATCCATGACATAGATA-TCATTACCATCTTG (revers) (SEQ.ID. NO. 7). The resulting two PCR products are joined in a PCR reaction and digested with NspV after purification with a Quiagen PCR cleanup kit. Thereafter, the sequence is cloned into pHC3-1550(-sig) treated with NspV and calf intestine alkaline phosphatase. For expression the insert from the resulting plasmid, called pHC3-1496, is isolated and cloned into pMT-Bip/V5-HisA (Invitrogen).

Example 11. Expression of rhC3-Derivative HC3-1496

Expression of rhC3-derivative HC3-1496 is performed in the *Drosophila* S2 cell system as described in US2010/0179092. Briefly, *Drosophila* S2 cells are transfected with a mixture of the expression plasmid and pCoBlast (ratio of 19:1 w/w) using the calcium phosphate method. Thereafter, cells containing both plasmids are selected using blasticidin (25μ/ml). For expression, transfected cells are grown in serum-free medium (Hi-Five plus L-glutamine) in the absence of blasticidin. After reaching a density of $5 \times 10^6$ cells/ml production of rhC3-derivative HC3-1496 is induced by the addition of $CuSO_4$ (final concentration 25 μM) and continued for 4-5 days.

Purification of rhC3-derivative HC3-1496 from the media is performed as described (Fritzinger et al., 2009). Cells from 1 L cultures are removed by centrifugation (5 min at 1000×g), and the media filtered through a 0.45 μm filter to remove any cellular debris. The filtered media are diluted by the addition of an equal volume of 20 mM Tris-HCl, pH 8.0, and applied to a 20 ml ANX-FF-column, and protein is eluted with a linear gradient from 0 to 0.6 M NaCl in the same buffer. Fractions containing rhC3-derivative HC3-1496 are detected by a combination of SDS-PAGE and Western blot analysis, and are then concentrated on a 5 ml ANX-FF column using a 0-0.6 M NaCl step gradient in the same buffer. The concentrated protein is applied to a Sephacryl S-300HR column (2.6 cm×60 cm) equilibrated with 20 mM Tris-HCl, pH 8.0, 0.1 M NaCl. Elution is performed with the equilibration buffer. Fractions containing rhC3-derivative HC3-1496 are detected by a combination of SDS-PAGE and Western blot analysis. The combined fractions are diluted with sodium acetate buffer (pH 5.5) until the conductivity is below 6 mS, and loaded onto a 5 ml CM-FF column. After elution of the protein with a 0 to 0.6 M NaCl gradient in the same buffer, fractions were immediately neutralized by the addition of 1 M Tris-HCl, pH 8, and those fractions containing rhC3-derivative HC3-1496 are identified by a combination of SDS-PAGE and Western blot analysis.

Example 12. Characterization of rhC3-Derivative HC3-1496

Analysis of the stability of the convertase formed by purified rhC3-derivative HC3-1496 and its complement consuming activity, Factor B cleavage activity, and C3 and C5 cleavage activity is performed according the methods of the present patent application and US patent 2010/0179092. According to US patent 2010/0179092 rhC3-derivative HC3-1496 has exhibits about 20 to 50% complement consuming activity as compared to CVF, Factor B cleavage activity about equal to CVF, convertase stability about equal to CVF, C3 cleavage activity about five times better than CVF, and none detected C5 cleavage activity.

Example 13: Synthesis and Characterization of Thermogelling PLGA-PEG-PLGA Hydrogels The biodegradable triblock polymer described in this example has a PEG (1000)/PEG (1500) weight ratio of 20/80, a PLG/PEG weight ratio of 2.1 (68/32), and a lactide/glycolide molar ratio of 85/15. Synthesis of the triblock copolymer is performed according to published protocols (Quiao et al., 2005; WO 02/102309).

10.1. Copolymer Synthesis

Polyethylene glycol (PEG 1000 and PEG 1500) is purchased from Fluka, poly(DL-lactide) from Sigma, glycolide (1,4-Dioxane-2,5-dione) from Sigma, and stannous 2-ethylhexanoate from Aldrich.

A total of 50 g of DL-lactide, glycolide and PEG are used for polymerization (28.9 g DL-lactide, 5.1 g glycolide, 3.2 g PEG 1000, 12.8 g PEG 1500). Under nitrogen atmosphere, PEG 1000 and PGE 1500 (weight ratio of 20/80) is dried in a three-necked flask (equipped with a nitrogen inlet, thermometer, and distillation head for removal of water) under vacuum and stirring at 120° C. for 2 h. Stannous 2-ethylhexanoate (0.2% w/w) is added into a vigorously dried polymerization tube followed by the addition of DL-lactide and glycolide monomers. Then the tube is sealed under vacuum. The sealed tube was immersed and kept in an oil bath thermostated at 150° C. After 8 h the tube was cooled to room temperature, then broken and the product was dissolved in cold water. After completely dissolved, the copolymer solution is heated to 80° C. to precipitate the copolymer and to remove the water-soluble low molecular weight copolymers and unreacted monomers. The supernatant is decanted, the precipitated copolymer is again dissolved in cold water followed by heating to induce precipitation. This process of dissolution followed by precipitation is repeated three times. Finally, the copolymer is dried under vacuum at room temperature until constant weight.

10.2. Molecular Weight Determination

The molecular weight of the copolymer is determined by gel permeation chromatography using polystyrene standards as described by Quiao et al. (2005).

10.3. Measurement of Gelation Temperature

The gelation temperature is determined as described by Quiao et al. (2005). A 20 ml transparent vial containing a 2.6 g heavy magnetic bar (10×5 mm i.d.) and 10 g water solution of the copolymer (15% w/w, 20% w/w and 25% w/w), is placed in a water bath. The solution is heated at a constant rate of 2° C. per minute with constant stirring at 200 rpm. When the magnetic bar stops stirring due to gelation of the solution, the temperature read from the thermometer is determined as gelation temperature.

Example 14: In Vitro Degradation of Thermogelling PLGA-PEG-PLGA Hydrogels

The in vitro degradation behavior of the copolymer of Example 10 is evaluated by the mass loss and the molecular weight reduction with time upon incubation in phosphate-buffered saline.

Samples (0.5 ml) are incubated in phosphate-buffered saline pH 7.4 at 37° C. under mild agitation in a water bath. The solid residues are removed from the incubation medium at scheduled time intervals and lyophilized. The samples are weighted and the weight loss is calculated. Then the solid residues are solved in cold water and analyzed by gel permeation chromatography using polystyrene standards as described by Quiao et al. (2005).

Example 15: Biodegradation of Thermogelling PLGA-PEG-PLGA Hydrogels

To test the in vivo gel formation behavior and the degradation characteristics of PLGA-PEG-PLGA hydrogels, the hydrogel is injected subcutaneously into mice that have been anesthetized with ethyl ether. The resulting gel implants are then allowed to develop in vivo over the experimental period. At each of the post-injection sampling points, the mice are sacrificed, the gel implants are removed from the subcutaneous injection site, and the removed gel implants are analyzed as described in Example 11.

Two groups of wild-type BALB/c mice (each group: 16 mice) are analyzed for the in vivo gel formation behavior and the degradation characteristics: group 1: 20% (w/w) polymer; group 2: 25% (w/w) polymer. The analysis is performed according to following schedule: implantation of 200 µl polymer on day 0, analysis of size in two mice on days 1, 2, 3, 4, 5, 10, 20 and 30.

Example 16: In Vitro Release of CVF from PLGA-PEG-PLGA/CVF-Composits

The PLGA-PEG-PLGA triblock copolymer of Example 10 is dissolved at room temperature in distilled water containing different concentrations of CVF (0.2 mg/ml up to 2.0 mg/ml) to make a 20% w/w or 25% w/w solution. Then 1 ml of the formulation is placed in a 20 ml vial, incubated at 37° C. for 2 min until gelling, and 10 ml of phosphate-buffered saline pH 7.4 is added. The vial is shaken at 100 rpm at 37° C. At specified sample collection times, a sample is withdrawn and replaced by an identical volume of phosphate-buffered saline pH 7.4 to maintain release conditions.

The amount of released CVF is determined by bicinchoninc acid (BCA) assay using BCA™ Protein Assay Kit (Pierce, USA). The structural and functional integrity of released CVF is determined by a complement consumption assay as described in Example 1.3.

Example 17: In Vitro Release of rhC3-Derivative H5 from PLGA-PEG-PLGA/rhC3-Derivative H5 Composits The PLGA-PEG-PLGA triblock copolymer of Example 10 is dissolved at room temperature in distilled water containing different concentrations of rhC3-derivative H5 (0.2 mg/ml up to 2.0 mg/ml) to make a 20% w/w or 25% w/w solution. Then 1 ml of the formulation is placed in a 20 ml vial, incubated at 37° C. for 2 min until gelling, and 10 ml of phosphate-buffered saline pH 7.4 is added. The vial is shaken at 100 rpm at 37° C. At specified sample collection times, a sample is withdrawn and replaced by an identical volume of phosphate-buffered saline pH 7.4 to maintain release conditions.

The amount of released rhC3-derivative H5 is determined by bicinchoninc acid (BCA) assay using BCA™ Protein Assay Kit (Pierce, USA). The structural and functional integrity of released rhC3-derivative H5 is determined by a complement consumption assay as described in Example 1.3.

Example 18: Biodegradation and Release Characteristics of PLGA-PEG-PLGA/CVF Composits To test the in vivo gel formation behavior and the release characteristics of composits of PLGA-PEG-PLGA hydrogels containing CVF, the composits are injected subcutaneously into mice that have been anesthetized with ethyl ether. The resulting gel implants are then allowed to develop in vivo over the experimental period. At each of the post-injection sampling points, the mice are sacrificed, serum samples are taken for a complement consumption assay as described in Example 1.3., and for the determination of CVF by ELISA as described in Example 2.7. Thereafter, the gel implants are removed from the subcutaneous injection site. After determination of the volume of the removed gel implants, the remaining in vitro releasable amount of CVF is determined by ELISA and protein determination (bicinchoninc acid assay using BCA' Protein Assay Kit of Pierce, USA). The structural and functional integrity of released CVF is determined by a complement consumption assay as described in Example 1.3.

Two groups of wild-type BALB/c mice are analyzed for the in vivo gel formation behavior and the release characteristics: group 1: 20% (w/w) polymer containing in 200 μl 0.25 mg CVF; group 2: 25% (w/w) polymer containing in 200 μk 0.25 mg CVF. The analysis is performed according to following schedule: implantation of 200 μl polymer composit on day 0, analysis of polymer size and CVF release 2 hours after injection, 5 hours after injection, and 1, 2, 3, 4, and 5 days after injection.

Example 19: Biodegradation and Release Characteristics of PLGA-PEG-PLGA/rhC3-Derivative H5 Composits To test the in vivo gel formation behavior and the release characteristics of composits of PLGA-PEG-PLGA hydrogels containing rhC3-derivative H5, the composits are injected subcutaneously into mice that have been anesthetized with ethyl ether. The resulting gel implants are then allowed to develop in vivo over the experimental period. At each of the post-injection sampling points, the mice are sacrificed, serum samples are taken for a complement consumption assay as described in Example 1.3., and for the determination of rhC3-derivative H5 by ELISA as described in Example 2.7. Thereafter, the gel implants are removed from the subcutaneous injection site. After determination of the volume of the removed gel implants, the remaining in vitro releasable amount of rhC3-derivative H5 is determined by ELISA and protein determination (bicinchoninc acid assay using BCA' Protein Assay Kit of Pierce, USA). The structural and functional integrity of released rhC3-derivative H5 is determined by a complement consumption assay as described in Example 1.3.

Two groups of wild-type BALB/c mice are analyzed for the in vivo gel formation behavior and the release characteristics: group 1: 20% (w/w) polymer containing 200 μl 0.25 mg rhC3-derivative H5; group 2: 25% (w/w) polymer containing in 200 μl 0.25 mg rhC3-derivative H5. The analysis is performed according to following schedule: implantation of 200 μl polymer composit on day 0, analysis of polymer size and release of rhC3-derivative H5 2 hours after injection, 5 hours after injection, and 1, 2, 3, 4, and 5 days after injection.

Example 20: Hepatitis B Vaccination of Mice Using PLGA-PEG-PLGA Hydrogel-Delivered HbsAg and CVF Studies with inbred congenic moude strains that are genetically identical except in the MEW region, have demonstrated that the immune response to HbsAg is strongly influenced by the MHC-linked genes and that B10.M mice with the H-$2^f$ haplotype are not responsive to HbsAg (Milich and Chisari, 1982). This HbsAg-non-responder strain B10.M (Jackson Laboratory, USA) is used to evaluate the efficacy of HbsAg vaccination using PLGA-PEG-PLGA hydrogel-delivered HbsAg and CVF. The HbsAg-responder mouse strain BALB/c is used for control.

20.1. Preparation of PLGA-PEG-PLGA Hydrogel-Embedded HbsAg and CVF.

Recombinant HBsAg (rHBsAg) produced in yeast *Saccharomyces cerevisiae* (MBS) and CVF are formulated with PLGA-PEG-PLGA hydrogel in the solution phase so that each dose of vaccine contains 2 μg HBsAg and 0.25 mg CVF per 200 μl hydrogel.

20.2. Immunization.

All mice are immunized at 6-8 weeks of age. The mice are divided into groups (each n=5) which are injected s.c. in the back with a 0.2 ml volume of one of the following vaccines: 2 μg HBsAg in saline, 2 μg HBsAg+0.25 mg CVF in saline, 2 μg HBsAg in hydrogel, or 2 μg HBsAg+0.25 mg CVF in hydrogel. In an additional control mice receive 2 HBsAg, H-B-Vax II (Merck Sharp & Dohme, West Point, Pa.) which is formulated with aluminium hydroxide.

Responder BALB/c mice receive one dose of each vaccine, and serum samples are collected 4 weeks later to measure anti-HBsAg antibody levels. BALB/c mice are boosted one day after sera collection with the same vaccine, and splenocytes are harvested 2 weeks later and tested in the T cell-proliferation assay.

Non-responder B10.M mice receive two doses of each vaccine at an 8 week interval, and serum samples are collected 4 weeks after the first immunization and 2 weeks after the second immunization for determination of the anti-HBsAg antibody levels. Splenocytes are harvested 2 weeks after the second immunization for the T cell-proliferation assay.

20.3. Determination of HbsAg-Specific Antibodies.

HBsAg-specific antibodies are analyzed as described (Chow et al., 1998). Serum samples are collected by tail bleeding before and at different times after immunization and are stored at −20° C. until analysis. For the determination of HBsAg-specific antibodies, serial 3-fold dilutions of the test sera are added to each well of microtiter plates that have been coated with 0.5 μg/ml HBsAg and blocked with 1% (w/w) milk powder in phosphate-buffered saline before use. After incubation for 2 h at 37° C., the wells are washed with phosphate-buffered saline containing 0.05% Tween 20. Bound antibodies are detected using horseradish peroxidase-conjugated goat anti-mouse Ig Fc antibodies (Chemicon International, Temecula, Calif.). Color is generated by adding 2,2'-azino-di(3-ethylbenzthiazoline-6-sulfonic acid) (Sigma-Aldrich, St. Louis, Mo.) and the absorbance at 405 nm is measured in an ELISA reader. Concentrations of HBsAg-specific antibodies in serum samples are estimated from a standard curve generated with a standard serum pooled from four mice given i.p. injections of 2 μg rHBsAg with complete Freund's adjunvant (Life Technologies, Carlsbad, Calif.).

20.4. Lymphocyte Proliferation Assay.

HBsAg-specific T cell proliferation is performed as described (Chow et al., 1998). Spleen cells are harvested from mice in each group and pooled for the assay. One hundred microliters of $2\times10^6$/ml splenocytes in complete DNEM, supplemented with 5% heat-inactivated fetal calf serum, 2 mM glutamine, 100 U/ml penicillin, 100 μg/ml streptomycin, and $5\times10^{-5}$ M 2-ME, is added in triplicate to each well of 96-well round-bottom plates, followed by the addition of HBsAg at a final concentration of 3 or 1 μg/ml for experiments with BALB/c mice and 10 μg/ml for B10.M mice. Bovine serum albumin (10 μg/ml) serves as negative control and concanavalin A (2 μg/ml) as positive mitogenic control. After 4 days in culture, the cells are pulsed with [$^3$H]thymidine (1 μgCi/well) for 18 h and then the incorporated radioactivity is measured. The stimulation index is calculated as the mean cpm of the stimulated cells divided by the mean cpm of the positive control wells.

Example 21: Hepatitis B Vaccination of Mice Using PLGA-PEG-PLGA Hydrogel-Delivered HbsAg and rhC3-Derivative H5

Example 21 is performed according to the methods of example 20 using the HbsAg-non-responder strain B10.M (Jackson Laboratory, USA) for evaluation of HbsAg vaccination with PLGA-PEG-PLGA hydrogel-delivered HbsAg and rhC3-derivative H5. The HbsAg-responder mouse strain BALB/c is used for control.

21.1. Preparation of PLGA-PEG-PLGA Hydrogel-Embedded HbsAg and rhC3-Derivative H5.

Recombinant HBsAg (rHBsAg) produced in yeast *Saccharomyces cerevisiae* (MBS) and rhC3-derivative H5 are formulated with PLGA-PEG-PLGA hydrogel in the solution phase so that each dose of vaccine contains 2 μg HBsAg and 0.25 mg rhC3-derivative H5 per 200 μl hydrogel.

21.2. Immunization.

All mice are immunized at 6-8 weeks of age. The mice are divided into groups (each n=5) which are injected s.c. in the back with a 0.2 ml volume of one of the following vaccines: 2 μg HBsAg in saline, 2 μg HBsAg+0.25 mg rhC3-derivative H5 in saline, 2 μg HBsAg in hydrogel, or 2 μg HBsAg+0.25 mg rhC3-derivative H5 in hydrogel. In an additional control mice receive 2 μg HBsAg, H-B-Vax II (Merck Sharp & Dohme, West Point, Pa.) which is formulated with aluminium hydroxide.

Responder BALB/c mice receive one dose of each vaccine, and serum samples are collected 4 weeks later to measure anti-HBsAg antibody levels. BALB/c mice are boosted one day after sera collection with the same vaccine, and splenocytes are harvested 2 weeks later and tested in the T cell-proliferation assay.

Non-responder B10.M mice receive two doses of each vaccine at an 8 week interval, and serum samples are collected 4 weeks after the first immunization and 2 weeks after the second immunization for determination of the anti-HBsAg antibody levels. Splenocytes are harvested 2 weeks after the second immunization for the T cell-proliferation assay.

21.3. Determination of HbsAg-Specific Antibodies.

The assay is performed as described in Example 20.3.

21.4. Lymphocyte Proliferation Assay.

The assay is performed as described in Example 20.4.

Example 22: Hepatitis B Vaccination of Mice Using PLGA-PEG-PLGA Hydrogel-Embedded HbsAg and Non-Embedded CVF Example 22 is performed using the HbsAg-non-responder strain B10.M (Jackson Laboratory, USA) for evaluation of HbsAg vaccination with PLGA-PEG-PLGA hydrogel-embedded HbsAg and co-injected non-embedded CVF. CVF is injected twice at the site of antigen prevention, first 1 h after injection of the hydrogel, and second 24 h later. The HbsAg-responder mouse strain BALB/c is used for control.

22.1. Preparation of PLGA-PEG-PLGA Hydrogel-Embedded HbsAg.

Recombinant HBsAg (rHBsAg) produced in yeast *Saccharomyces cerevisiae* (MBS) is formulated with PLGA-PEG-PLGA hydrogel in the solution phase so that each dose of vaccine contains 2 μg HBsAg per 200 μl hydrogel.

22.2. Immunization.

All mice are immunized at 6-8 weeks of age. The mice are divided into groups (each n=5) which are injected s.c. in the back with a 0.2 ml volume of one of the following vaccines: 2 μg HBsAg in saline (no additional CVF injections) or 2 μg HBsAg in hydrogel followed by CVF injections. Purified CVF (0.25 mg/kg in phosphate-buffered saline) is injected at the site of hydrogel injection 1 h after injection of the hydrogel, followed by a second injection 24 h later at the same location.

In an additional control mice receive 2 μg HBsAg, H—B—Vax II (Merck Sharp & Dohme, West Point, Pa.) which is formulated with aluminium hydroxide.

Responder BALB/c mice receive one immunization treatment, and serum samples are collected 4 weeks later to measure anti-HBsAg antibody levels. In order to assess T cell proliferation, BALB/c mice are boosted one day after sera collection with the same procedure, and splenocytes are harvested 2 weeks later and tested in the T cell-proliferation assay.

Non-responder B10.M mice receive two immunization treatments at an 8 week interval, and serum samples are collected 4 weeks after the first immunization and 2 weeks after the second immunization for determination of the anti-HBsAg antibody levels. Splenocytes are harvested 2 weeks after the second immunization for the T cell-proliferation assay.

22.3. Determination of HbsAg-Specific Antibodies.

The assay is performed as described in Example 20.3.

22.4. Lymphocyte Proliferation Assay.

The assay is performed as described in Example 20.4.

Example 23: Hepatitis B Vaccination of Mice Using PLGA-PEG-PLGA Hydrogel-Embedded HbsAg and Non-Embedded rhC3-Derivative H5

Example 23 is performed using the HbsAg-non-responder strain B10.M (Jackson Laboratory, USA) for evaluation of HbsAg vaccination with PLGA-PEG-PLGA hydrogel-embedded HbsAg and co-injected non-embedded rhC3-derivastive H5. The rhC3-derivastive H5 is injected twice at the site of antigen presentation, first 1 h after injection of the hydrogel, and second 24 h later. The HbsAg-responder mouse strain BALB/c is used for control.

23.1. Preparation of PLGA-PEG-PLGA Hydrogel-Embedded HbsAg.

Recombinant HBsAg (rHBsAg) produced in yeast *Saccharomyces cerevisiae* (MBS) is formulated with PLGA-PEG-PLGA hydrogel in the solution phase so that each dose of vaccine contains 2 μg HBsAg per 200 μl hydrogel.

23.2. Immunization.

All mice are immunized at 6-8 weeks of age. The mice are divided into groups (each n=5) which are injected s.c. in the back with a 0.2 ml volume of one of the following vaccines: 2 μg HBsAg in saline (no additional rhC3-derivastive H5 injections) or 2 HBsAg in hydrogel followed by rhC3-derivastive H5 injections. The rhC3-derivastive H5 (0.25 mg/kg in phosphate-buffered saline) is injected at the site of hydrogel injection 1 h after injection of the hydrogel, followed by a second injection 24 h later at the same location.

In an additional control mice receive 2 μg HBsAg, H—B—Vax II (Merck Sharp & Dohme, West Point, Pa.) which is formulated with aluminium hydroxide.

Responder BALB/c mice receive one immunization treatment, and serum samples are collected 4 weeks later to measure anti-HBsAg antibody levels. In order to assess T cell proliferation, BALB/c mice are boosted one day after sera collection with the same procedure, and splenocytes are harvested 2 weeks later and tested in the T cell-proliferation assay.

Non-responder B10.M mice receive two immunization treatments at an 8 week interval, and serum samples are collected 4 weeks after the first immunization and 2 weeks after the second immunization for determination of the anti-HBsAg antibody levels. Splenocytes are harvested 2 weeks after the second immunization for the T cell-proliferation assay.

23.3. Determination of HbsAg-Specific Antibodies.

The assay is performed as described in Example 20.3.

23.4. Lymphocyte Proliferation Assay.

The assay is performed as described in Example 20.4.

The invention claimed is:

1. A pharmaceutical composition comprising a therapeutically effective dose of at least one recombinant human C3-derivative having the SEQ ID Nos: 1-3 and at least one antigen for vaccination, and wherein the recombinant human C3-derivative is coated or absorbed on or embedded in a first matrix, wherein the first matrix is selected as to enable sustained release of the recombinant human C3-derivative, and wherein, optionally, the antigen is coated or absorbed on or embedded in a second matrix different from the first matrix, wherein the second matrix is an adjuvant providing a depot effect for antigen presentation, and wherein the first and/or the second matrix is a thermogelling hydrogel having a gelling temperature between 20° C. and 40° C.; wherein the thermogelling hydrogel is a thermogelling PLGA-PEG-PLGA hydrogel wherein the gelling temperature is between 20° C. and 40° C.

2. The composition according to claim 1, wherein the at least one antigen and the recombinant human C3-derivative are coated or absorbed on or embedded in a matrix, wherein the matrix is selected as to enable sustained release of both the antigen and the recombinant human C3-derivative.

3. The composition according to claim 1, wherein the first and/or the second matrix is a biostable polymer.

4. The composition according to claim 1, wherein the 90% degradation of the polymer weight in body environment and/or 90% release of the antigen and/or recombinant human C3-derivative from the polymer is completed within 1 to 10 days.

5. The composition according to claim 1, wherein the second matrix is selected from the group consisting of aluminium salts, oil in water or water in oil emulsions, e.g. FIA, Montanide, Adjuvant 65 and Lipovant, liposomes, polymeric microsphere adjuvants, and virosomes.

6. The composition according to claim 1, wherein all components are mixed as a single preparation, or wherein the first matrix and the rhC3-derivative are mixed as a first preparation and the antigen and the second matrix according are mixed as a second preparation.

7. The composition according to claim 1, wherein the composition is galenically prepared for administration by injection or by implantation, subcutaneously, intradermally, intramuscularly, nasally, transbucally, transmucosally, sublingually, rectally, vaginally, intraocularly, intra tumor, or topically.

8. Method for manufacturing a pharmaceutical composition according to claim 6, wherein the components are mixed with each other in a therapeutically effective quantity, and wherein optionally galenic compounds are additionally admixed to one or all of the preparations.

9. Method for the induction of immune responses in mammals, wherein a composition according to claim 1 is administered in a therapeutically effective dose to a person in need of treatment, and wherein the recombinant human C3 derivative is co-injected or co-implanted with one or more antigens adsorbed onto the second matrix.

10. The composition according to claim 1, wherein the thermogelling hydrogel is a reverse thermogelling polymer.

11. The composition according to claim 1, wherein the hydrogel is selected from the group consisting of polyethylene, polypropylene, polyethylene oxide (PEO), polypropylene oxide (PPO), polyurethane, polyurea, polyamides, polycarbonates, polyaldehydes, polyorthoesters, polyiminocarbonates, poly caprolactone (PCL), poly-D,L-lactic acid (PDLLA), poly-L-lactic acid (PLLA), lactides of said lactic acids, polyphosphazenes, polyglycolic acids, albumin, monomethoxypoly(ethylene glycol) (MPEG), trimethylated chitosan derivatives, or copolymers or mixtures of any of the above.

12. The composition according to claim 1, wherein the hydrogel is selected from the group consisting of poly (lactic-co-glycolic acid) (PLGA), copolymers of L-lactide and D,L-lactide, polyester copolymers, diblock copolymers consisting of MPEG and PCL, MPEG and PCL-ran-PLLA, MPEG and PLGA, PEO and PLLA, trimethylated chitosan and a,ß-glycerophosphate, triblock copolymers consisting of PEO and PLLA, PLGA-PEG-PLGA, PEG-PLGA-PEG, PEG-PCL-PEG, and PEO-PPO-PEO (Poloxamers).

13. The composition according to claim 1, wherein the second matrix is selected from the group consisting of aluminium phosphate or aluminium hydroxide gels.

14. The composition according to claim 1, wherein the antigen is a hepatitis B surface antigen (HBsAg).

15. The composition according to claim 14, wherein the hepatitis B surface antigen (HBsAg) is a combination with Cobra venom Factor (CVF).

* * * * *

SEQUENCE LISTING

```
<160> NUMBER OF SEQ ID NOS: 7

<210> SEQ ID NO 1
<211> LENGTH: 1276
<212> TYPE: PRT
<213> ORGANISM: Artificial
<220> FEATURE:
<223> OTHER INFORMATION: Synthesized

<400> SEQUENCE: 1

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
            20                  25                  30

Val Thr Val Thr Val His Asp Phe Pro Gly Lys Lys Leu Val Leu Ser
        35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80
```

```
Asn Lys Phe Val Thr Val Gln Ala Thr Phe Gly Thr Gln Val Val Glu
            85                  90                  95
Lys Val Val Leu Val Ser Leu Gln Ser Gly Tyr Leu Phe Ile Gln Thr
            100                 105                 110
Asp Lys Thr Ile Tyr Thr Pro Gly Ser Thr Val Leu Tyr Arg Ile Phe
            115                 120                 125
Thr Val Asn His Lys Leu Leu Pro Val Gly Arg Thr Val Met Val Asn
            130                 135                 140
Ile Glu Asn Pro Glu Gly Ile Pro Val Lys Gln Asp Ser Leu Ser Ser
145                 150                 155                 160
Gln Asn Gln Leu Gly Val Leu Pro Leu Ser Trp Asp Ile Pro Glu Leu
            165                 170                 175
Val Asn Met Gly Gln Trp Lys Ile Arg Ala Tyr Tyr Glu Asn Ser Pro
            180                 185                 190
Gln Gln Val Phe Ser Thr Glu Phe Glu Val Lys Glu Tyr Val Leu Pro
            195                 200                 205
Ser Phe Glu Val Ile Val Glu Pro Thr Glu Lys Phe Tyr Tyr Ile Tyr
            210                 215                 220
Asn Glu Lys Gly Leu Glu Val Thr Ile Thr Ala Arg Phe Leu Tyr Gly
225                 230                 235                 240
Lys Lys Val Glu Gly Thr Ala Phe Val Ile Phe Gly Ile Gln Asp Gly
            245                 250                 255
Glu Gln Arg Ile Ser Leu Pro Glu Ser Leu Lys Arg Ile Pro Ile Glu
            260                 265                 270
Asp Gly Ser Gly Glu Val Val Leu Ser Arg Lys Val Leu Leu Asp Gly
            275                 280                 285
Val Gln Asn Pro Arg Ala Glu Asp Leu Val Gly Lys Ser Leu Tyr Val
            290                 295                 300
Ser Ala Thr Val Ile Leu His Ser Gly Ser Asp Met Val Gln Ala Glu
305                 310                 315                 320
Arg Ser Gly Ile Pro Ile Val Thr Ser Pro Tyr Gln Ile His Phe Thr
            325                 330                 335
Lys Thr Pro Lys Tyr Phe Lys Pro Gly Met Pro Phe Asp Leu Met Val
            340                 345                 350
Phe Val Thr Asn Pro Asp Gly Ser Pro Ala Tyr Arg Val Pro Val Ala
            355                 360                 365
Val Gln Gly Glu Asp Thr Val Gln Ser Leu Thr Gln Gly Asp Gly Val
            370                 375                 380
Ala Lys Leu Ser Ile Asn Thr His Pro Ser Gln Lys Pro Leu Ser Ile
385                 390                 395                 400
Thr Val Arg Thr Lys Lys Gln Glu Leu Ser Glu Ala Glu Gln Ala Thr
            405                 410                 415
Arg Thr Met Gln Ala Leu Pro Tyr Ser Thr Val Gly Asn Ser Asn Asn
            420                 425                 430
Tyr Leu His Leu Ser Val Leu Arg Thr Glu Leu Arg Pro Gly Glu Thr
            435                 440                 445
Leu Asn Val Asn Phe Leu Leu Arg Met Asp Arg Ala His Glu Ala Lys
            450                 455                 460
Ile Arg Tyr Tyr Thr Tyr Leu Ile Met Asn Lys Gly Arg Leu Leu Lys
465                 470                 475                 480
Ala Gly Arg Gln Val Arg Glu Pro Gly Gln Asp Leu Val Val Leu Pro
            485                 490                 495
```

```
Leu Ser Ile Thr Thr Asp Phe Ile Pro Ser Phe Arg Leu Val Ala Tyr
                500                 505                 510

Tyr Thr Leu Ile Gly Ala Ser Gly Gln Arg Glu Val Val Ala Asp Ser
        515                 520                 525

Val Trp Val Asp Val Lys Asp Ser Cys Val Gly Ser Leu Val Val Lys
    530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
                565                 570                 575

Asp Lys Gly Val Phe Val Leu Asn Lys Lys Asn Lys Leu Thr Gln Ser
            580                 585                 590

Lys Ile Trp Asp Val Val Glu Lys Ala Asp Ile Gly Cys Thr Pro Gly
        595                 600                 605

Ser Gly Lys Asp Tyr Ala Gly Val Phe Ser Asp Ala Gly Leu Thr Phe
610                 615                 620

Thr Ser Ser Ser Gly Gln Gln Thr Ala Gln Arg Ala Glu Leu Gln Cys
625                 630                 635                 640

Pro Gln Pro Ala Ala Asp Asp Asn Glu Asp Gly Phe Ile Ala Asp Ser
                645                 650                 655

Asp Ile Ile Ser Arg Ser Asp Phe Pro Lys Ser Trp Leu Trp Leu Thr
            660                 665                 670

Lys Asp Leu Thr Glu Glu Pro Asn Ser Gln Gly Ile Ser Ser Lys Thr
        675                 680                 685

Met Ser Phe Tyr Leu Arg Asp Ser Ile Thr Thr Trp Val Val Leu Ala
690                 695                 700

Val Ser Phe Thr Pro Thr Lys Gly Ile Cys Val Ala Glu Pro Tyr Glu
705                 710                 715                 720

Ile Arg Val Met Lys Val Phe Phe Ile Asp Leu Gln Met Pro Tyr Ser
                725                 730                 735

Val Val Lys Asn Glu Gln Val Glu Ile Arg Ala Ile Leu His Asn Tyr
            740                 745                 750

Val Asn Glu Asp Ile Tyr Val Arg Val Glu Leu Leu Tyr Asn Pro Ala
        755                 760                 765

Phe Cys Ser Ala Ser Thr Lys Gly Gln Arg Tyr Arg Gln Gln Phe Pro
770                 775                 780

Ile Lys Ala Leu Ser Ser Arg Ala Val Pro Phe Val Ile Val Pro Leu
785                 790                 795                 800

Glu Gln Gly Leu His Asp Val Glu Ile Lys Ala Ser Val Gln Glu Ala
                805                 810                 815

Leu Trp Ser Asp Gly Val Arg Lys Lys Leu Lys Val Val Pro Glu Gly
            820                 825                 830

Val Gln Lys Ser Ile Val Thr Ile Val Lys Leu Asp Pro Arg Ala Lys
        835                 840                 845

Gly Val Gly Gly Thr Gln Leu Glu Val Ile Lys Ala Arg Lys Leu Asp
850                 855                 860

Asp Arg Val Pro Asp Thr Glu Ile Glu Thr Lys Ile Ile Ile Gln Gly
865                 870                 875                 880

Asp Pro Val Ala Gln Ile Ile Glu Asn Ser Ile Asp Gly Ser Lys Leu
                885                 890                 895

Asn Glu Ile Gln Met Pro Thr His Lys Asp Leu Asn Leu Asp Ile Thr
            900                 905                 910
```

Ile Glu Leu Pro Asp Arg Glu Val Pro Ile Arg Tyr Arg Ile Asn Tyr
            915                 920                 925

Glu Asn Ala Leu Leu Ala Arg Thr Val Glu Thr Lys Leu Asn Gln Asp
        930                 935                 940

Ile Thr Val Thr Ala Ser Gly Asp Gly Lys Ala Thr Met Thr Ile Leu
945                 950                 955                 960

Thr Phe Tyr Asn Ala Gln Leu Gln Glu Lys Ala Asn Val Cys Asn Lys
                965                 970                 975

Phe His Leu Asn Val Ser Val Glu Asn Ile His Leu Asn Ala Met Gly
            980                 985                 990

Ala Lys Gly Ala Leu Met Leu Lys Ile Cys Thr Arg Tyr Leu Gly Glu
        995                 1000                1005

Val Asp Ser Thr Met Thr Ile Ile Asp Ile Ser Met Leu Thr Gly
    1010                1015                1020

Phe Leu Pro Asp Ala Glu Asp Leu Thr Arg Leu Ser Lys Gly Val
    1025                1030                1035

Asp Arg Tyr Ile Ser Arg Tyr Glu Val Asp Asn Asn Met Ala Gln
    1040                1045                1050

Lys Val Ala Val Ile Ile Tyr Leu Asn Lys Val Ser His Ser Glu
    1055                1060                1065

Asp Glu Cys Leu His Phe Lys Ile Leu Lys His Phe Glu Val Gly
    1070                1075                1080

Phe Ile Gln Pro Gly Ser Val Lys Val Tyr Ser Tyr Tyr Asn Leu
    1085                1090                1095

Asp Glu Lys Cys Thr Lys Phe Tyr His Pro Asp Lys Gly Thr Gly
    1100                1105                1110

Leu Leu Asn Lys Ile Cys Ile Gly Asn Val Cys Arg Cys Ala Gly
    1115                1120                1125

Glu Thr Cys Ser Ser Leu Asn His Gln Glu Arg Ile Asp Val Pro
    1130                1135                1140

Leu Gln Ile Glu Lys Ala Cys Glu Thr Asn Val Asp Tyr Val Tyr
    1145                1150                1155

Lys Thr Lys Leu Leu Arg Ile Glu Glu Gln Asp Gly Asn Asp Ile
    1160                1165                1170

Tyr Val Met Asp Val Leu Glu Val Ile Lys Gln Gly Thr Asp Glu
    1175                1180                1185

Asn Pro Arg Ala Lys Thr His Gln Tyr Ile Ser Gln Arg Lys Cys
    1190                1195                1200

Gln Glu Ala Leu Asn Leu Lys Val Asn Asp Asp Tyr Leu Ile Trp
    1205                1210                1215

Gly Ser Arg Ser Asp Leu Leu Pro Thr Lys Asp Lys Ile Ser Tyr
    1220                1225                1230

Ile Ile Thr Lys Asn Thr Trp Ile Glu Arg Trp Pro His Glu Asp
    1235                1240                1245

Glu Cys Gln Glu Glu Glu Phe Gln Lys Leu Cys Asp Asp Phe Ala
    1250                1255                1260

Gln Phe Ser Tyr Thr Leu Thr Glu Phe Gly Cys Pro Thr
    1265                1270                1275

<210> SEQ ID NO 2
<211> LENGTH: 1637
<212> TYPE: PRT
<213> ORGANISM: Artificial
<220> FEATURE:
<223> OTHER INFORMATION: Synthesized

```
<400> SEQUENCE: 2

Ser Pro Met Tyr Ser Ile Ile Thr Pro Asn Ile Leu Arg Leu Glu Ser
 1               5                  10                  15

Glu Glu Thr Met Val Leu Glu Ala His Asp Ala Gln Gly Asp Val Pro
             20                  25                  30

Val Thr Val Thr Val His Asp Phe Pro Gly Lys Lys Leu Val Leu Ser
         35                  40                  45

Ser Glu Lys Thr Val Leu Thr Pro Ala Thr Asn His Met Gly Asn Val
 50                  55                  60

Thr Phe Thr Ile Pro Ala Asn Arg Glu Phe Lys Ser Glu Lys Gly Arg
 65                  70                  75                  80

Asn Lys Phe Val Thr Val Gln Ala Thr Phe Gly Thr Gln Val Val Glu
                 85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
    130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
            180                 185                 190

Gln Gln Val Phe Ser Thr Glu Phe Glu Val Lys Glu Tyr Val Leu Pro
        195                 200                 205

Ser Phe Glu Val Ile Val Glu Pro Thr Glu Lys Phe Tyr Tyr Ile Tyr
    210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Pro Ile Glu
            260                 265                 270

Asp Gly Ser Gly Glu Val Val Leu Ser Arg Lys Val Leu Leu Asp Gly
        275                 280                 285

Val Gln Asn Leu Arg Ala Glu Asp Leu Val Gly Lys Ser Leu Tyr Val
    290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335

Lys Thr Pro Lys Tyr Phe Lys Pro Gly Met Pro Phe Asp Leu Met Val
            340                 345                 350

Phe Val Thr Asn Pro Asp Gly Ser Pro Ala Tyr Arg Val Pro Val Ala
        355                 360                 365

Val Gln Gly Glu Asp Thr Val Gln Ser Leu Thr Gln Gly Asp Gly Val
    370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Glu Ala Glu Gln Ala Thr
                405                 410                 415
```

-continued

Arg Thr Met Gln Ala Leu Pro Tyr Ser Thr Val Gly Asn Ser Asn Asn
                420                 425                 430

Tyr Leu His Leu Ser Val Leu Arg Thr Glu Leu Arg Pro Gly Glu Thr
        435                 440                 445

Leu Asn Val Asn Phe Leu Leu Arg Met Asp Arg Ala His Glu Ala Lys
    450                 455                 460

Ile Arg Tyr Tyr Thr Tyr Leu Ile Met Asn Lys Gly Arg Leu Leu Lys
465                 470                 475                 480

Ala Gly Arg Gln Val Arg Glu Pro Gly Gln Asp Leu Val Val Leu Pro
                485                 490                 495

Leu Ser Ile Thr Thr Asp Phe Ile Pro Ser Phe Arg Leu Val Ala Tyr
        500                 505                 510

Tyr Thr Leu Ile Gly Ala Ser Gly Gln Arg Glu Val Val Ala Asp Ser
    515                 520                 525

Val Trp Val Asp Val Lys Asp Ser Cys Val Gly Ser Leu Val Val Lys
    530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
                565                 570                 575

Asp Lys Gly Val Phe Val Leu Asn Lys Lys Asn Lys Leu Thr Gln Ser
        580                 585                 590

Lys Ile Trp Asp Val Val Glu Lys Ala Asp Ile Gly Cys Thr Pro Gly
    595                 600                 605

Ser Gly Lys Asp Tyr Ala Gly Val Phe Ser Asp Ala Gly Leu Thr Phe
    610                 615                 620

Thr Ser Ser Ser Gly Gln Gln Thr Ala Gln Arg Ala Glu Leu Gln Cys
625                 630                 635                 640

Pro Gln Pro Ala Ala Ser Val Gln Leu Thr Glu Lys Arg Met Asp Lys
                645                 650                 655

Val Gly Lys Tyr Pro Lys Glu Leu Arg Lys Cys Cys Glu Asp Gly Met
        660                 665                 670

Arg Glu Asn Pro Met Arg Phe Ser Cys Gln Arg Arg Thr Arg Phe Ile
    675                 680                 685

Ser Leu Gly Glu Ala Cys Lys Lys Val Phe Leu Asp Cys Cys Asn Tyr
690                 695                 700

Ile Thr Glu Leu Arg Arg Gln His Ala Arg Ala Ser His Leu Gly Leu
705                 710                 715                 720

Ala Arg Ser Asn Leu Asp Glu Asp Ile Ile Ala Glu Glu Asn Ile Val
                725                 730                 735

Ser Arg Ser Glu Phe Pro Glu Ser Trp Leu Trp Asn Val Glu Asp Leu
        740                 745                 750

Lys Glu Pro Pro Lys Asn Gly Ile Ser Thr Lys Leu Met Asn Ile Phe
    755                 760                 765

Leu Lys Asp Ser Ile Thr Thr Trp Glu Ile Leu Ala Val Ser Met Ser
    770                 775                 780

Asp Lys Lys Gly Ile Cys Val Ala Asp Pro Phe Glu Val Thr Val Met
785                 790                 795                 800

Gln Asp Phe Phe Ile Asp Leu Arg Leu Pro Tyr Ser Val Val Arg Asn
                805                 810                 815

Glu Gln Val Glu Ile Arg Ala Val Leu Tyr Asn Tyr Arg Gln Asn Gln
        820                 825                 830

-continued

Glu Leu Lys Val Arg Val Glu Leu Leu His Asn Pro Ala Phe Cys Ser
835                 840                 845

Leu Ala Thr Thr Lys Arg Arg His Gln Gln Thr Val Thr Ile Pro Pro
850                 855                 860

Lys Ser Ser Leu Ser Val Pro Tyr Val Ile Val Pro Leu Lys Thr Gly
865                 870                 875                 880

Leu Gln Glu Val Glu Val Lys Ala Ala Val Tyr His His Phe Ile Ser
            885                 890                 895

Asp Gly Val Arg Lys Ser Leu Lys Val Val Pro Glu Gly Ile Arg Met
            900                 905                 910

Asn Lys Thr Val Ala Val Arg Thr Leu Asp Pro Glu Arg Leu Gly Arg
            915                 920                 925

Glu Gly Val Gln Lys Glu Asp Ile Pro Pro Ala Asp Leu Ser Asp Gln
            930                 935                 940

Val Pro Asp Thr Glu Ser Glu Thr Arg Ile Leu Leu Gln Gly Thr Pro
945                 950                 955                 960

Val Ala Gln Met Thr Glu Asp Ala Val Asp Ala Glu Arg Leu Lys His
                965                 970                 975

Leu Ile Val Thr Pro Ser Gly Cys Gly Glu Gln Asn Met Ile Gly Met
                980                 985                 990

Thr Pro Thr Val Ile Ala Val His  Tyr Leu Asp Glu Thr  Glu Gln Trp
        995                 1000                1005

Glu Lys  Phe Gly Leu Glu Lys  Arg Gln Gly Ala Leu  Glu Leu Ile
    1010                1015                1020

Lys Lys  Gly Tyr Thr Gln Gln  Leu Ala Phe Arg Gln  Pro Ser Ser
    1025                1030                1035

Ala Phe  Ala Ala Phe Val Lys  Arg Ala Pro Ser Thr  Trp Leu Thr
    1040                1045                1050

Ala Tyr  Val Val Lys Val Phe  Ser Leu Ala Val Asn  Leu Ile Ala
    1055                1060                1065

Ile Asp  Ser Gln Val Leu Cys  Gly Ala Val Lys Trp  Leu Ile Leu
    1070                1075                1080

Glu Lys  Gln Lys Pro Asp Gly  Val Phe Gln Glu Asp  Ala Pro Val
    1085                1090                1095

Ile His  Gln Glu Met Ile Gly  Gly Leu Arg Asn Asn  Asn Glu Lys
    1100                1105                1110

Asp Met  Ala Leu Thr Ala Phe  Val Leu Ile Ser Leu  Gln Glu Ala
    1115                1120                1125

Lys Asp  Ile Cys Glu Glu Gln  Val Asn Ser Leu Pro  Gly Ser Ile
    1130                1135                1140

Thr Lys  Ala Gly Asp Phe Leu  Glu Ala Asn Tyr Met  Asn Leu Gln
    1145                1150                1155

Arg Ser  Tyr Thr Val Ala Ile  Ala Gly Tyr Ala Leu  Ala Gln Met
    1160                1165                1170

Gly Arg  Leu Lys Gly Pro Leu  Leu Asn Lys Phe Leu  Thr Thr Ala
    1175                1180                1185

Lys Asp  Lys Asn Arg Trp Glu  Asp Pro Gly Lys Gln  Leu Tyr Asn
    1190                1195                1200

Val Glu  Ala Thr Ser Tyr Ala  Leu Leu Ala Leu Leu  Gln Leu Lys
    1205                1210                1215

Asp Phe  Asp Phe Val Pro Pro  Val Val Arg Trp Leu  Asn Glu Gln
    1220                1225                1230

-continued

Arg Tyr Tyr Gly Gly Gly Tyr Gly Ser Thr Gln Ala Thr Phe Met
1235                1240                1245

Val Phe Gln Ala Leu Ala Gln Tyr Gln Lys Asp Ala Pro Asp His
1250                1255                1260

Gln Glu Leu Asn Leu Asp Val Ser Leu Gln Leu Pro Ser Arg Ser
1265                1270                1275

Ser Lys Ile Thr His Arg Ile His Trp Glu Ser Ala Ser Leu Leu
1280                1285                1290

Arg Ser Glu Glu Thr Lys Glu Asn Glu Gly Phe Thr Val Thr Ala
1295                1300                1305

Glu Gly Lys Gly Gln Gly Thr Leu Ser Val Val Thr Met Tyr His
1310                1315                1320

Ala Lys Ala Lys Asp Gln Leu Thr Cys Asn Lys Phe Asp Leu Lys
1325                1330                1335

Val Thr Ile Lys Pro Ala Pro Glu Thr Glu Lys Arg Pro Gln Asp
1340                1345                1350

Ala Lys Asn Thr Met Ile Leu Glu Ile Cys Thr Arg Tyr Arg Gly
1355                1360                1365

Asp Gln Asp Ala Thr Met Ser Ile Leu Asp Ile Ser Met Met Thr
1370                1375                1380

Gly Phe Ala Pro Asp Thr Asp Asp Leu Lys Gln Leu Ala Asn Gly
1385                1390                1395

Val Asp Arg Tyr Ile Ser Lys Tyr Glu Leu Asp Lys Ala Phe Ser
1400                1405                1410

Asp Arg Asn Thr Leu Ile Ile Tyr Leu Asp Lys Val Ser His Ser
1415                1420                1425

Glu Asp Asp Cys Leu Ala Phe Lys Val His Gln Tyr Phe Asn Val
1430                1435                1440

Glu Leu Ile Gln Pro Gly Ala Val Lys Val Tyr Ala Tyr Tyr Asn
1445                1450                1455

Leu Glu Glu Ser Cys Thr Arg Phe Tyr His Pro Glu Lys Glu Asp
1460                1465                1470

Gly Lys Leu Asn Lys Leu Cys Arg Asp Glu Leu Cys Arg Cys Ala
1475                1480                1485

Glu Glu Asn Cys Phe Ile Gln Lys Ser Asp Asp Lys Val Thr Leu
1490                1495                1500

Glu Glu Arg Leu Asp Lys Ala Cys Glu Pro Gly Val Asp Tyr Val
1505                1510                1515

Tyr Lys Thr Lys Leu Leu Arg Ile Glu Glu Gln Asp Gly Asn Asp
1520                1525                1530

Ile Tyr Val Met Asp Val Leu Glu Val Ile Lys Gln Gly Thr Asp
1535                1540                1545

Glu Asn Pro Arg Ala Lys Thr His Gln Tyr Ile Ser Gln Arg Lys
1550                1555                1560

Cys Gln Glu Ala Leu Asn Leu Lys Val Asn Asp Asp Tyr Leu Ile
1565                1570                1575

Trp Gly Ser Arg Ser Asp Leu Leu Pro Thr Lys Asp Lys Ile Ser
1580                1585                1590

Tyr Ile Ile Thr Lys Asn Thr Trp Ile Glu Arg Trp Pro His Glu
1595                1600                1605

```
Asp Glu Cys Gln Glu Glu Glu Phe Gln Lys Leu Cys Asp Asp Phe
    1610                1615                1620

Ala Gln Phe Ser Tyr Thr Leu Thr Glu Phe Gly Cys Pro Thr
    1625                1630                1635

<210> SEQ ID NO 3
<211> LENGTH: 1637
<212> TYPE: PRT
<213> ORGANISM: Artificial
<220> FEATURE:
<223> OTHER INFORMATION: Synthesized

<400> SEQUENCE: 3

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
            20                  25                  30

Val Thr Val Thr Val His Asp Phe Pro Gly Lys Lys Leu Val Leu Ser
        35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
            180                 185                 190

Gln Gln Val Phe Ser Thr Glu Phe Glu Val Lys Glu Tyr Val Leu Pro
        195                 200                 205

Ser Phe Glu Val Ile Val Glu Pro Thr Glu Lys Phe Tyr Tyr Ile Tyr
    210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Pro Ile Glu
            260                 265                 270

Asp Gly Ser Gly Glu Val Val Leu Ser Arg Lys Val Leu Leu Asp Gly
        275                 280                 285

Val Gln Asn Leu Arg Ala Glu Asp Leu Val Gly Lys Ser Leu Tyr Val
    290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335
```

```
Lys Thr Pro Lys Tyr Phe Lys Pro Gly Met Pro Phe Asp Leu Met Val
                340                 345                 350

Phe Val Thr Asn Pro Asp Gly Ser Pro Ala Tyr Arg Val Pro Val Ala
            355                 360                 365

Val Gln Gly Glu Asp Thr Val Gln Ser Leu Thr Gln Gly Asp Gly Val
        370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Glu Ala Glu Gln Ala Thr
                405                 410                 415

Arg Thr Met Gln Ala Leu Pro Tyr Ser Thr Val Gly Asn Ser Asn Asn
            420                 425                 430

Tyr Leu His Leu Ser Val Leu Arg Thr Glu Leu Arg Pro Gly Glu Thr
        435                 440                 445

Leu Asn Val Asn Phe Leu Leu Arg Met Asp Arg Ala His Glu Ala Lys
        450                 455                 460

Ile Arg Tyr Tyr Thr Tyr Leu Ile Met Asn Lys Gly Arg Leu Leu Lys
465                 470                 475                 480

Ala Gly Arg Gln Val Arg Glu Pro Gly Gln Asp Leu Val Val Leu Pro
                485                 490                 495

Leu Ser Ile Thr Thr Asp Phe Ile Pro Ser Phe Arg Leu Val Ala Tyr
            500                 505                 510

Tyr Thr Leu Ile Gly Ala Ser Gly Gln Arg Glu Val Val Ala Asp Ser
        515                 520                 525

Val Trp Val Asp Val Lys Asp Ser Cys Val Gly Ser Leu Val Val Lys
    530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
                565                 570                 575

Asp Lys Gly Val Phe Val Leu Asn Lys Lys Asn Lys Leu Thr Gln Ser
            580                 585                 590

Lys Ile Trp Asp Val Val Glu Lys Ala Asp Ile Gly Cys Thr Pro Gly
        595                 600                 605

Ser Gly Lys Asp Tyr Ala Gly Val Phe Ser Asp Ala Gly Leu Thr Phe
        610                 615                 620

Thr Ser Ser Ser Gly Gln Gln Thr Ala Gln Arg Ala Glu Leu Gln Cys
625                 630                 635                 640

Pro Gln Pro Ala Ala Ser Val Gln Leu Thr Glu Lys Arg Met Asp Lys
                645                 650                 655

Val Gly Lys Tyr Pro Lys Glu Leu Arg Lys Cys Cys Glu Asp Gly Met
            660                 665                 670

Arg Glu Asn Pro Met Arg Phe Ser Cys Gln Arg Arg Thr Arg Phe Ile
        675                 680                 685

Ser Leu Gly Glu Ala Cys Lys Lys Val Phe Leu Asp Cys Cys Asn Tyr
        690                 695                 700

Ile Thr Glu Leu Arg Arg Gln His Ala Arg Ala Ser His Leu Gly Leu
705                 710                 715                 720

Ala Arg Ser Asn Leu Asp Glu Asp Ile Ile Ala Glu Glu Asn Ile Val
                725                 730                 735

Ser Arg Ser Glu Phe Pro Glu Ser Trp Leu Trp Asn Val Glu Asp Leu
            740                 745                 750
```

```
Lys Glu Pro Pro Lys Asn Gly Ile Ser Thr Lys Leu Met Asn Ile Phe
        755                 760                 765

Leu Lys Asp Ser Ile Thr Thr Trp Glu Ile Leu Ala Val Ser Met Ser
770                 775                 780

Asp Lys Lys Gly Ile Cys Val Ala Asp Pro Phe Glu Val Thr Val Met
785                 790                 795                 800

Gln Asp Phe Phe Ile Asp Leu Arg Leu Pro Tyr Ser Val Val Arg Asn
        805                 810                 815

Glu Gln Val Glu Ile Arg Ala Val Leu Tyr Asn Tyr Arg Gln Asn Gln
        820                 825                 830

Glu Leu Lys Val Arg Val Glu Leu Leu His Asn Pro Ala Phe Cys Ser
        835                 840                 845

Leu Ala Thr Thr Lys Arg Arg His Gln Gln Thr Val Thr Ile Pro Pro
850                 855                 860

Lys Ser Ser Leu Ser Val Pro Tyr Val Ile Val Pro Leu Lys Thr Gly
865                 870                 875                 880

Leu Gln Glu Val Glu Val Lys Ala Ala Val Tyr His His Phe Ile Ser
        885                 890                 895

Asp Gly Val Arg Lys Ser Leu Lys Val Val Pro Glu Gly Ile Arg Met
        900                 905                 910

Asn Lys Thr Val Ala Val Arg Thr Leu Asp Pro Glu Arg Leu Gly Arg
        915                 920                 925

Glu Gly Val Gln Lys Glu Asp Ile Pro Pro Ala Asp Leu Ser Asp Gln
        930                 935                 940

Val Pro Asp Thr Glu Ser Glu Thr Arg Ile Leu Leu Gln Gly Thr Pro
945                 950                 955                 960

Val Ala Gln Met Thr Glu Asp Ala Val Asp Ala Glu Arg Leu Lys His
                965                 970                 975

Leu Ile Val Thr Pro Ser Gly Cys Gly Glu Gln Asn Met Ile Gly Met
        980                 985                 990

Thr Pro Thr Val Ile Ala Val His Tyr Leu Asp Glu Thr Glu Gln Trp
        995                 1000                1005

Glu Lys Phe Gly Leu Glu Lys Arg Gln Gly Ala Leu Glu Leu Ile
1010                1015                1020

Lys Lys Gly Tyr Thr Gln Gln Leu Ala Phe Arg Gln Pro Ser Ser
1025                1030                1035

Ala Phe Ala Ala Phe Val Lys Arg Ala Pro Ser Thr Trp Leu Thr
1040                1045                1050

Ala Tyr Val Val Lys Val Phe Ser Leu Ala Val Asn Leu Ile Ala
1055                1060                1065

Ile Asp Ser Gln Val Leu Cys Gly Ala Val Lys Trp Leu Ile Leu
1070                1075                1080

Glu Lys Gln Lys Pro Asp Gly Val Phe Gln Glu Asp Ala Pro Val
1085                1090                1095

Ile His Gln Glu Met Ile Gly Gly Leu Arg Asn Asn Asn Glu Lys
1100                1105                1110

Asp Met Ala Leu Thr Ala Phe Val Leu Ile Ser Leu Gln Glu Ala
1115                1120                1125

Lys Asp Ile Cys Glu Glu Gln Val Asn Ser Leu Pro Gly Ser Ile
1130                1135                1140

Thr Lys Ala Gly Asp Phe Leu Glu Ala Asn Tyr Met Asn Leu Gln
1145                1150                1155
```

```
Arg Ser Tyr Thr Val Ala Ile Ala Gly Tyr Ala Leu Ala Gln Met
    1160                1165                1170

Gly Arg Leu Lys Gly Pro Leu Leu Asn Lys Phe Leu Thr Thr Ala
    1175                1180                1185

Lys Asp Lys Asn Arg Trp Glu Asp Pro Gly Lys Gln Leu Tyr Asn
    1190                1195                1200

Val Glu Ala Thr Ser Tyr Ala Leu Leu Ala Leu Leu Gln Leu Lys
    1205                1210                1215

Asp Phe Asp Phe Val Pro Pro Val Val Arg Trp Leu Asn Glu Gln
    1220                1225                1230

Arg Tyr Tyr Gly Gly Gly Tyr Gly Ser Thr Gln Ala Thr Phe Met
    1235                1240                1245

Val Phe Gln Ala Leu Ala Gln Tyr Gln Lys Asp Ala Pro Asp His
    1250                1255                1260

Gln Glu Leu Asn Leu Asp Val Ser Leu Gln Leu Pro Ser Arg Ser
    1265                1270                1275

Ser Lys Ile Thr His Arg Ile His Trp Glu Ser Ala Ser Leu Leu
    1280                1285                1290

Arg Ser Glu Glu Thr Lys Glu Asn Glu Gly Phe Thr Val Thr Ala
    1295                1300                1305

Glu Gly Lys Gly Gln Gly Thr Leu Ser Val Val Thr Met Tyr His
    1310                1315                1320

Ala Lys Ala Lys Asp Gln Leu Thr Cys Asn Lys Phe Asp Leu Lys
    1325                1330                1335

Val Thr Ile Lys Pro Ala Pro Glu Thr Glu Lys Arg Pro Gln Asp
    1340                1345                1350

Ala Lys Asn Thr Met Ile Leu Glu Ile Cys Thr Arg Tyr Leu Gly
    1355                1360                1365

Glu Val Asp Ser Thr Met Thr Ile Ile Asp Ile Ser Met Leu Thr
    1370                1375                1380

Gly Phe Leu Pro Asp Ala Glu Asp Leu Thr Arg Leu Ser Lys Gly
    1385                1390                1395

Val Asp Arg Tyr Ile Ser Arg Tyr Glu Val Asp Asn Asn Met Ala
    1400                1405                1410

Gln Lys Val Ala Val Ile Ile Tyr Leu Asn Lys Val Ser His Ser
    1415                1420                1425

Glu Asp Glu Cys Leu His Phe Lys Ile Leu Lys His Phe Glu Val
    1430                1435                1440

Gly Phe Ile Gln Pro Gly Ser Val Lys Val Tyr Ser Tyr Tyr Asn
    1445                1450                1455

Leu Asp Glu Lys Cys Thr Lys Phe Tyr His Pro Asp Lys Gly Thr
    1460                1465                1470

Gly Leu Leu Asn Lys Ile Cys Ile Gly Asn Val Cys Arg Cys Ala
    1475                1480                1485

Gly Glu Thr Cys Ser Ser Leu Asn His Gln Glu Arg Ile Asp Val
    1490                1495                1500

Pro Leu Gln Ile Glu Lys Ala Cys Glu Thr Asn Val Asp Tyr Val
    1505                1510                1515

Tyr Lys Thr Lys Leu Leu Arg Ile Glu Glu Gln Asp Gly Asn Asp
    1520                1525                1530

Ile Tyr Val Met Asp Val Leu Glu Val Ile Lys Gln Gly Thr Asp
    1535                1540                1545
```

```
Glu Asn Pro Arg Ala Lys Thr His Gln Tyr Ile Ser Gln Arg Lys
    1550            1555                1560

Cys Gln Glu Ala Leu Asn Leu Lys Val Asn Asp Asp Tyr Leu Ile
    1565            1570                1575

Trp Gly Ser Arg Ser Asp Leu Leu Pro Thr Lys Asp Lys Ile Ser
    1580            1585                1590

Tyr Ile Ile Thr Lys Asn Thr Trp Ile Glu Arg Trp Pro His Glu
    1595            1600                1605

Asp Glu Cys Gln Glu Glu Glu Phe Gln Lys Leu Cys Asp Asp Phe
    1610            1615                1620

Ala Gln Phe Ser Tyr Thr Leu Thr Glu Phe Gly Cys Pro Thr
    1625            1630                1635

<210> SEQ ID NO 4
<211> LENGTH: 24
<212> TYPE: DNA
<213> ORGANISM: Artificial
<220> FEATURE:
<223> OTHER INFORMATION: Synthesized

<400> SEQUENCE: 4
tctgtgtggc agaccccttc gagg                                              24

<210> SEQ ID NO 5
<211> LENGTH: 41
<212> TYPE: DNA
<213> ORGANISM: Artificial
<220> FEATURE:
<223> OTHER INFORMATION: Synthesized

<400> SEQUENCE: 5
gagaaggcct gttcctttat ccggatggta gaaccgggta c                           41

<210> SEQ ID NO 6
<211> LENGTH: 35
<212> TYPE: DNA
<213> ORGANISM: Artificial
<220> FEATURE:
<223> OTHER INFORMATION: Synthesized

<400> SEQUENCE: 6
ccggttctac catccggata aaggaacagg ccttc                                  35

<210> SEQ ID NO 7
<211> LENGTH: 31
<212> TYPE: DNA
<213> ORGANISM: Artificial
<220> FEATURE:
<223> OTHER INFORMATION: Synthesized

<400> SEQUENCE: 7
catccatgac atagatatca ttaccatctt g                                      31
```